(12) United States Patent
Weisinger et al.

(10) Patent No.: US 9,279,127 B2
(45) Date of Patent: Mar. 8, 2016

(54) ADIPOCYTE-SPECIFIC CONSTRUCTS AND METHODS FOR INHIBITING PLATELET-TYPE 12 LIPOXYGENASE EXPRESSION

(75) Inventors: Gary Weisinger, Rehovot (IL); Rona Limor, Herzliya (IL); Naftali Stern, Nir-Zvi (IL)

(73) Assignee: The Medical Research Fund at the Tel-Aviv Sourasky Medical Center, Tel-Aviv (IL)

( * ) Notice: Subject to any disclaimer, the term of this patent is extended or adjusted under 35 U.S.C. 154(b) by 463 days.

(21) Appl. No.: 12/513,006

(22) PCT Filed: Nov. 1, 2007

(86) PCT No.: PCT/IL2007/001333
§ 371 (c)(1),
(2), (4) Date: Jan. 5, 2010

(87) PCT Pub. No.: WO2008/053487
PCT Pub. Date: May 8, 2008

(65) Prior Publication Data
US 2011/0038923 A1    Feb. 17, 2011

Related U.S. Application Data

(60) Provisional application No. 60/855,736, filed on Nov. 1, 2006.

(51) Int. Cl.
| | |
|---|---|
| *C07H 21/04* | (2006.01) |
| *A61K 31/70* | (2006.01) |
| *C12N 15/63* | (2006.01) |
| *C12N 15/113* | (2010.01) |
| *A61K 48/00* | (2006.01) |

(52) U.S. Cl.
CPC ........ *C12N 15/1137* (2013.01); *A61K 48/0058* (2013.01); *A61K 48/0066* (2013.01); *C12N 2310/11* (2013.01); *C12N 2310/111* (2013.01); *C12N 2320/32* (2013.01); *C12N 2330/51* (2013.01)

(58) Field of Classification Search
CPC ........... C12N 15/1137; C12N 2310/11; C12N 2310/111; C12N 2320/32; C12N 2330/51; A61K 48/0058; A61K 48/0066
USPC ......... 536/24.1, 24.5; 514/44; 435/455, 320.1
See application file for complete search history.

(56) References Cited

U.S. PATENT DOCUMENTS

| | | | |
|---|---|---|---|
| 5,436,330 A | 7/1995 | Taira | |
| 5,545,729 A | 8/1996 | Goodchild | |
| 5,631,115 A | 5/1997 | Ohtsuka | |
| 5,861,268 A * | 1/1999 | Tang et al. | ........................ 435/25 |
| 6,046,224 A * | 4/2000 | Natarajan et al. | .............. 514/381 |
| 6,110,462 A | 8/2000 | Barbas | |
| 6,191,169 B1 * | 2/2001 | Nadler et al. | .................. 514/562 |
| 6,277,981 B1 | 8/2001 | Tu | |
| 6,326,174 B1 | 12/2001 | Joyce | |
| 6,506,559 B1 | 1/2003 | Fire | |
| 6,794,143 B2 * | 9/2004 | Blumenfeld et al. | ........ 435/6.11 |
| 6,972,171 B1 | 12/2005 | Schlingensiepen | |
| 7,022,832 B2 | 4/2006 | Malvy | |
| 7,585,623 B2 * | 9/2009 | Matsuzawa et al. | ......... 435/6.11 |
| 2002/0013368 A1 | 1/2002 | Collin | |
| 2002/0076395 A1 * | 6/2002 | Crystal et al. | ................. 424/93.2 |
| 2002/0137210 A1 | 9/2002 | Churikov | |
| 2003/0220287 A1 * | 11/2003 | Phillips et al. | ................... 514/44 |
| 2005/0100907 A1 | 5/2005 | Kreutzer | |
| 2005/0261485 A1 | 11/2005 | Uchida | |
| 2006/0078902 A1 | 4/2006 | Bunting | |
| 2006/0178330 A1 | 8/2006 | Thompson | |
| 2006/0217331 A1 | 9/2006 | Vargeese | |
| 2010/0150885 A1 * | 6/2010 | Tseng et al. | ................ 424/93.21 |

FOREIGN PATENT DOCUMENTS

| | | | |
|---|---|---|---|
| WO | 88/04300 | 6/1988 | |
| WO | WO 88/04300 | 6/1988 | ............. C12N 15/00 |
| WO | 99/59562 | 11/1999 | |
| WO | WO 99/59562 | 11/1999 | |
| WO | 00/66720 | 11/2000 | |
| WO | WO 00/66720 | 11/2000 | |
| WO | 01/75164 | 10/2001 | |

(Continued)

OTHER PUBLICATIONS

Alam et al. Lung surfactant protein B promoter function is dependent on the helical phasing, orientation and combinatorial actions of cis-DNA elements. Gene 282:103-111, 2002.*

Muller et al. Repression of lac promoter as a function of distance, phase and quality of an auxiliary lac operator. J. Mol. Biol. 257:21-29, 1996.*

Xie et al. Domains of the rat rDNA promoter must be aligned sterospecifically. Molecular and Cellular Biology 12:1266-1275, 1992.*

(Continued)

*Primary Examiner* — Quang Nguyen
(74) *Attorney, Agent, or Firm* — Winston & Strawn LLP

(57) ABSTRACT

The present invention is directed to constructs, compositions and methods for modulating platelet-type 12 lipoxygenase (12-LO) in adipose tissue in vivo. Specifically, the invention provides constructs encoding expression-inhibiting oligonucleic acids, e.g., antisense and RNA interfering (RNAi) molecules, targeted to a platelet-type 12-LO gene or a transcript thereof, which are capable of reducing or silencing platelet-type 12-LO expression specifically in adipocytes and pre-adipocytes. Vectors of these constructs (including, but not limited to, viral vectors), compositions of them and methods of using same for the treatment and amelioration of conditions associated with excess fat cell mass and obesity are also provided.

15 Claims, 24 Drawing Sheets

(56) References Cited

FOREIGN PATENT DOCUMENTS

| | | | |
|---|---|---|---|
| WO | WO 01/75164 A2 | 10/2001 | |
| WO | 02/44321 | 6/2002 | |
| WO | WO 02/44321 A2 | 6/2002 | |
| WO | 03/104477 | 12/2003 | |
| WO | 03/104494 | 12/2003 | |
| WO | 03/104495 | 12/2003 | |
| WO | WO 03/104477 A2 | 12/2003 | |
| WO | WO 03/104494 A1 | 12/2003 | |
| WO | WO 03/104495 A1 | 12/2003 | |
| WO | 2004/029070 | 4/2004 | |
| WO | WO 2004/029070 A2 | 4/2004 | |
| WO | 2004/041197 | 5/2004 | |
| WO | WO 2004/041197 A2 | 5/2004 | ............. A61K 31/70 |
| WO | 2005/083124 | 9/2005 | |
| WO | WO 2005/083124 A1 | 9/2005 | ............. A61K 48/00 |
| WO | 2006/039285 | 4/2006 | |
| WO | WO 2006/039285 A2 | 4/2006 | |
| WO | 2006/060484 | 6/2006 | |
| WO | WO 2006/060454 A2 | 6/2006 | |
| WO | 2006/094406 | 9/2006 | |
| WO | WO 2006/094406 A1 | 9/2006 | |

OTHER PUBLICATIONS

Limor et al. A novel form of platelet-type 12-lipoxygenase mRNA in human vascular smooth muscle cell. Hypertension 38:864-871, 2001.*

Allen et al., "Morphological and Biochemical Characterization and Analysis of Apoptosis". J. Pharmacol. Toxicol. Methods (1997); 37: 215-28.

Brash, A.R., "Lipoxygenases: Occurrence, Functions, Catalysis, and Acquisition of Substrate", J. Biol. Chem. (1999); 274(24: 23679-82.

Connacher et al., "Clinical studies with the β-adrenoceptor agonist BRL 26830A$^{1,2}$", Am J Clin Nutr. (1992); 55(1 Suppl): 258S-261S. Review Degterev et al., "A decade of caspases". Oncogene (2003); 22: 8543-67.

Della-Fera et al., 2001, "Adipocyte apoptosis in the regulation of body fat mass by Leptin", Diabetes Obes Metab (2001); 3: 299-110.

Ettinger et al., "Recombinant Variant of Ciliary Neurotrophic Factor for Weight Loss in Obese Adulsts: A Randomized, Dose-Ranging Study". JAMA. (2003); 289(14): 1826-32

Garg A. "Lipodystrophies". Am J Med (2000); 108: 143-52.

Géloën et al., "Regression of white adipose tissue in diabetic rats". Am J Physiol (1989); 257: E547-E553.

Goeptar et al., "Cytotoxicity of Mitomycin C and Adriamycin in Freshly Isolated Rat Hepatocytes: The Role of Cytochrome P450". Cancer Res. (1994); 54: 2411-8.

Gullicksen et al., "Adipose tissue cellularity and apoptosis after intracerebroventricular injections of leptin and 21 days of recovery in rats". Int J Obes (2003); 27: 302-12.

Hauner et al., "Promoting Effect of Glucocorticoids on the Differentiation of Human Adipocyte Precursor Cells Cultured in a Chemically Defined Medium", J Clin INvest (1989); 84: 1663-70.

He et al., "The Mouse obese Gene". J. Biol. Chem. (1995); 270(48): 28887-91.

Hukshorn et al., "The effect of pegylated recombinant human leptin (PEG-OB) on weight loss and inflammatory status in obese subjects". Int J Obes (2002); 26: 504-9.

Jernås et al., "Separation of human adipocytes by size: hypertrophic fat cells display distinct gene expression". FASEB J. (2006); 20: 1540-42.

Kay et al., "Evidence for gene transfer and expression of factor IX in haemophilia B patients treated with an AAV vector". Nat. Genetics (2000); 24: 257-61.

Kita et al., "Identification of the promoter region required for human adiponectin gene transcription: Association with CCAAT/enhancer binding protein-β and tumor necrosiss factor-α" BBRC (2005); 331: 484-90.

La Gamma et al., "Genetically modified Primary Astrocytes as Cellular Vehicles for Gene Therapy in the Brain". Cell Transplantation (1993); 2(3): 207-14.

Limor et al., "Contaminant eluted from solid-phase plasmid affinity-purfication protocol columns is not found using liquid-phase methods and can be prevented". J. Biochem. Biophys. Methods (1999); 40: 57-64.

Limor et al, "A Novel form of Platelet-Type 12-Lipoxygenase mRNA in Human Vascular Smooth Muscle Cells". Hypertension (2001); 38(4): 864-71.

Lloreta J. et al., "Ultrastructural features of highly active antiretroviral therapy-associated partial lipodystrophy". Virchows Arch (2002); 441: 599-604.

Madsen et al., "Adipocyte differentiation of 3T3-L1 preadipocytes is dependent on lipoxygenase activity during the intial stages of the diferentiation process". Biochem. J. (2003); 375(3): 539-49.

Magun et al., "The effect of adipocyte differentiation on the capacity of 3T3-L1 cells to undergo apoptosis in response to growth factor deprivation". Int J Obes (1993); 22: 567-71.

Margareto et al., "A new NPY-antagonist strongly stimulates apoptosis and lipolysis on white adipocytes in an obesity model" Life Sci (2000); 68: 99-107.

Mason et al., "Regulation of Leptin Promoter Function by Sp1, C/EBP, and a Novel Factor". Endocrinology (1998); 139(3): 1013-22.

Moran, J.H. and Schnellmann, R.G., "A Rapid β-NADH-Linked Fluorescence Assay for Lactate Dehydrogenase in Cellular Death". J. Pharmacol. Toxicol. Methods (1996); 35(1): 41-44.

Nakai et al., "AAV serotype 2 vectors preferentially integrate into active genes in mice". Nat. Genetics (2003); 34(3): 297-302.

Nelson-Dooley et al., "Novel Treatments for Obesity and Osteoporosis: Targeting Apoptotic Pathways in Adipocytes". Curr Med Chem. (2005); 12: 2215-25.

Park, Y. and Pariza, M.C., "Lipoxygenase inhibitors inhibit heparin-releasable lipoprotein lipase activity in 3T3-L1 adipocytes and enhance body fat reduction in mice by conjugated linoleic acid". Biochimica et Biophysica Acta (2001): 1534(1): 27-33.

Pidgeon, Graham P. et al., "Mechanisms controlling cell cycle arrest and induction of apoptosis after 12-lipoxygenase inhibition in prostate cancer cells". Cancer Res. (2002); 62(9): 2721-7.

Prins et al., "Apoptosis of human adipocytes in vitro". Biochem Biophys Res Commun (1994); 201(2): 500-7.

Prins, J.B. and O'Rahilly, S., "Regulation of adipose cell number in man". Clin Sci (1997): 92: 3-11.

Prins et al., "Tumor Necrosis Factor-α Induces of Apoptosis of Human Adipose Cells". Diabetes (1997): 46: 1939-44.

Qian et al:, "Brain Administration of Leptin Causes Deletion of Adipocytes by Apoptosis". Endocrinology (1998); 139(2): 791-4.

Rigas et al., "Rapid plasmid library screening using RecA-coated biotinylated probes". Proc. Natl. Acad. Sci. U.S.A. (1986); 83: 9591-5.

Salma et al., "Temporal recruitment of CCAAT/enhancer-binding proteins to early and late adipogenic promoters in vivo". J. Mol. Endocrinol. (2006); 36:139-51.

Scislowski P.W. and Jetton T.J., "Dopamine Receptor Agonist Treatment Increases Apoptosis and Fatty Acid Oxidation of White Adipose Tissue in ob/ob Mice". Diabetes (1999); 48(Suppl): A266.

Sjöström, L. and William-Olsson, T., "Prospective studies on adipose tissue development in man". Int J Obes (1981); 5: 597-604.

Sorisky et al., "Adipose cell apoptosis: death in the energy depot". Int J Obes (2000); 24(Suppl 4): S3-S7.

Tong et al., "The mechanisms of lipoxygenase inhibitor-induced apoptosis in human breast cancer cells". Biochem. Biophys. Res. Commun. (2002); 296: 942-8.

Weisinger et al., "Multiple negative elements upstream of the murine c-myc gene share nuclear factor binding sites with SV40 and polyoma enhancers", Oncogene (1988); 3: 635-46.

Bleich et al., "Resistance to type 1 diabetes induction in 12-lipoxygenase knockout mice", J. of Clinical Investigation, vol. 103, (1999); 1431-1436.

Sun et al., "Disruption of 12/15-Lipoxygenase Expression in Peritoneal Macrophages". J of Biol. Chem., vol. 271, (1996); 24055-24062.

(56) References Cited

OTHER PUBLICATIONS

Allen et al., (1991) Morphological and Biochemical Characterization and Analysis of Apoptosis. J Pharmacol Toxicol Methods 37: 215-28.
Brash (1999) Lipoxygenases: Occurrence, Functions, Catalysis, and Acquisition of Substrate. J Biol Chem 274(34): 23679-82.
Connacher et al., (1992) Clinical studies with the β-adrenoceptor agonist BRL 26830A1,2. Am J Clin Nutr 55(1 Suppl): 258S-261S.
Degterev et al., (2003) A decade of caspases. Oncogene 22: 8543-67.
Della-Fera et al., (2001) Adipocyte apoptosis in the regulation of body fat mass by Leptin. Diabetes Obes Metab 3: 299-310.
Ettinger et al., (2003) Recombinant Variant of Ciliary Neurotrophic Factor for Weight Loss in Obese Adults: A Randomized, Dose-Ranging Study. JAMA. 289(14): 1826-32.
Garg (2000) Lipodystrophies. Am J Med 108: 143-52.
Geloen et al., (1989) Regression of white adipose tissue in diabetic rats. Am J Physiol 257: E547-E553.
Goeptar et al., (1994) Cytotoxicity of Mitomycin C and Adriamycin in Freshly Isolated Rat Hepatocytes: The Role of Cytochrome P450. Cancer Res 54: 2411-8.
Gullicksen et al., (2003) Adipose tissue cellularity and apoptosis after intracerebroventricular injections of leptin and 21 days of recovery in rats. Int J Obes 27: 302-12.
Hauner et al., (1989) Promoting Effect of Glucocorticoids on the Differentiation of Human Adipocyte Precursor Cells Cultured in a Chemically Defined Medium. J Clin Invest 84: 1663-70.
He et al., (1995) The Mouse obese Gene J Biol Chem 270(48): 28887-91.
Hukshorn et al., (2002) The effect of pegylated recombinant human leptin (PEG-OB) on weight loss and inflammatory status in obese subjects. Int J Obes 25: 504-93.
Jemas et al., (2006) Separation of human adipocytes by size: hypertrophic fat cells display distinct gene expression. FASEB J 20: 1540-42.
Kay et al, (2000) Evidence for gene transfer and expression of factor IX in haemophilia B patients treated with an AAV vector. Nat Genetics 24: 257-61.
Kita et al., (2005) Identification of the promoter region required for human adiponectin gene transcription: Association with CCAAT/enhancer binding protein-β and tumor necrosis factor-α. BBRC 331: 484-90.
La Gamma et al., (1993) Genetically modified Primary Astrocytes as Cellular Vehicles for Gene Therapy in the Brain. Cell Transplantation 2(3): 207-14.
Limor et al., (1999) Contaminant eluted from solid-phase plasmid affinitypurification protocol columns is not found using liquid-phase methods and can be prevented. J Biochem Biophys Methods 40: 57-64.
Lloreta et al., (2002) Ultrastructural features of highly active antiretroviral therapy-associated partial lipodystrophy. Virchows Arch 441: 599-604.
Madsen et al., (2003) Adipocyte differentiation of 3T3-L1 preadipocytes os dependent on lipoxygenase activity during the initial stages of the differentiation process. Biochem J 375(3): 539-49.
Magun et al., (1998) The effect of adipocyte differentiation on the capacity of 3T3-L1 cells to undergo apoptosis in response to growth factor deprivation. Int J Obes 22: 557-71.
Margareto et al., (2000) A new NPY-antagonist strongly stimulates apoptosis and lipolysis on white adipocytes in an obseity model. Life Sci 68: 99-107.
Mason et al., (1998) Regulation of Leptin Promoter Function by Sp1, C/EBP, and a Novel Factor Endocrinology 139(3): 1013-22.
Moran and Schnellmann (1996) A Rapid β-NADH-Linked Fluorescence Assay for Lactate Dehydrogenase in Cellular Death. J Pharmacol Toxicol Methods 36(1): 41-4.
Nakai et al., (2003) AAV serotype 2 vectors preferentially integrate into active gene in mice. Nat Genetics 34(3): 297-302.
Nelson-Dooley et al., (2005) Novel Treatments for Obesity and Osteoporosis: Targeting Apoptotic Pathways in Adipocytes. Curr Med Chem 12: 2215-25.
Park and Pariza (2001) Lipoxygenase inhibitors inhibit heparin-releasable lipoprotein lipase activity in 3T3-L1 adipocytes and enhance body fat reduction in mice by conjugated linoleic acid. Biochemica et Biophysica Acta 1534(1): 27-33.
Pidgeon et al., (2002) Mechanisms controlling cell cycle arrest and induction of apoptosis after 12-lipoxygenase inhibition in prostate cancer cells. Cancer Res 62(9): 2721-7.
Prins et al., (1994) Apoptosis of human adipocytes in vitro. Biochem Biophys Res Commun 201(2): 500-7.
Prins and O'rahilly (1997) Regulation of adipose cell number in man. Clin Sci 92: 3-11.
Prins et al., (1997) Tumor Necrosis Factor-α Induces Apoptosis of Human Adipose Cells. Diabetes 46: 1939-44.
Qian et al., (1998) Brain Administration of Leptin Causes Deletion of Adipocytes by Apoptosis. Endocrinology 139(2): 791-4.
Rigas et al., (1986) Rapid plasmid library screening using RecA-coated biotinylated probes. Proc Natl Acad Sci USA 83: 9591-5.
Salma et al., (2006) Temporal recruitment of CCAAT/enhancer-binding proteins to early and late adipogenic promoters in vivo. Mol Endocrinol 36: 139-51.
Scislowski and Jetton (1999) Dopamine Receptor Agonist Treatment Increases Apoptosis and Fatty Acid Oxidation of White Adipose Tissue in ob/ob Mice. Diabetes 48(Suppl): A266.
Sjostrom and William-Olsson (1981) Prospective studies on adipose tissue development in man. Int J Obes 5: 597-604.
Sorisky et al., (2000) Adipose cell apoptosis: death in the energy depot. Int J Obes 24(Suppl 4): S3-S7.
Tong et al., (2002) The mechanisms of lipoxygenase inhibitor-induced apoptosis in human breast cancer cells. Biochem Biophys Res Commun 296: 942-8.
Weisinger et al., (1988) Multiple negative elements upstream of the murine c-myc gene share nuclear factor binding sites with SV40 and polyoma enhancers. Oncogene 3: 635-46.

* cited by examiner

| pCMVmp | pCMV600a | |
|---|---|---|
|  |  | Source |
|  |  | Clone −12HETES |
|  |  | Clone + 12HETES |

ADIPOCYTE-SPECIFIC CONSTRUCTS AND METHODS FOR INHIBITING PLATELET-TYPE 12 LIPOXYGENASE EXPRESSION

This application is a 371 filing of International Patent Application PCT/IL2007/001333 filed Nov. 1, 2007, which claims the benefit of application No. 60/855,736 filed Nov. 1, 2006.

FIELD OF THE INVENTION

The present invention is directed to constructs, compositions and methods for modulating expression of platelet-type 12 lipoxygenase (12-LO) in adipose cells, useful for amelioration of obesity and conditions associated therewith.

BACKGROUND OF THE INVENTION

Obesity has become a global epidemic afflicting both children and adults, and gradually spreading from the Western countries to the developing nations as well. It is now widely recognized that obesity is associated with, and is actually a major culprit in numerous comorbidities such as cardiovascular diseases (CVD), type 2 diabetes, hypertension, certain cancers, and sleep apnea/sleep-disordered breathing. As recently acknowledged by a joint American Heart Association and American Diabetes Association (AHA/ADA) statement, obesity is an independent risk factor for CVD, and CVD risks have also been documented in obese children. Obesity is associated with an increased risk of overall morbidity and mortality as well as reduced life expectancy. Indeed, not only obesity but also overweight are now listed as independent cardiovascular risk factors in the joint AHA/ADA call for the prevention of cardiovascular disease and diabetes.

This explicit inclusion of obesity in the first line of major risk confronts the health implications of the most dominant anthropometric change presently afflicting the human race world round, that of increasing visceral and total body fat mass. While finally acknowledged, the cardiovascular significance of this shift in body build is most likely still underestimated, as it apparently now affects even the youngest.

Obesity may comprise a more easily detectable hazard when associated with either some of its recognized sequels, such as the metabolic form of dyslipidemia (low high density lipoprotein cholesterol (HDLc), hypertriglyceridemia), diabetes and/or hypertension, or linked to co-existing risk factors transmitted genetically, independent of obesity. Such subtle interaction of overweight/obesity with cardiovascular disease may be also difficult to demonstrate because cardiovascular risk factors (excluding diabetes) have declined at all body mass index (BMI) levels but the decline appears to be greater at higher BMI levels. Additionally, although there is an increasing array of recognized adipocyte-derived factors that can negatively interact with the vasculature and/or glucose homeostasis, obesity may affect these factors differentially in a person-, gender-, age-, race- or ethnic-specific manner, thus potentially obscuring important adipose mass-dependent relationships. In other words, excess adipose tissue must not only be present, but also turned on to inflict damage.

With the exception of bariatric surgery, which can be presently offered to a limited number of subjects only, the lack of any truly effective treatment for obesity highlights the gravity of current prospects to control the obesity epidemic. Preventive measures have generally failed; effective public and political strategies to reshape lifestyle by proper nutrition and exercise so as to counteract the global obesity trends have not yet been formulated. Finally, the current generation of weight-reducing medications offers limited benefit, and indeed, despite more than a decade of use has failed to impact the global obesity challenge. Health service use and medical costs associated with obesity and related diseases have risen dramatically and are expected to continue to rise.

Hence, novel therapeutic strategies to combat fatness are needed. From a practical medical perspective, perhaps the most urgent need is to substantially reduce fat in individuals already afflicted with obesity, recognizing that excess fat, just like hypercholesterolemia, comprises a substantial health threat.

Apoptosis in Fat Cells

Increases in adipose tissue mass can result from an increase of the volume of adipocytes and/or from a rise in adipocyte number due to proliferation and differentiation of adipocyte precursor cells. These precursor cells, known as "preadipocytes", extensively populate adipose tissue (Hauner et al., 1989).

Although reduction in fat tissue mass generally involves the loss of stored lipids by lipolytic processes, a reduction of the number of adipocytes may also be seen, especially in conditions where large amounts of fat are lost (Sjostrom et al., 1981). Indeed, contrary to former beliefs that weight loss results only from depletion of adipocyte fat stores and is not accompanied by change in fat cell number, there is now growing evidence that decreases in adipose tissue mass in humans could result from a loss of fat cells through programmed cell death (Prins et al., 1994; Prins et al., 1997; Prins et al., 1997b; Lloreta et al., 2002; Garg, 2000.). Fat cell apoptosis is now well recognized in patients with tumor cachexia and in human immunodeficiency virus (HIV) patients during treatment with protease inhibitors. Patients with acquired forms of lipodystrophy (Lawrence syndrome and Barraquer-Simons syndrome) show an immunologically mediated loss of fat cells, probably by apoptosis (Garg, 2000). In rodents, weight loss induced by starvation, streptozotocin-induced diabetes, or intracerebroventricular administration of leptin, results in apoptosis of fat cells (Geloen et al., 1989; Qian et al., 1998). In 3T3-L1 cells, apoptosis may be induced by serum deprivation or exposure to tumor necrosis factor-$\alpha$ (TNF-$\alpha$) and HIV protease inhibitors (Gullicksen et al., 2003; Magun et al., 1998). Collectively these studies reinforce the emerging concept that adipocyte deletion by apoptosis is a significant contributor to the regulation of adipose tissue mass and to adipose tissue loss during weight reduction (Prins et al., 1997; Sorisky et al., 2000; Della-Fera et al., 2001). Further, a number of experimental ways have been proposed by which adipocyte apoptosis can be induced and through which it may potentially serve as a homeostatic mechanism to control fat cell number (Della-Fera et al., 2001; Scislowski et al., 1999; Margareto et al., 2000).

The current methods of induced apoptosis as a potential means to lower fat mass have been recently reviewed by Nelson-Dooley et al (Nelson-Dooley et al., 2005). In vivo adipocyte apoptosis has been successfully applied using leptin, ciliary neurotrophic factor (CNTF), beta-adrenergic agonists and conjugated linoleic acid (CLA) in rodents. However leptin treatment has generally failed in obesity other than leptin deficiency induced obesity due to leptin resistance (Hukshorn et al., 2002) and the overall response to CNTF-analog has been disappointing in terms of absolute weight loss (Ettinger et al., 2003) and the use of beta agonists in humans has been seriously hampered due to side effects (Connacher et al., 1992). Although adipocyte apoptosis can also be induced in vitro using TNF-$\alpha$, its use is limited due to the inherent pro-inflammatory- and pro-atherosclerotic properties of this cytokine. (−)-Epigallocatechin gallate (EGCG) from *Camellia sinensis* and ajoene, a garlic product (Nelson-Dooley et al., 2005) were shown to precipitate apoptosis in vitro, but the adipocyte selectivity of these agents remains uncertain.

Expression-Inhibiting Oligonucleic Acids

The down regulation of specific gene expression in a cell can be effected by oligonucleic acids using techniques known as antisense therapy, RNA interference (RNAi), and enzymatic nucleic acid molecules.

Antisense therapy refers to the process of inactivating target DNA or mRNA sequences through the use of complementary DNA or RNA oligonucleic acids, thereby inhibiting gene transcription or translation. An antisense molecule can be single stranded, double stranded or triple helix.

RNA interference refers to the process of sequence-specific post-transcriptional gene silencing in eukaryotic cells mediated by RNA fragments. The process of post-transcriptional gene silencing is thought to be an evolutionarily conserved defense mechanism used by cells to prevent the expression of foreign genes and is commonly shared by diverse organisms.

Other agents capable of down-regulating expression are enzymatic nucleic acid molecules such as DNAzymes and ribozymes, capable of specifically cleaving an mRNA transcript of interest. DNAzymes are single-stranded deoxyribonucleotides that can cleave both single- and double-stranded target sequences. Ribozymes are catalytic ribonucleic acid molecules that are increasingly being used for the sequence-specific inhibition of gene expression by the cleavage of mRNAs encoding proteins of interest.

Certain publications, e.g. U.S. Pat. No. 6,506,559 and PCT Pub. Nos. WO 01/75164 and WO 02/44321 relate to RNA interfering nucleic acids. International Patent Publication No. WO 2006/060454 teaches methods of designing small interfering RNAs, antisense polynucleotides, and other hybridizing nucleotides. US Patent Application Publication No. 20060217331 discloses chemically modified double stranded nucleic acid molecules for RNA interference. U.S. Pat. No. 6,506,559 discloses a process for inhibition of gene expression of a target gene in a cell using RNA having a region with double-stranded structure, wherein the nucleotide sequences of the duplex region of the RNA and of a portion of the target gene are identical.

The use of gene silencing agents for inducing apoptosis, for example in cancer therapy, has also been disclosed e.g. by WO 2005/083124, WO 2006/094406 and U.S. Patent Application Publication No. 2006/178330.

Adipose Targeting and Adipose-Specific Gene Expression

Administration of various compounds, including gene-silencing agents, to adipose cells and tissue has been contemplated. For example, WO 2004/029070, WO 03/104495, WO 03/104494 and WO 03/104477 to Marcusson et al. disclose methods for blocking adipocyte differentiation and triglyceride accumulation with inhibitors of DYRK4, Interleukin 12 p35, G-alpha-i3 or Transcription factor Dp-1, respectively. These applications suggest the use of various inhibitors including small molecules, antibodies, peptides (including dominant negative peptides) and nucleic acid agents, including ribozymes, inhibitory RNA molecules including siRNA molecules and antisense oligonucleotides.

It is becoming increasingly recognized that specific subpopulations of human adipocytes are the major pathogenic problem in human obesity. In essence, such cells are considered inflammatory and display a unique and specific gene expression profile (Jernas et al., 2006). For example, while both the Adiponectin and Leptin genes are specifically expressed in human adipocytes (Jernas et al., 2006; Mason et al., 1998; He et al., 1995), only the Leptin gene is further over-expressed as the cells become larger inflammatory adipocytes. It seems that different CCAAT/enhancer binding protein (C/EBP) family members bind to the adiponectin and leptin promoters in mature adipocytes and in large-cell adipocytes. It has been suggested, that the presence of an Sp1 binding site next to the C/EBP binding site in the leptin promoter induces preferential binding of the stimulatory C/EBP family member to the site (Mason et al., 1998; Salma et al., 2006). Nucleic acid constructs that would selectively or preferentially induce gene expression in adipose tissue, particularly constructs and vectors for inducing cell death preferentially in large-cell adipocytes, would be beneficial for controlling excess fat mass and pathological conditions associated therewith.

Platelet-Type 12-Lipoxygenase

Lipoxygenases (LOs) are dioxygenase enzymes that incorporate molecular oxygen into unsaturated fatty acids such as arachidonic acid and linoleic acid. These enzymes are named according to the carbon position (5, 12, or 15) at which they introduce oxygen. Arachidonate LOs and their products play an important role in mediating growth factor-induced tumor cell proliferation and appear to enhance the growth and migration of vascular smooth muscle cells (VSMCs). Some LO forms are also involved in LDL oxidation.

To date, several distinct LO genes have been structurally characterized. Three murine 12-LOs are currently recognized, including platelet 12(S)-LO leukocyte type, and an epidermal LO. Another LO, a porcine leukocyte type, has been isolated and cloned from porcine leukocytes, porcine pituitary cells, and bovine tracheal cells. The human platelet-type 12-LO has been cloned from human erythroleukemia cells and found primarily in human platelets, and was also identified in HEL (human erythroleukemia) cells, and umbilical vein endothelial cells. Platelet-type 12-LO metabolizes arachidonic acid to form exclusively 12(S)-hydroxyeicosatetraenoic acid (12-(S)HETE). There is also evidence for the presence of a leukocyte type of 12-LO in human adrenal glomerulosa cells. Additionally, an epidermal 12(R)-LO has recently been cloned from human skin.

Chemical inhibitors of 12-LO, which are not tissue- or cell type-specific, are known in the art. For example, U.S. Patent Application Publication No. 2002/0013368 discloses methods for prevention and/or treatment of diseases in which 5- and 12-LO activity contributes to the pathological condition, such as cancers and inflammation, by administration of 12-methyltetradecanoic acids, alone and in conjunction with other therapeutic compounds. The '368 publication does not teach or suggest inhibition of 12-LO expression or activity in adipocytes.

U.S. Pat. No. 5,861,268 discloses a method for inducing selective apoptosis of tumor cells which comprises contacting the tumor cells and the normal cells used as a control with an amount of a compound which inhibits 12-LO until apoptosis is induced in the tumor cells, wherein apoptosis is induced in the tumor cells without inducing apoptosis in the normal cells, wherein the compound is selected from the group consisting of: (1) a cyclic hydroxamic acid; (2) an aryl aliphatic acid; (3) nordihydro-guaiaretic acid, (NDGA); (4) N-benzyl-N-hydroxy-5-phenylpentanamide (BHPP); (5) baicalein; and (6) an antisense segment of DNA which selectively binds to DNA encoding 12-lipoxygenase. The '268 patent does not disclose specific constructs and methods suitable for inducing apoptosis in adipocytes.

None of the prior art discloses that platelet-type 12-LO may be expressed in human adipocytes or pre-adipocytes and that it may mediate an anti-apoptotic function in these cells. Nowhere in the art is it suggested, taught or demonstrated that inhibition of 12-LO expression or activity may be effectively used to reduce fat cell mass, nor does the art disclose any constructs, compositions or methods for silencing 12-LO in fat cells in vivo. There exists an unmet medical need for effective and safe means for amelioration of conditions associated with excess fat cell mass and obesity.

SUMMARY OF THE INVENTION

The present invention is directed, in general, to the field of body weight management. The invention is directed to constructs, vectors, compositions and methods for modulating platelet-type 12 lipoxygenase (12-LO) in adipose tissue in vivo. Specifically, the invention provides constructs encoding expression-inhibiting oligonucleic acids targeted to a platelet-type 12-LO gene or a transcript thereof, which constructs are capable of specifically inhibiting or silencing platelet-type 12-LO expression in adipocytes and pre-adipocytes, and in sub-populations thereof. Vectors comprising these constructs, including, but not limited to, viral vectors, compositions and host cells comprising them are also provided. The invention further provides methods for the treatment and amelioration of conditions associated with excess fat cell mass and obesity, utilizing a therapeutic agent capable of inhibiting or reducing platelet-type 12-LO expression or activity selectively in fat cells.

The invention is based, in part, on the surprising discovery, that platelet-type 12-LO is expressed in human and rodent preadipocytes and human adipocytes. Unexpectedly, it is further demonstrated herein, that reducing platelet-type 12-LO expression in adipocytes using antisense therapy results in apoptotic cell death that can be prevented, in part, by the addition of exogenous 12 hydroxyeicosatetraenoic acid (HETE), the enzymatic product of 12-LO.

According to a first aspect of the present invention, there are provided novel nucleic acid constructs useful for inhibiting or reducing the expression of platelet-type 12-LO in adipose cells. The novel recombinant constructs of the invention comprise at least one nucleic acid sequence encoding a platelet-type 12-LO expression-inhibiting oligonucleic acid, the nucleic acid sequence being operably linked to at least one adipose-specific transcription regulating sequence. In one preferable embodiment of the present invention, the encoded platelet-type 12-LO expression-inhibiting oligonucleic acid comprises at least one nucleic acid sequence substantially complementary to at least a part of the platelet-type 12-LO gene or transcript thereof.

Thus, there is provided in one embodiment a recombinant nucleic acid construct comprising at least one adipose-specific transcription regulating sequence operably linked to at least one nucleic acid sequence, wherein the at least one nucleic acid sequence encodes an oligonucleic acid comprising at least one sequence substantially complementary to at least a part of the platelet-type lipoxygenase (platelet-type 12-LO) gene or transcript thereof, and wherein the oligonucleic acid inhibits or reduces the expression of platelet-type 12-LO.

In various embodiments, said oligonucleic acid is selected from the group consisting of: an antisense molecule, an RNA interference (RNAi) molecule (e.g. small interfering RNAs (siRNAs) and hairpin RNAs) and an enzymatic nucleic acid molecule (e.g. ribozymes and DNAzymes). In a particular embodiment, said encoded oligonucleic acid is an RNA molecule.

In one particular embodiment, the encoded expression-inhibiting oligonucleic acid is an antisense molecule comprising a sequence substantially complementary to at least one target sequence of a platelet-type 12-LO transcript. In various embodiments, the antisense molecule is selected from the group consisting of a) DNA antisense molecules, b) RNA antisense molecules, c) triplex forming molecules, and d) analogs of a) or b) or c), wherein the oligonucleic acid comprises a sequence substantially complementary to at least a part of a platelet-type 12-LO transcript. In a particular embodiment, said encoded oligonucleic acid is an antisense molecule. In another particular embodiment, said encoded oligonucleic acid is an RNA antisense molecule.

In another embodiment, the encoded antisense molecule is substantially complementary to a platelet-type 12-LO transcript. In another embodiment, the encoded antisense molecule comprises at least one sequence fully complementary to a target sequence of about 20 to about 30 nucleotides of a platelet-type 12-LO transcript. Preferably, the antisense molecule comprises at least a first sequence fully complementary to a first target sequence of about 20 to about 30 nucleotides of the platelet-type 12-LO transcript, and at least a second sequence fully complementary to a second target sequence of about 20 to about 30 nucleotides of said platelet-type 12-LO transcript.

For example, in certain other particular embodiments, said encoded oligonucleic acid has a nucleic acid sequence as set forth in any one of SEQ ID NOS: 1, 2, and 3, as detailed below. In yet another particular embodiment, said encoded oligonucleic acid is an RNA antisense molecule consisting of a nucleic acid sequence as set forth in any one of SEQ ID NOS: 1, 2, and 3. In other particular embodiments, said encoded oligonucleic acid comprises analogs and fragments of the nucleic acid sequences denoted by SEQ ID NOS: 1-3, said analogs and fragments comprising at least one sequence fully complementary to a target sequence of about 20 to about 30 nucleotides of the platelet-type 12-LO transcript.

According to various embodiments, the adipose-specific transcription regulating sequence may be any regulatory sequence (e.g. promoters and enhancers) that induces or enhances expression selectively (or, in other embodiments, preferentially) in adipose cells. In certain particular embodiments, the transcription regulating sequence is adipocyte-specific. In other particular embodiments, said transcription regulating sequence is pre-adipocyte-specific. In alternate particular embodiments, the transcription regulating sequence induces expression in both adipocytes and pre-adipocytes. For example, without limitation, the constructs and vectors of the invention may contain human adiponectin promoter sequences, human adiponectin enhancer sequences, human leptin promoter sequences, human leptin enhancer sequences and combinations thereof.

In one currently preferred particular embodiment, the transcription regulating sequence is a human adiponectin transcription regulating sequence. In another particular embodiment, the transcription regulating sequence is human adiponectin promoter and enhancer. For example, in another particular embodiment a suitable transcription regulating sequence comprises a nucleic acid sequence corresponding to the minimum human adiponectin promoter and enhancer, as set forth in SEQ ID NO: 4 hereinbelow.

In another currently preferred particular embodiment, the transcription regulating sequence is a human leptin transcription regulating sequence. In another particular embodiment, the transcription regulating sequence is human leptin promoter and enhancer. For example, in another particular embodiment a suitable transcription regulating sequence comprises a nucleic acid sequence corresponding to the minimum 138 bp human leptin promoter and enhancer, as set forth in SEQ ID NO: 7 hereinbelow.

In certain other preferable embodiments, the present invention provides nucleic acid constructs that are particularly suitable for mediating gene expression preferentially in large-cell adipocytes, an adipocyte sub-population implicated in obesity and associated pathologies (Jernas et al., 2006). Certain novel recombinant transcription-regulating sequences useful for such targeted expression are further disclosed, as detailed herein.

Thus, in another embodiment, the nucleic acid sequence encoding the platelet-type 12-LO expression-inhibiting oligonucleic acid is operably linked to at least one transcription regulating sequence that induces or enhances gene expression in large-cell adipocytes. Preferably, said transcription regulating sequence does not substantially induce or enhance gene expression in other cell types. In other embodiments, said transcription regulating sequence induces or enhances gene expression to a greater extent in large-cell adipocytes compared to other cell types.

In a particular embodiment, said nucleic acid sequence is operably linked to a plurality of adipose-specific transcription regulating sequences. The plurality of adipose-specific transcription regulating sequences may contain different transcription regulating sequences or may contain multiple copies of the same transcription regulating sequence, for example two or more copies of a particular enhancer sequence in tandem. By means of a non-limitative example, each transcription-regulating sequence may be selected from human adiponectin promoter sequences, human adiponectin enhancer sequences, human leptin promoter sequences, human leptin enhancer sequences and combinations thereof.

In various embodiments, the at least one transcription regulating sequence may be a complete native regulatory sequence of a gene, e.g. a naturally occurring promoter or enhancer, or may be a sequence derived therefrom, e.g. a portion of the native regulatory sequence, a chimeric construction of the native regulatory sequence, a combinatorial construction of one or more native regulatory sequences, or a variant of the native regulatory sequence obtained by, for example, deletion, addition or replacement of at least one nucleotide, retaining the ability to induce gene expression in adipose tissue, or, in particular embodiments, to induce gene expression preferentially in large (inflammatory) adipocytes. For example, the derived sequence may contain one or more CCAAT/enhancer binding protein (C/EBP) binding sites and/or Sp1 binding sites, e.g. adiponectin or leptin C/EBP and/or Sp1 binding sites. In a particular embodiment, said derived transcription regulating sequence contains at least one C/EBP binding site and at least one Sp1 binding site.

In one particular embodiment, the adipose-specific transcription regulating sequences is a recombinant adipose-specific transcription regulating sequence. An exemplary transcription regulating sequence provided by the present invention is a recombinant chimeric promoter and enhancer sequence having a nucleic acid sequence as set forth in SEQ ID NO: 8, as detailed hereinbelow. The chimeric promoter and enhancer sequence contains an adiponectin promoter/enhancer sequence linked to a leptin enhancer region (see FIG. 19). In one embodiment, said chimeric promoter and enhancer sequence induces gene expression preferentially in large cell adipocytes. In other embodiments, the invention provides vectors, constructs and host cells comprising the recombinant chimeric promoter and enhancer sequence and methods of using same for directing adipose-specific gene expression, particularly in large cell adipocytes.

Another exemplary transcription regulating sequence provided by the present invention is a recombinant promoter and enhancer sequence having a nucleic acid sequence as set forth in SEQ ID NO: 9, as detailed hereinbelow. The recombinant promoter and enhancer sequence contains a leptin promoter/enhancer sequence linked to an additional leptin enhancer region (see FIGS. 18 and 26). In one embodiment, said recombinant promoter and enhancer sequence induces gene expression preferentially in large cell adipocytes. In other embodiments, the invention provides vectors, constructs and host cells comprising the recombinant chimeric promoter and enhancer sequence and methods of using same for directing adipose-specific gene expression, particularly in large cell adipocytes.

In another aspect, there are provided vectors comprising the nucleic acid constructs of the invention, including, but not limited to, plasmid vectors, cosmid vectors and viral-based vectors. Thus, in one embodiment, the invention provides a vector comprising a recombinant nucleic acid construct comprising at least one adipose-specific transcription regulating sequence operably linked to at least one nucleic acid sequence, wherein the at least one nucleic acid sequence encodes an oligonucleic acid comprising at least one sequence substantially complementary to at least a part of the platelet-type lipoxygenase (platelet-type 12-LO) gene or transcript thereof, and wherein the oligonucleic acid inhibits or reduces the expression of platelet-type 12-LO. In certain embodiments, the vector is a mammalian expression vector capable of expressing the oligonucleic acids of the invention in a mammalian host cell. Depending on the nature of the oligonucleic acid to be expressed, in various particular embodiments said mammalian expression vector is a single stranded RNA expression vector, a double stranded RNA expression vector, or a DNA expression vector. In a particular embodiment, the vector is a RNA expression vector.

In one particular embodiment, the vector is a viral-based vector, including, but not limited to, lentiviral, herpes and adenoviral systems e.g. gutless adenovirus- or gutless adeno-associated virus (AAV) or retroviral moieties already in use for human gene therapy. In another particular embodiment, the viral vector is a modified gutless AAV shuttle vector comprising a construct of the invention, e.g. Stratagene's (San Diego, Calif., USA) "AAV Helper-Free System". An exemplary viral vector of the invention is pAAVAdi-12LO-A (see FIG. 17); exemplary plasmid vectors of the invention are pUCAdi-h12LoA-pA (see FIGS. 16 and 18), pLepEnhAdipPr12LoA (FIG. 21) pLepp12LoA (FIG. 24) and pLepLepP12LoA (FIG. 27). In yet another particular embodiment, the vector is a retroviral vector, e.g. vectors based on the Molony Murine Leukemia Virus (MoMLV), which have been well characterized and used safely in humans.

In another aspect, the invention provides host cells comprising the vectors of the invention.

In another aspect, the invention provides a pharmaceutical composition comprising a construct or vector of the invention and a pharmaceutically acceptable carrier, excipient or diluent. Thus, in another embodiment, there is provided a pharmaceutical composition comprising a recombinant nucleic acid construct comprising at least one adipose-specific transcription regulating sequence operably linked to at least one nucleic acid sequence, wherein the at least one nucleic acid sequence encodes an oligonucleic acid comprising at least one sequence substantially complementary to at least a part of the platelet-type lipoxygenase (platelet-type 12-LO) gene or transcript thereof, and wherein the oligonucleic acid inhibits or reduces the expression of platelet-type 12-LO, or a vector comprising same.

In a particular embodiment, the carrier is a liposome. In another particular embodiment, the carrier is a recombinant virus particle. The constructs, vectors and compositions of the invention are useful for reducing obesity and ameliorating or preventing conditions associated therewith, as detailed herein. Preferably, the compositions and methods disclosed herein are suitable for the treatment of humans.

In another aspect, the invention provides a method for reducing obesity in a subject in need thereof, comprising administering to the subject an effective amount of a therapeutic agent that reduces platelet-type 12-LO expression or activity selectively in fat cells. In a preferred embodiment, the therapeutic agent comprises a construct of the invention, as detailed herein. Thus, in another embodiment, there is provided a method for reducing obesity in a subject in need thereof, comprising administering to the subject an effective amount of a recombinant nucleic acid construct comprising at least one adipose-specific transcription regulating sequence operably linked to at least one nucleic acid sequence, wherein the at least one nucleic acid sequence encodes an oligonucleic acid comprising at least one sequence substantially complementary to at least a part of the platelet-type lipoxygenase (platelet-type 12-LO) gene or transcript thereof, and wherein the oligonucleic acid inhibits or reduces the expression of platelet-type 12-LO, or a vector comprising same.

In another aspect, the invention provides a method for preventing or ameliorating an obesity-associated condition or a symptom associated therewith in a subject in need thereof, comprising administering to the subject an effective amount of a therapeutic agent which reduces platelet-type 12-LO expression or activity selectively in fat cells. In a preferred embodiment, the therapeutic agent comprises a construct of the invention, as detailed herein. Thus, in another embodiment, there is provided a method for preventing or ameliorating an obesity-associated condition or a symptom associated therewith in a subject in need thereof, comprising administering to the subject an effective amount of a recombinant nucleic acid construct comprising at least one adipose-specific transcription regulating sequence operably linked to at least one nucleic acid sequence, wherein the at least one nucleic acid sequence encodes an oligonucleic acid comprising at least one sequence substantially complementary to at least a part of the platelet-type lipoxygenase (platelet-type 12-LO) gene or transcript thereof, and wherein the oligonucleic acid inhibits or reduces the expression of platelet-type 12-LO, or a vector comprising same. In various particular embodiments, the condition includes, but is not limited to, cardiovascular diseases, type 2 diabetes, hypertension, cancer (e.g. adrenal, pancreatic, prostrate and gastric cancer), osteoarthritis and stroke.

In another aspect, the invention provides a method for reducing fat cell mass in a subject in need thereof, comprising administering to the subject an effective amount of a therapeutic agent that reduces platelet-type 12-LO expression or activity selectively in fat cells. In a preferred embodiment, the therapeutic agent comprises a construct of the invention, as detailed herein. Thus, in another embodiment, there is provided a method for reducing fat cell mass in a subject in need thereof, comprising administering to the subject an effective amount of a recombinant nucleic acid construct comprising at least one adipose-specific transcription regulating sequence operably linked to at least one nucleic acid sequence, wherein the at least one nucleic acid sequence encodes an oligonucleic acid comprising at least one sequence substantially complementary to at least a part of the platelet-type lipoxygenase (platelet-type 12-LO) gene or transcript thereof, and wherein the oligonucleic acid inhibits or reduces the expression of platelet-type 12-LO, or a vector comprising same.

Without wishing to be bound by any theory or mechanism of action, the constructs and vectors of the invention are capable of inducing apoptosis in the target fat cells. In some embodiments, therapeutic reduction of fat cell mass according to the invention is advantageously associated with fat cell apoptosis. Unlike necrosis, which results in fat tissue inflammation and macrophage infiltration, apoptosis is typically unaccompanied by a local inflammatory response, which is a likely independent health hazard.

According to certain embodiments of the present invention, expression of the oligonucleic acids of the invention in the target cell is regulated such that the incidence of apoptosis in fat cells is increased, thereby achieving a partial reduction in fat cell mass. In certain embodiments, such partial increase in apoptotic cell death in the targeted fat tissue allows reduction in fat mass without local inflammation and in the absence of massive systemic release of potentially deleterious fatty acids. In another particular embodiment, the constructs of the invention enhance apoptosis selectively or preferentially in large cell adipocytes.

Thus, in another aspect, the invention provides a method for inducing apoptosis specifically in a cell selected from the group consisting of adipocytes and pre-adipocytes comprising contacting the cell with a therapeutic agent, which reduces platelet-type 12-LO expression or activity. In another embodiment the therapeutic agent is administered to a subject in need thereof in the form of a pharmaceutical composition such that said agent does not substantially induce apoptosis in non-adipose cells. In a preferred embodiment, the therapeutic agent comprises a construct of the invention, as detailed herein. Thus, in another embodiment, there is provided a method for inducing apoptosis specifically in a cell selected from the group consisting of adipocytes and pre-adipocytes, comprising contacting the cell with an effective amount of a recombinant nucleic acid construct comprising at least one adipose-specific transcription regulating sequence operably linked to at least one nucleic acid sequence, wherein the at least one nucleic acid sequence encodes an oligonucleic acid comprising at least one sequence substantially complementary to at least a part of the platelet-type lipoxygenase (platelet-type 12-LO) gene or transcript thereof, and wherein the oligonucleic acid inhibits or reduces the expression of platelet-type 12-LO, or a vector comprising same.

In another aspect, the invention provides a method for inhibiting or reducing the expression of platelet-type 12-LO in a cell selected from adipocytes and pre-adipocytes, comprising contacting the cell with a therapeutic agent, which reduces platelet-type 12-LO expression or activity. In another embodiment the therapeutic agent is administered to a subject in need thereof in the form of a pharmaceutical composition such that said compound does not substantially inhibit the expression of platelet-type 12-LO in non-adipocyte cells. In a preferred embodiment, the therapeutic agent comprises a construct of the invention, as detailed herein. Thus, in another embodiment, there is provided a method for inhibiting or reducing the expression of platelet-type 12-LO in a cell selected from adipocytes and pre-adipocytes, comprising contacting the cell with an effective amount of a recombinant nucleic acid construct comprising at least one adipose-specific transcription regulating sequence operably linked to at least one nucleic acid sequence, wherein the at least one nucleic acid sequence encodes an oligonucleic acid comprising at least one sequence substantially complementary to at least a part of the platelet-type lipoxygenase (platelet-type 12-LO) gene or transcript thereof, and wherein the oligonucleic acid inhibits or reduces the expression of platelet-type 12-LO, or a vector comprising same.

In certain preferable but optional embodiments, the construct of the invention is administered to the subject in the form of a vector, which expresses the desired oligonucleic acid (e.g. a platelet-type 12-LO expression-inhibiting oligonucleic acid) in an adipose target cell. In a particular embodiment, said vector induces expression of said oligonucleic acid in large cell adipocytes. In various other embodiments, said construct or vector is administered to the subject in the form of a pharmaceutical composition further comprising a pharmaceutically acceptable carrier, excipient or diluent. In another particular embodiment, said constructs or vectors are delivered in the form of liposomes or virus particles.

In various particular embodiments, the compositions of the invention are administered locally to specific fat depots (e.g., local delivery to subcutaneous depots; mesenteric intraarterial delivery to visceral fat) or systemically, depending on the chosen fat pool. In various other particular embodiment, the pharmaceutical compositions of this invention may be administered by a manner selected from: 1) systemically, e.g. through intravenous, intra-arterial or subcutaneous injection or inhalation or any mucosal or other spray; 2) locally, e.g. through direct intra- or peri-tissue delivery through injections, ointment or any other form of disposal; and 3) to specific fat depots e.g. the visceral fat depot through intra-arterial injection (e.g., injection to the mesenteric artery/arterial tree). In other particular embodiments, administration may be repeated as necessary until desirable results are obtained.

Other objects, features and advantages of the present invention will become clear from the following description and drawings.

BRIEF DESCRIPTION OF THE DRAWINGS

FIG. 2 illustrates control and 12Lo plasmid maps for constitutively expressed murine and human antisense knockout studies.

FIG. 18 presents schematic representations of adipocyte-specific promoter and enhancer sequences.

DETAILED DESCRIPTION OF THE INVENTION

Figure 1A:
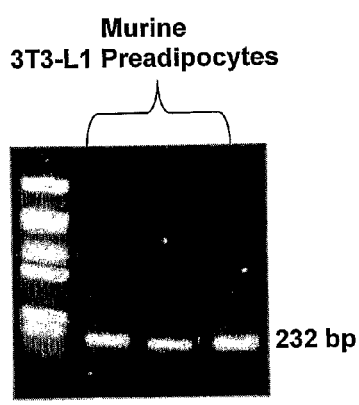
FIG. 1 demonstrates that platelet-type 12-Lipoxygenase RNA is expressed in human and murine fat tissue. Total RNA prepared from the murine 3T3-L1 preadipocyte cell line (FIG. 1A) and primary human preadipocytes and adipocytes (FIG. 1B) were prepared and subjected to PCR using primers for the appropriate species 12-lipoxygenase (mouse or human).

The present invention is directed to constructs, compositions and methods for modulating platelet-type 12 lipoxygenase (12-LO) in adipose tissue in vivo. Specifically, the invention provides expression-inhibiting oligonucleic acids including antisense and RNA interfering (RNAi) molecules targeted to a platelet-type 12-LO gene or a transcript thereof and therapeutic compositions comprising same, which are capable of specifically inhibiting or silencing platelet-type 12-LO expression in adipocytes and pre-adipocytes. Constructs comprising these compounds, vectors comprising them and methods of using same for the treatment and amelioration of conditions associated with excess fat cell mass and obesity are also provided.

According to one aspect, the present invention provides a nucleic acid construct for inhibiting or reducing the expression of platelet-type 12-LO specifically in an adipose cell, the construct comprising at least one nucleic acid sequence encoding a platelet-type 12-LO expression-inhibiting oligonucleic acid, wherein the nucleic acid sequence is operably linked to at least one adipose-specific transcription regulating sequence.

Expression-Inhibiting Oligonucleic Acids

The present invention provides in one aspect a nucleic acid construct comprising at least one adipose-specific transcription regulating sequence operably linked to at least one nucleic acid sequence, wherein the nucleic acid sequence encodes an oligonucleic acid that inhibits or reduces the expression of platelet-type 12-lipoxigenase (12-LO) when expressed in a mammalian target cell.

In one embodiment, the oligonucleic acid comprises at least one nucleic acid sequence substantially complementary to at least a part of the platelet-type 12-LO gene or transcript thereof.

In another embodiment, said oligonucleic acid is selected from the group consisting of: an antisense molecule, a RNA interference (RNAi) molecule and an enzymatic nucleic acid molecule.

The terms "oligonucleotide" and "oligonucleic acid" are used interchangeably and refer to an oligomer or polymer of ribonucleic acid (ribo-oligonucleotide or ribo-oligonucleoside) or deoxyribonucleic acid. These terms include nucleic acid strands composed of naturally occurring nucleobases, sugars and covalent intersugar linkages as well as oligonucleotides having non-naturally occurring portions which function similarly. Such modified or substituted oligonucleotides may be preferred over native forms because of the valuable characteristics including, for example, increased stability in the presence of plasma nucleases and enhanced cellular uptake.

The terms "expression-inhibiting oligonucleic acid", "expression-inhibiting oligonucleotide" or "oligonucleic acid that inhibits or reduces expression" as used herein, denote an oligonucleic acid capable of specifically reducing the expression of the gene products, i.e. the level of mRNA encoding the protein and/or the level of the protein, below the level that is observed in the absence of the oligonucleic acid. In certain embodiments, expression inhibition may be determined by measuring the activity of the protein, e.g., in the case of platelet-type 12-LO, by measuring the level of its enzymatic product 12-HETE. In some embodiments gene expression is down-regulated by at least 25%, preferably at least 50%, at least 70%, 80% or at least 90%. In certain other embodiments, partial down-regulation is preferred. Examples for expression-inhibiting (down-regulating or silencing) oligonucleic acids are antisense molecules, RNA interfering molecules (RNAi), and enzymatic nucleic acid molecules, as detailed herein.

Depending on the nature of the inhibitory oligonucleic acid, the length of the molecule may vary between short oligonucleic acids of about 20 nucleic acid residues or base pairs to longer polynucleic acids as long as thousands of nucleic acid residues, as detailed further below. Typically, the expression-inhibiting oligonucleic acid comprises at least one nucleic acid sequence substantially complementary to one region of the target gene or transcript thereof.

"Complementarity" refers to the ability of a nucleic acid to form hydrogen bond(s) with another nucleic acid sequence. A percent complementarity indicates the percentage of contiguous residues in a nucleic acid molecule, which can form hydrogen bonds (e.g., Watson-Crick base pairing) with a second nucleic acid sequence. "Fully complementary" means that all the contiguous residues of a nucleic acid sequence will hydrogen bond with the same number of contiguous residues in a second nucleic acid sequence. The term "substantially" complementary as used herein refers to a molecule in which about 80% of the contiguous residues of a nucleic acid sequence will hydrogen bond with the same number of contiguous residues in a second nucleic acid sequence. In some embodiments substantially complementary refers to 85%, 90%, 95% of the contiguous residues of a nucleic acid sequence hydrogen bonding with the same number of contiguous residues in a second nucleic acid sequence.

In certain embodiments, the present invention utilizes an "antisense knockout expression" approach, in which a suitable expression-inhibiting oligonucleic acid, as detailed herein, is expressed in the target cell from a recombinant construct encoding the expression-inhibiting oligonucleic acid under an adipose-specific transcription regulating sequence.

Antisense

The present invention provides in another embodiment a nucleic acid construct comprising at least one adipose-specific transcription regulating sequence operably linked to at least one nucleic acid sequence, wherein the nucleic acid sequence encodes an antisense molecule that inhibits or reduces the expression of platelet-type 12-LO. More particularly, the construct expresses the antisense molecule specifically in adipose target cells wherein said expression is effective to enhance the incidence of cell death in the adipose target cells.

Antisense oligonucleotides are nucleic acids that are complementary (or antisense) to the coding strand (sense strand) of the mRNA encoding a particular protein (also known as the negative strand). Although antisense oligonucleic acids are typically RNA based, they can also be DNA based. Additionally, antisense oligonucleotides are often modified to increase their stability. These modifications are known in the art and include, but are not limited to modifying the backbone of the oligonucleotide, modifying the sugar moieties, or modifying the base. Also inclusive in these modifications are various DNA-RNA hybrids or constructs commonly referred to as "gapped" oligonucleotides.

Without being bound by theory, the binding of these antisense molecules to the mRNA is believed to induce stretches of double stranded RNA that trigger degradation of the messages by endogenous RNAses. Alternatively, ribosomes, which are in the process of making the protein from the RNA, are blocked from progressing as they cannot move along the regions of double stranded RNA that are formed. Additionally, sometimes the oligonucleotides are specifically designed to bind near the promoter of the message, and under these circumstances, the antisense oligonucleotides may additionally interfere with translation of the message.

Regardless of the specific mechanism by which antisense oligonucleotides function, their administration to a cell or tissue allows the degradation of the mRNA encoding a specific protein or prevention of its translation. Accordingly, antisense molecules decrease the expression and/or activity of a particular protein.

To design an antisense oligonucleic acid that specifically binds to and mediates the degradation of a particular protein, it is important that the sequence recognized by the oligonucleic acid is unique or substantially unique to that particular protein. For example, sequences that are frequently repeated across protein may not be an ideal choice for the design of an oligonucleic acid that specifically recognizes and degrades a particular message. One skilled in the art can design an oligonucleic acid, and compare the sequence of that oligonucleic acid to nucleic acid sequences that are deposited in publicly available databases to confirm that the sequence is specific or substantially specific for a particular protein.

In another example, it may be desirable to design an antisense molecule that binds to and mediates the degradation of more than one message. In one example, the messages may encode natural allelic variants of platelet-type 12-LO that are expressed in adipose cells.

Methods of producing antisense oligonucleotides may be found for example, in U.S. Pat. Nos. 7,022,832; 6,972,171; 6,277,981 and US Patent Application Publication No. 20050261485.

Thus, in particular embodiments, the antisense molecule may be selected from the group consisting of: a) a DNA antisense molecule; b) a RNA antisense molecule; c) a triplex forming molecule (see below); and d) analogs of a) or b) or c), wherein the oligonucleic acid comprises a sequence substantially complementary to at least a part of a platelet-type 12-LO transcript. In a further particular embodiment, the antisense molecule is an RNA antisense molecule.

An encoded antisense molecule according to the invention may be as short as about 20 nucleotides in length, however longer sequences are preferred. In one embodiment, the antisense molecule is at least 25, preferably at least 30, and more preferably at least 100 nucleotides in length. In certain other embodiments, longer sequences of about 1000 nucleotides or more are preferred (e.g. a molecule substantially complementary to a full-length platelet-type 12-LO transcript). An encoded platelet-type 12-LO antisense molecule is typically about 100-2500 bases in length.

The sequence of an encoded antisense molecule of the invention is selected such that it comprises at least one nucleic acid sequence substantially complementary to at least one target sequence of a platelet-type 12-LO transcript. Preferably, said encoded antisense molecule comprises at least one sequence that is fully complementary to a target sequence of about 20 to about 30 nucleotides of a platelet-type 12-LO transcript. More preferably, said encoded antisense molecule comprises at least two sequences that are fully complementary to a target sequence of about 20 to about 30 nucleotides of the transcript.

In various embodiments, the encoded antisense molecule comprises at least one sequence substantially complementary to at least one target sequence of a platelet-type 12-LO transcript, including platelet-type 12-LO variants expressed in adipose cells (e.g. the human smooth muscle cell variant).

For example, the following antisense sequences were used in the preparation of the recombinant constructs of the invention:

A) Human Smooth Muscle Cell variant platelet-type 12-Lipoxygenase cDNA "600" sequence (SEQ ID NO: 1; Limor et al., 1999):

```
CATGAGGAGAAGAGGCTGGACTTTGAATGGACACTGAAGGCAGGGTGA

GAAAAAGGCTAGACCTCGAAGTGAAATAAGGGCTGGGAGGGCCAAGAA

TGATGATAGACGGTGAGGGACTGAGGGATCAGCTGATGAGTTAAGCCT

CAATACCTGTCCTAGGGCTCTGGAGATGGCCCTCAAACGTGTTTACAC

CCTCCTGAGCTCCTGGAACTGCCTAGAAGACTTTGATCAGATCTTCTG

GGGCCAGAAGAGTGCCCTGGCTGGTCAGTGGTTTCCCCGAGGTCTCCA

TAATCCCTTAATGGCCCCTCTGGATGACTCATCACACTCCACAGTCCC

CCGTAACTCTTTGCAAGAAAGAGACCTTATCATATCTGGTCAACTCAG

AGAGGCCTTGAGAATGAAAACGCAGAAGCTGGGTTCAGGGAAGGGTTA

TATACCTGAACCCCTGGGGTAGATTTTGGGAGAAGGGATATGCAGGCT

GTGGTACATATATCCTCCTTTCACCGCCCACCAAAGAGAAGTTTCGCC

AGTGCTGGCAGGATGATGAGTTGTTCAGCTA;
```

B) Murine (C57BL6) Platelet-Type 12-lipoxygenase 5'PstI-PstI fragment "mp12Lo" (SEQ ID NO: 2; Gene Bank # MMU04334):

```
CTGCAGTTTGTGAAACTGCACAAACAGCACACAGTTGTGGATGACGCC
TGGTTCTGCAACCTCATCACAGTTCAGGGGCCGGGGACAAGTGCAGAG
GCCGTGTTTCCCTGCTACCGCTGGGTGCAGGGAGAGGGAATCCTGAGC
CTCCCGGAGGGACAAGCCCGCCTGGCAGGAGACAATGCCTTAGATGTC
TTCCAGAAGTATCGAGAAAAGGAACTGAAGGAAAGACAACAGACCTAC
TGCTGGGCCACCTGGAAAGAAGGCTTACCTCAGACAATAGCAGCGGAC
TGTAAGGATGACCTTCCTCCAAATATGAGATTCCATGAGGAGAAGAGA
CTGGACTTTGAATGGACGTTGAAGGCGGGGGTTCTGGAAATGGGCCTC
AAACGTGTTTATACCCTCCTGAGAAGCTGGAACCATCTGGAAGACTTT
GATCAGATCTTCTGGGGCCAGAAGAGTGCCTTGGCCGAGAAGGTTCAC
CAGTGTTGGCAGGAAGATGAACTCTTTGGCTACCAGTTCCTCAATGGC
GCCAACCCCATGCTTTTGAGACGCTCCACCTCTCTGCCCTCCAGACTG
GTACTGCCCTCTGGGATGGAGGAGCTTCAAGCTCAGTTGGAGAAAGAA
CTCAAGAATGGATCCCTGTTTGAAGCTGACTTTATCCTGCTGGATGGA
ATTCCAGCTAATGTGATCCGAGGAGAACCACAGTACCTGGCTGCCCCT
CTTGTCATGCTGAGGATGGACCCCGGTGGGAAGCTGCTACCCATGGCT
ATCCAGATTCAGCCCCTAACCCCAGCTCCCCAGCTCCAACACTGTTC
CTGCCCTCGGATCCTCCACTTGCCTGGCTCTTGGCTAAGATCTGGGTC
CGAAATTCAGATTTCCAACTGCAG;
```

C) Human Platelet-Type 12-Lipoxygenase cDNA (SEQ ID NO: 3; Gene Bank # HSLIPXYG, gi:187170):

```
CGGCTCCCCTCGCCTAAGCTGCTGGGGGCGCCATGGGCCGCTACCGCA
TCCGCGTGGCCACCGGGGCCTGGCTCTTCTCCGGGTCGTACAACCGCG
TGCAGCTTTGGCTGGTCGGGACGCGCGGGGAGGCGGAGCTGGAGCTGC
AGCTGCGGCCGGCGCGGGGCGAGGAGGAGGAGTTTGATCATGACGTTG
CAGAGGACTTGGGGCTCCTGCAGTTCGTGAGGCTGCGCAAGCACCACT
GGCTGGTGGACGACGCGTGGTTCTGCGACCGCATCACGGTGCAGGGCC
CTGGAGCCTGCGCGAGGTGGCCTTCCCGTGCTACCGCTGGGTGCAGG
GCGAGGACATCCTGAGCCTGCCCGAGGGCACCGCCCGCCTGCCAGGAG
ACAATGCTTTGGACATGTTCCAGAAGCATCGAGAGAAGGAACTGAAAG
ACAGACAGCAGATCTACTGCTGGGCACCTGGAAGGAAGGGTTACCCC
TGACCATCGCTGCAGACCGTAAGGATGATCTACCTCCAAATATGAGAT
TCCATGAGGAGAAGAGGCTGGACTTTGAATGGACACTGAAGGCAGGGG
CTCTGGAGATGGCCCTCAAACGTGTTTACACCCTCCTGAGCTCCTGGA
ACTGCCTAGAAGACTTTGATCAGATCTTCTGGGGCCAGAAGAGTGCCC
TGGCTGAGAAGGTTCGCCAGTGCTGGCAGGATGATGAGTTGTTCAGCT
ACCAGTTCCTCAATGGTGCCAACCCCATGCTGTTGAGACGCTCGACCT
CTCTGCCCTCCAGGCTAGTGCTGCCCTCAGGGATGGAAGAGCTTCGGG
CTCAACTGGAGAAAGAACTTCAGAATGGTTCCCTGTTTGAAGCTGACT
TCATCCTTCTGGATGGAATTCCAGCCAACGTGATCCGAGGAGAGAAGC
AATACCTGGCTGCCCCCCTCGTTATGCTGAAGATGGAGCCCAATGGGA
AGCTGCAGCCCATGGTCATCCAGATTCAGCCTCCCAACCCCAGCTCTC
CAACCCCAACACTGTTCCTGCCCTCAGACCCCCCACTTGCCTGGCTCC
TGGCAAAGTCCTGGGTCCGAAATTCAGATTTCCAACTGCACGAGATCC
AGTATCACTTGCTGAACACGCACCTGGTGGCTGAGGTCATCGCTGTCG
CCACCATGCGGTGCCTCCCAGGACTGCACCCCATCTTCAAGTTCCTGA
TCCCCCATATCCGCTACACCCATGGAAATCAACACCCGGGCCCGGACC
CAACTCATCTCAGATGGAGGAATTTTTGATAAGGCAGTGAGCACAGGT
GGAGGGGGCCATGTACAGTTGCTCCGTCGGGCGGCAGCTCAGCTGACC
TACTGCTCCCTCTGTCCTCCTGACGACCTGGCTGACCGGGGCCTGCTG
GGACTCCCAGGTGCTCTCTATGCCCATGATGCTTTACGGCTCTGGGAG
ATCATTGCCAGGTATGTGGAGGGGATCGTCCACCTCTTCTACCAAAGG
GATGACATAGTGAAGGGGGACCCTGAGCTGCAGGCCTGGTGTCGGGAG
ATCACGGAGGTGGGGCTGTGCCAGGCCCAGGACCGAGGTTTCCCTGTC
TCCTTCCAGTCCCAGAGTCAACTCTGCCATTTCCTCACCATGTGCGTC
TTCACGTGCACTGCCCAGCATGCCGCCATCAACCAGGGCCAGCTGGAC
TGGTATGCCTGGGTCCCTAATGCTCCATGCACAATGCGGATGCCCCCA
CCCACCACCAAGGAAGATGTGACGATGGCCACAGTGATGGGGTCACTA
CCTGATGTCCGGCAGGCCTGTCTTCAAATGGCCATCTCATGGCATCTG
AGTCGCCGCCAGCCAGACATGGTGCCTCTGGGGCACCACAAAGAAAAA
TATTTCTCAGGCCCCAAGCCCAAAGCTGTGCTAAACCAATTCCGAACA
GATTTGGAAAAGCTGGAAAAGGAGATTACAGCCCGGAATGAGCAACTT
GACTGGCCCTATGAATATCTGAAGCCCAGCTGCATAGAGAACAGTGTC
ACCATCTGAGCCCTAGAGTGACTCTACCTGCAAGATTTCACATCAGCT
TTAGGACTGACATTTCTATCTTGAATTTCATGCTTTCCTAAAGTCTCT
GCTGCTAAGGCTCTATTTCCTCCCCCAGTTAAACCCCCTACATTAGTA
TCCCACTAGCCCAGGGGAGCAGTAAACTTTCTCTGCAAAGACTAGATC
CTTTTTTACGCTTTGCAGACCGCATAGTCACTGTCTCAACTACTCAGC
TCTCCTGCTGCAGCATGAAGGCAGCCACAGACAACATGGAAATGAGTG
TGACTATGTTCCAATAAAACTTTATGGACAC.
```

The resulting nucleic acid constructs encoding exemplary antisense molecules according to the invention and preparation thereof are described in Examples 2 and 8-12 and FIGS. 2, 16-18, 21, 24 and 27.

In various embodiments, encoded oligonucleic acids of the invention have a nucleic acid sequence as set forth in any one of SEQ ID NOS: 1, 2, and 3. In a particular embodiment, the encoded oligonucleic acid is selected from the group of nucleic acid sequences set forth in any one of SEQ ID NOS: 1-3. In one embodiment, the invention provides a recombinant nucleic acid construct that expresses in an adipose target cell an oligonucleic acid as set forth in SEQ ID NO: 1. In another embodiment, the invention provides a recombinant nucleic acid construct that expresses in an adipose target cell an oligonucleic acid as set forth in SEQ ID NO: 2. In another embodiment, the invention provides a recombinant nucleic acid construct that expresses in an adipose target cell an oligonucleic acid as set forth in SEQ ID NO: 3. Each possibility represents a separate embodiment of the present invention.

In other embodiments, the encoded oligonucleic acids of the invention contain analogs, variants and fragments of SEQ ID NOs: 1-3 retaining at least one sequence that is fully complementary to a target sequence of about 20 to about 30 nucleotides of the platelet-type 12-LO transcript. For example, in another embodiment the encoded oligonucleic acid is at least 60% homologous to a sequence selected from the group consisting of SEQ ID NOs: 1-3. In another embodiment, the encoded oligonucleic acid is at least 70% homologous to a sequence selected from the group consisting of SEQ ID NOs: 1-3. In another embodiment, the encoded oligonucleic acid is at least 80% homologous to a sequence selected from the group consisting of SEQ ID NOs: 1-3. In another embodiment, the encoded oligonucleic acid is at least 90% homologous to a sequence selected from the group consisting of SEQ ID NOs: 1-3. In another embodiment, the encoded oligonucleic acid is at least 92% homologous to a sequence selected from the group consisting of SEQ ID NOs: 1-3. In another embodiment, the encoded oligonucleic acid is at least 94% homologous to a sequence selected from the group consisting of SEQ ID NOs: 1-3. In another embodiment, the encoded oligonucleic acid is at least 95% homologous to a sequence selected from the group consisting of SEQ ID NOs: 1-3. In another embodiment, the encoded oligonucleic acid is at least 96% homologous to a sequence selected from the group consisting of SEQ ID NOs: 1-3. In another embodiment, the encoded oligonucleic acid is at least 97% homologous to a sequence selected from the group consisting of SEQ ID NOs: 1-3. In another embodiment, the encoded oligonucleic acid is at least 98% homologous to a sequence selected from the group consisting of SEQ ID NOs: 1-3. In another embodiment, the encoded oligonucleic acid is at least 99% homologous to a sequence selected from the group consisting of SEQ ID NOs: 1-3. In another embodiment, the encoded oligonucleic acid is over 99% homologous to a sequence selected from the group consisting of SEQ ID NOs: 1-3. Each possibility represents a separate embodiment of the present invention.

Another particular antisense molecules includes oligonucleic acids that bind to double-stranded or duplex nucleic acids (e.g., in a folded region of the target RNA or in the target gene), forming a triple helix-containing, or "triplex" nucleic acid. Triple helix formation results in inhibition of gene expression by, for example, preventing transcription of the gene, thereby reducing or eliminating its activity in a cell. Without intending to be bound by any particular mechanism, it is believed that triple helix pairing compromises the ability of the double helix to open sufficiently for the binding of polymerases, transcription factors, or regulatory molecules to occur.

Triplex oligo- and polynucleotides are constructed using the base-pairing rules of triple helix formation (see, e.g., Rigas et al., 1986, Proc. Natl. Acad. Sci. U.S.A. 83:9591) and the target gene mRNA and/or gene sequence. Typically, the triplex-forming oligonucleotides of the invention comprise a specific sequence of from about 10 to at least about 25 nucleotides or longer complementary to a specific sequence in the target RNA or gene (i.e., large enough to form a stable triple helix, but small enough, depending on the mode of delivery, to administer in vivo, if desired). For example, oligonucleotides are designed to bind specifically to the regulatory regions of the target gene (e.g., the 5'-flanking sequence, promoters, and enhancers) or to the transcription initiation site (e.g., between −10 and +10 from the transcription initiation site or translation start site, e.g., at a methionine residue).

RNA Interfering Molecules

In a particular embodiment, said oligonucleic acid is selected from small interfering RNAs (siRNAs) and hairpin RNAs.

The present invention provides other agents that can inhibit or reduce expression of platelet-type 12-LO. One such agent is RNA interfering molecules (RNAi). Without being bound by theory, RNAi appears to involve mRNA degradation, however the biochemical mechanisms are currently an active area of research.

RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner.

The term "RNAi molecule" or "RNAi oligonucleotide" refers to single- or double-stranded RNA molecules having a total of about 15 to about 100 bases, preferably from about 30 to about 60 bases and comprises both a sense and antisense sequence. For example the RNA interference molecule can be a double-stranded polynucleotide molecule comprising self-complementary sense and antisense regions, wherein the antisense region comprises complementarity to a target nucleic acid molecule. Alternatively the RNAi molecule can be a single-stranded hairpin polynucleotide having self-complementary sense and antisense regions, wherein the antisense region comprises complementarity to a target nucleic acid molecule or it can be a circular single-stranded polynucleotide having two or more loop structures and a stem comprising self-complementary sense and antisense regions, wherein the antisense region comprises complementarity to a target nucleic acid molecule, and wherein the circular polynucleotide can be processed either in vivo or in vitro to generate an active molecule capable of mediating RNAi.

As used herein, the term "RNAi" is a generic term used throughout the specification to include small interfering RNAs (siRNAs), hairpin RNAs, and other RNA species that can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts that can produce siRNAs in vivo.

In certain embodiments, the subject RNAi constructs are "small interfering RNAs" or "siRNAs". These nucleic acids are around 19-30 nucleotides in length, and even more preferably 21-23 nucleotides in length, e.g., corresponding in length to the fragments generated by nuclease "dicing" of longer double-stranded RNAs.

Small Inhibitory RNAs (siRNA) have been emerging as a viable alternative to antisense oligonucleotides since lower concentrations are required to achieve levels of suppression that are equivalent or superior to those achieved with antisense oligonucleotides. Long double-stranded RNAs have been used to silence the expression of specific genes in a variety of organisms such as plants, nematodes, and fruit flies. An RNase-III family enzyme called Dicer processes these long double stranded RNAs into 21-23 nucleotide small interfering RNAs which are then incorporated into an RNA-induced silencing complex (RISC). Unwinding of the siRNA activates RISC and allows the single-stranded siRNA to guide the complex to the endogenous mRNA by base pairing. Recognition of the endogenous mRNA by RISC results in its cleavage and consequently makes it unavailable for translation. In certain embodiments of the present invention, introduction of long double stranded RNA into mammalian cells results in a potent antiviral response that can be bypassed by use of siRNAs.

The siRNAs are understood to recruit nuclease complexes and guide the complexes to the target mRNA by pairing to the specific sequences. As a result, the target mRNA is degraded by the nucleases in the protein complex.

The encoded siRNA molecules of the invention comprise sense and antisense strands having nucleic acid sequence complementarity, wherein each strand is typically about 18-30 nucleotides in length.

In some embodiments, the sense and antisense strands of the present siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

Preferably, one or both strands of the siRNA of the invention can also comprise a 3' overhang. As used herein, a "3' overhang" refers to at least one unpaired nucleotide extending from the 3'-end of an RNA strand. Thus in one embodiment, the siRNA of the invention comprises at least one 3' overhang of from 1 to about 6 nucleotides in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA of the invention can comprise 3' overhangs of dithymidylic acid ("TT") or diuridylic acid ("UU").

For example, without limitation, synthesis of RNAi molecules suitable for use with the present invention can be effected as follows. First, the 12-LO nucleic acid sequence target is optionally scanned downstream for AA dinucleotide sequences. Occurrence of each AA and the 3' adjacent 19 nucleotides is recorded as potential siRNA target sites.

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites that exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene. An encoded siRNA agent of the present invention are of at least 10, at least 15, at least 17 or at least 19 bases specifically hybridizable with a platelet-type 12-LO mRNA.

The phrase "specifically hybridizable" as used herein indicates a sufficient degree of complementarity such that stable and specific binding occurs between the target and the oligonucleotide. A nucleic acid sequence specifically hybridizable with a platelet-type 12-LO mRNA has a preference for hybridizing (in cells, under physiological conditions) with a platelet-type 12-LO mRNA as opposed to a non-related RNA molecule (e.g. GAPDH). Preferably, said sequence has at least a 5-fold preference for hybridizing with a 12-LO mRNA as opposed to a non-related RNA molecule. Thus, a siRNA specifically hybridizable with a platelet-type 12-LO mRNA has sufficient complementarity to an RNA product of a platelet-type 12-LO gene for the siRNA molecule to direct cleavage of said RNA via RNA interference.

Guidelines for the selection of highly effective siRNA sequences for mammalian RNA may be found, inter alia, in US Patent Application Publication No. 20060078902. RNAi molecules and methods for producing RNAi oligonucleotides can be found for example in US Patent Application Publication Nos. 20050100907, 20020137210 and the like.

Enzymatic Nucleic Acid Sequences

The terms "enzymatic nucleic acid molecule" or "enzymatic oligonucleic acid" refers to a nucleic acid molecule which has complementarity in a substrate binding region to a specified gene target, and also has an enzymatic activity which is active to specifically cleave target RNA, thereby silencing the target gene. The complementary regions allow sufficient hybridization of the enzymatic nucleic acid molecule to the target RNA and subsequent cleavage. The term enzymatic nucleic acid is used interchangeably with for example, ribozymes, catalytic RNA, enzymatic RNA, catalytic DNA, aptazyme or aptamer-binding ribozyme, catalytic oligonucleotide, nucleozyme, DNAzyme, RNAenzyme.

The possibility of designing ribozymes to cleave any specific target RNA has rendered them valuable tools in both basic research and therapeutic applications. In therapeutics, ribozymes have been exploited to target viral RNAs in infectious diseases, dominant oncogenes in cancers, and specific somatic mutations in genetic disorders Ribozymes and ribozyme analogs are described, for example, in U.S. Pat. Nos. 5,436,330; 5,545,729 and 5,631,115.

While ribozymes that cleave mRNA at site-specific recognition sequences can be used to destroy particular mRNAs, other ribozymes include hammerhead ribozymes. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art, see for example WO 2004/041197.

Ribozymes also include RNA endoribonucleases (hereinafter "Cech-type ribozymes") such as the one which occurs naturally in 25 Tetrahymena thermophila (known as the IVS, or L-19 IVS RNA) and which has been extensively described by Thomas Cech and collaborators (see e.g. published International patent application No. WO88/04300).

The Cech-type ribozymes have an eight base pair active site that hybridizes to a target RNA sequence "hereafter cleavage of the target RNA takes place. The invention encompasses those Cech-type ribozymes that target eight base-pair active site sequences.

Because ribozymes, unlike antisense molecules, are catalytic, a lower intracellular concentration is required for efficiency.

Another agent capable of silencing a target gene is a DNAzyme molecule, which is capable of specifically cleaving an mRNA transcript or a DNA sequence of a target gene.

DNAzymes are single-stranded polynucleotides that are capable of cleaving both single- and double-stranded target sequences. Examples of construction and amplification of synthetic, engineered DNAzymes recognizing single- and double-stranded target cleavage sites are disclosed in U.S. Pat. No. 6,326,174.

There are currently two basic types of DNA enzymes, and both of these were identified by Santoro and Joyce (see, for example, U.S. Pat. No. 6,110,462). The 10-23 DNA enzyme comprises a loop structure that connects two arms. The two arms provide specificity by recognizing the particular target nucleic acid sequence while the loop structure: provides catalytic function under physiological conditions.

Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence.

When synthesizing the DNA enzyme, the specific antisense recognition sequence that will target the enzyme to the message is divided so that it comprises the two arms of the DNA enzyme, and the DNA enzyme loop is placed between the two specific arms.

Constructs, Promoters and Vectors

The term "construct" as used herein includes a nucleic acid sequence encoding an expression-inhibiting oligonucleic acid according to the present invention, the nucleic acid sequence operably linked to a promoter and optionally other transcription regulation sequences.

The constructs of the present invention may be produced using standard recombinant and synthetic methods well known in the art. An isolated nucleic acid sequence can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis (see e.g. Sambrook et al., 1989). Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional polypeptide or peptide of the invention.

A nucleic acid molecule homolog can be produced using a number of methods known to those skilled in the art (see, for example, Sambrook et al., 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. For example, nucleic acid molecule homologs can be selected from a mixture of modified nucleic acids by screening for the function of the oligonucleic acid encoded by the nucleic acid with respect to fat cell viability, for example by the methods described herein.

The phrase "operably linked" refers to linking a nucleic acid sequence to a transcription control sequence in a manner such that the molecule is able to be expressed when transfected (i.e., transformed, transduced, infected or transfected) into a host cell. Transcription control sequences are sequences, which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Exemplary suitable transcription control sequences include those that function in animal, bacteria, helminth, yeast and insect cells. In certain preferable embodiments, transcription control sequences include mammalian transcription control sequences, preferably human regulatory sequences.

The term "promoter" as used herein includes, but is not limited to, a region starting just downstream of the transcription initiation point (+1) and including a region located 20-30 base pairs upstream thereto, which includes a TATA box or a TATA box-like region (e.g. Sp1 boxes instead of, or in addition to, the TATA box) responsible for directing RNA polymerase to start transcription at a correct position. In addition to this region, a promoter may include regions that are required for proteins other than RNA polymerase (e.g. C/EBP, Sp1) to associate with for adjusting expression, and thus may, in some embodiments, include hundreds of base pairs upstream to the transcription initiation point. The promoter also includes the start-site of transcription.

In another aspect, the present invention provides a recombinant nucleic acid construct for inhibiting or reducing the expression of platelet-type 12-LO specifically in an adipose cell, the construct comprising at least one nucleic acid sequence encoding a platelet-type 12-LO expression-inhibiting oligonucleic acid, wherein the nucleic acid sequence is operably linked to an adipose-specific transcription regulating sequence.

According to various embodiments, the adipose-specific transcription regulating sequence may be any regulatory sequence (e.g. promoters and enhancers) that induces or enhances expression selectively (or, in other embodiments, preferentially) in adipose cells. As used herein, an adipose-specific transcription regulating sequence relates to both adipocyte-specific promoters and enhancers and pre-adipocyte-specific promoters and enhancers, as well as transcription regulating sequences which induce expression in both adipocytes and pre-adipocytes.

Suitable transcription regulating sequences include, but are not limited to, those regulating the expression of genes such as aP2, lipin, perilipin, S3-12, leptin, adiponectin and others, which are either exclusively expressed in fat cells or whose knockout models show dominant fat tissue phenotypic changes, with little changes in other tissue types.

In a particular embodiment, said transcription regulating sequence induces or enhances gene expression in large-cell adipocytes. Enlarged adipocytes are associated with insulin resistance and are an independent predictor of type 2 diabetes. Large cell adipocyte populations typically contain cells of 100.1±3.94 µm in diameter, while small cell adipocyte populations typically contain cells of 57.6±3.54 µm in diameter (Jernas et al., 2006).

In various particular embodiments, the construct contains at least one transcription regulating sequence selected from: human adiponectin promoter, human adiponectin enhancer, human leptin promoter, human leptin enhancer and combinations thereof. Each possibility represents a separate embodiment of the present invention.

In a currently preferred embodiment, the transcription regulating sequence is human adiponectin promoter/enhancer. In one particular embodiment, the transcription regulating sequence has a nucleic acid sequence corresponding to the minimum human adiponectin promoter/enhancer, as set forth in SEQ ID NO: 4 presented hereinbelow:

```
AAGCTTTAAGAATTCAGGGCCTTTTTAACTTGCCAAGCCCCACACCAC

TCCAGGAACTTCCCCACACCCCAGTTCTCAGAATTCATGTGCAAGGTC

TTTCCTAAATCCAGGGTCCAGGTCAGAGAGTGGAGGATGTGCTCTATT

TCTTACCTGATTGCAGACCCCTCTGACAGTCCTCCCTTCTGAAGCACT

CACTGTCTGAACGTACACAGTCTCAGACTTAATCATGCACAGTGAGCA

AGACTGTGGTGTGATAATTGGCGTCCCTGACTTATTAGGGCAAATCTA

TGGGAGGGGGAGACCTCCTGGACCACTGAGCAATTAATTCATTTACAT

TAGGAAGTTTCTCCGTCAGATGCAGGAAAAAAATCTTGTTTTCCTGCT

GTGGTTTTGACTTTTGCCCCATCTTCTGTTGCTGTTGTAGGAGGCAAA

ATAAGGGTCAAGGCCTGGAAACACAAGTGCTTTGACTGAAGCTCCACT

TGGCTTCCGAAGCCCAAGCTGGGTTGTACCAGGTTCCCTAGGGTGCAG

GCTGTGGGCAACTGCCAGGGACATGTGCCTGCCCACCGGCCTCTGGCC

CTCACTGAGTTGGCCAATGGGAAATGACAATTGTGAGGTGGGGACTGC

CTGCCCCGTGAGTACCAGGCTGTTGAGGCTGGGCCATCTCCTCCTCA

CTTCCATTCTGACTGCAGTCTGTGGTTCTGATTCCATACCAGAGGATC

C.
```

In another currently preferred embodiment, the transcription regulating sequence is human leptin promoter/enhancer. In one particular embodiment, the transcription regulating sequence has a nucleic acid sequence corresponding to the minimum 138 bp human leptin promoter/enhancer, as set forth in SEQ ID NO: 7 presented hereinbelow:

```
GCTAGCAGCCGCCCGGCACGTCGCTACCCTGAGGGGCGGGGCGGGAGC

TGGCGCTAGAAATGCGCCGGGGCCTGCGGGGCAGTTGCGCAAGTTGTG

ATCGGGCCGCTATAAGAGGGGCGGGCAGGCATGGAGCCCCGTA.
```

In various embodiments, the at least one transcription regulating sequence may be a naturally occurring transcription regulating sequence, e.g. a naturally occurring promoter or enhancer, or may be a sequence derived therefrom. The term "derived" refers to the fact that a transcriptional regulatory sequence (for example, a promoter or enhancer) can be the complete native regulatory sequence of the gene, a portion of the native regulatory sequence, a chimeric construction of the native regulatory sequence, a combinatorial construction of one or more native regulatory sequences, or a variant of the native regulatory sequence obtained by, for example, deletion, addition or replacement of at least one nucleotide. A variant regulatory sequence can comprise modified nucleotides. The derived sequence preferably demonstrates properties of control/regulation (e.g., increase) of the expression of coding sequences operably linked thereto.

In another embodiment, the construct contains a plurality of adipose-specific transcription regulating sequences (e.g. a plurality of enhancer elements) operably linked to the nucleic acid sequence encoding the platelet-type 12-LO expression-inhibiting oligonucleic acid.

In another embodiment, the construct contains at least one sequence selected from a C/EBP binding site and an Sp1 binding site operably linked to the nucleic acid sequence encoding the platelet-type 12-LO expression-inhibiting oligonucleic acid. Without wishing to be bound by any theory or mechanism of action, an Sp1 site adjacent to both gene promoter/enhancer C/EBP sites allows increased and more specific knockdown of Human platelet-type 12-LO in the large-cell adipocytes mediated by the stimulatory C/EBP transcription factor.

In another embodiment, the transcription regulating sequence is a novel recombinant chimeric promoter/enhancer having a nucleic acid sequence as set forth in SEQ ID NO: 8 (see also FIG. 19), as follows:

```
GCTAGCAGCCGCCCGGCACGTCGCTACCCTGAGGGGCGGGGCGGGAGC

TGGCGCTAGAAATGCGCCGGGGCCTGCGGGGCAGTTGCGCAAGTTGTG

ATCGGGATCCACTAGTCCAGTGTGGTGGAATTCTGCAGATATCCAGCA

CAGTGGCGGCCGCTCGAGTCTAGAAAGCTTTAAGAATTCAGGGCCTTT

TTAACTTGCCAAGCCCCACACCACTCCAGGAACTTCCCCACACCCCAG

TTCTCAGAATTCATGTGCAAGGTCTTTCCTAAATCCAGGGTCCAGGTC

AGAGAGTGGAGGATGTGCTCTATTTCTTACCTGATTGCAGACCCCTCT

GACAGTGCTCCCTTCTGAAGCACTCACTGTCTGAACGTACACAGTCTC

AGACTTAATCATGCACAGTGAGCAAGACTGTGGTGTGATAATTGGCGT

CCCTGACTTATTAGGGCAAATCTATGGGAGGGGGAGACCTCCTGGACC

ACTGAGCAATTAATTCATTTACATTAGGAAGTTTCTCCGTCAGATGCA

GGAAAAAAATCTTGTTTTCCTGCTGTGGTTTTGATTTTGCCCCATCTT

CTGTTGCTGTTGTAGGAGGCAAAATAAGGGTCAAGGCCTGGAAACACA

AGTGCTTTGACTGAAGCTCCACTTGGCTTCCGAAGCCCAAGCTGGGTT

GTACCAGGTTCCCTAGGGTGCAGGCTGTGGGCAACTGCCAGGGACATG

TGCCTGCCCACCGGCCTCTGGCCCTCACTGAGTTGGCCAATGGGAAAT

GACAATTGTGAGGTGGGGACTGCCTGCCCCCGTGAGTACCAGGCTGTT

GAGGCTGGGCCACCTCCTCCTCACTTCCATTCTGACTGCAGTCTGTGG

TTCTGATTCCATACCAGAGG
```

In another embodiment, the transcription regulating sequence is a novel recombinant promoter/enhancer having a nucleic acid sequence as set forth in SEQ ID NO: 9 (see also FIGS. 18 and 25), as follows:

```
GCTAGCAGCCGCCCGGCACGTCGCTACCCTGAGGGGCGGGGCGGGAGC

TGGCGCTAGAAATGCGCCGGGGCCTGCGGGGCAGTTGCGCAAGTTGTG

ATCGGGATCCACTAGTCCAGTGTGGTGGAATTCTGCAGATATCCAGCA

CAGTGGCGGCCGCTCGAGTCTAGAGCTAGCAGCCGCCCGGCACGTCGC

TACCCTGAGGGGCGGGGCGGGAGCTGGCGCTAGAAATGCGCCGGGGCC

TGCGGGGCAGTTGCGCAAGTTGTGATCGGGCCGCTATAAGAGGGGCGG

GCAGGCATGGAGCCCCGTAGGATCC
```

For example, in other embodiments the transcription regulating sequence is at least 60%, at least 70%, at least 80%, at least 90%, at least 92%, at least 94%, at least 95%, at least 96%, at least 97%, at least 98% or at least 99% homologous to a sequence selected from the group consisting of SEQ ID NOs: 4, and 7-9, retaining the ability to facilitate gene expression specifically or preferentially in an adipose cell. Each possibility represents a separate embodiment of the present invention.

In another embodiment, there are provided vectors comprising the constructs of the invention. The invention thus provides a vector comprising a recombinant nucleic acid construct for inhibiting or reducing the expression of platelet-type 12-LO specifically in an adipose cell, the construct comprising at least one nucleic acid sequence encoding a platelet-type 12-LO expression-inhibiting oligonucleic acid, wherein the nucleic acid sequence is operably linked to at least one adipose-specific transcription regulating sequence.

In some embodiments, such vectors may be used for delivering and expressing the desired oligonucleic acid in the target cell, and/or for replicating the constructs of the invention in vitro. In certain embodiments, vectors can be plasmid, viral, or others known in the art, used for replication and expression in mammalian cells. Any type of plasmid, cosmid, YAC or viral vector can be used to prepare the recombinant DNA construct that can be introduced directly into the tissue site. Alternatively, viral vectors can be used which selectively infect the desired tissue, advantageous also for administration by another route (e.g., systematically).

The type of vector is selected according to the desired modulating oligonucleic acid to be produced—e.g. for producing single-stranded or double-stranded RNA or DNA. Suitable vectors for producing various expression-regulating oligonucleic acids are known in the art. For example, RNAi expression vectors (also referred to as a dsRNA-encoding plasmid) are replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

In other embodiments, the invention contemplates host cells comprising these vectors. Various suitable prokaryotic and eukaryotic host cells with suitable expression vectors are known in the art, including, but not limited to animal cells (including mammalian cells, e.g. human cells), bacterial cells, plant cells, yeast cells and insect cells.

In another embodiment, the invention provides vectors which selectively express the desired oligonucleic acids in fat cells. For example, viral-based vectors may be used to construct such suitable vectors for in vivo expression. In certain embodiments, suitable viral-based vectors are those which are 1) safe for human use; 2) easy to use; 3) constructed to express the desired inhibitor in human fat tissue; 4) not able to reproduce (replicate) in the subject; 5) constructed to expresses the transgene strongly initially; and 6) having a controlled life cycle in the subject. Suitable viral systems which can be used for constructing the viral-based adipose-specific vectors of the invention are known in the art, e.g. Gutless or mutant adeno-associated virus (AAV), adenovirus, retrovirus or lentivirus vectors. In a particular embodiment, the vector is an AAV-based vector.

Figure 27:
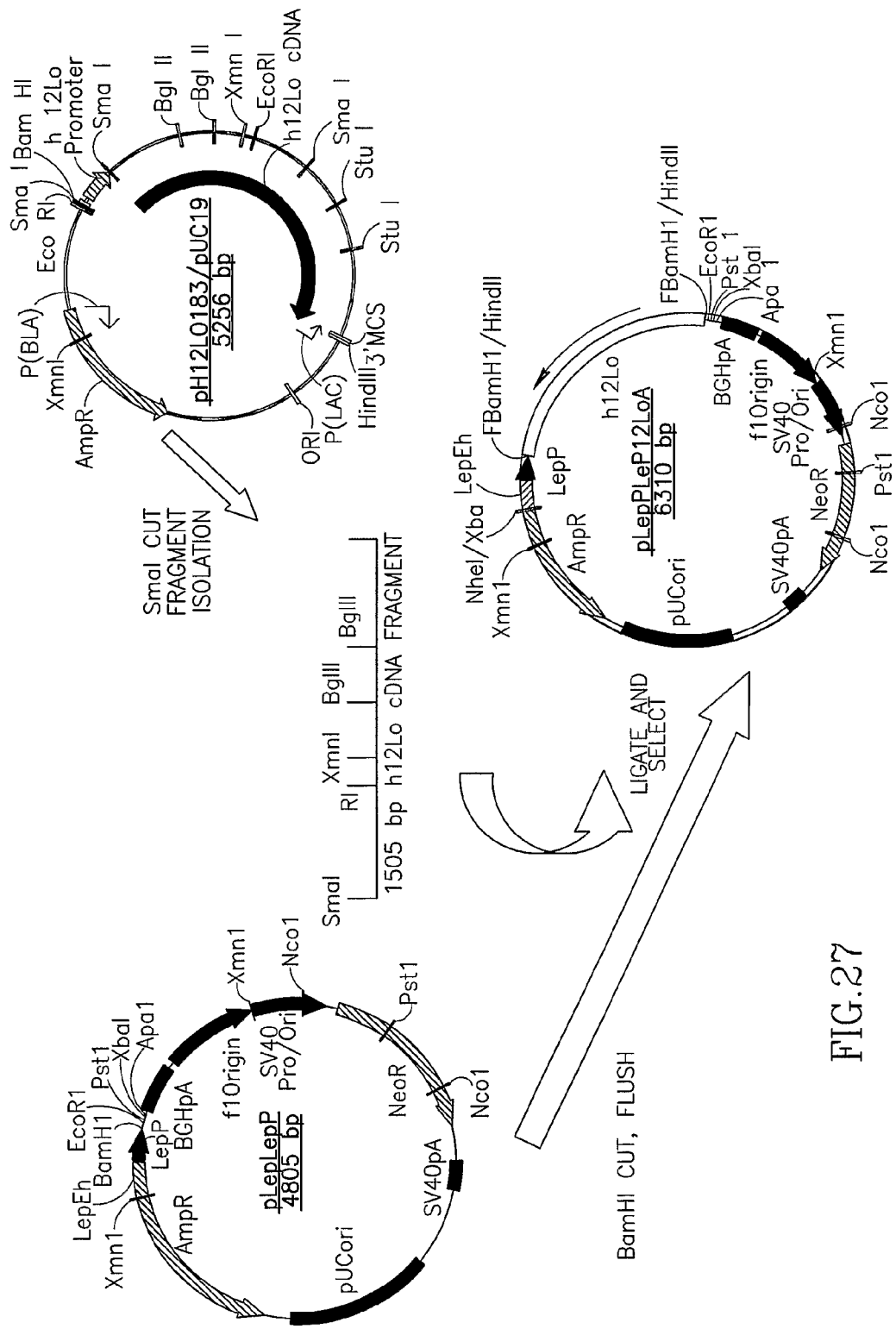
FIG. 27 illustrates construction of the Double Enhancer, Single Leptin Promoter driven Human 12-Lipoxygenase knockout Vector.

An exemplary viral vector for adipose-specific platelet-type 12-LO antisense knockout is pAAVAdi-12LO-A (see FIG. 17 and Example 9); exemplary plasmid vectors for adipose-specific platelet-type 12-LO antisense knockout are pUCAdi-h12LoA-pA (see FIGS. 16 and 18 and Example 8), pLepEnhAdipPr12LoA (FIG. 21) pLepp12LoA (FIG. 24) and pLepLepP12LoA (FIG. 27). In yet another particular embodiment, the vector is a retroviral vector, e.g. vectors based on the Molony Murine Leukemia Virus (MoMLV), which have been well characterized and used safely in humans.

Pharmaceutical Compositions

In another aspect, the present invention provides pharmaceutical compositions comprising the constructs of the invention. Thus, the invention provides a pharmaceutical composition comprising a recombinant nucleic acid construct comprising at least one adipose-specific transcription regulating sequence operably linked to at least one nucleic acid sequence, wherein the at least one nucleic acid sequence encodes an oligonucleic acid comprising at least one sequence substantially complementary to at least a part of the platelet-type lipoxygenase (platelet-type 12-LO) gene or transcript thereof, and wherein the oligonucleic acid inhibits or reduces the expression of platelet-type 12-LO, and a pharmaceutically acceptable carrier, excipient and/or diluent.

As used herein, a "pharmaceutical composition" refers to a preparation of one or more of the active ingredients described herein, e.g. a construct encoding an antisense molecule, an RNAi molecule or an enzymatic nucleic acid, with other components such as physiologically suitable carriers and excipients. The purpose of a pharmaceutical composition is to facilitate administration of a compound to a subject.

Hereinafter, the phrases "therapeutically acceptable carrier" and "pharmaceutically acceptable carrier", which may be used interchangeably, refer to a carrier or a diluent that does not cause significant irritation to an organism and does not abrogate the biological activity and properties of the administered compound.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

In another embodiment of the present invention, a therapeutic composition further comprises a pharmaceutically acceptable carrier. As used herein, a "carrier" refers to any substance suitable as a vehicle for delivering a nucleic acid molecule of the present invention to a suitable in vivo or in vitro site. As such, carriers can act as a pharmaceutically acceptable excipient of a therapeutic composition containing a nucleic acid molecule of the present invention. Preferred carriers are capable of maintaining a nucleic acid molecule of the present invention in a form that, upon arrival of the nucleic acid molecule to a cell, the nucleic acid molecule is capable of entering the cell and being expressed by the cell. Carriers of the present invention include: (1) excipients or formularies that transport, but do not specifically target a nucleic acid molecule to a cell (referred to herein as non-targeting carriers); and (2) excipients or formularies that deliver a nucleic acid molecule to a specific site in a subject or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to a subject, for example, esters or partial esters of fatty acids containing from about six to about twenty-two carbon atoms. Examples of esters include, caproic, octanoic, lauric, palmitic, stearic, linoleic, linolenic, olesteric, and oleic acids. Other carriers can include metal particles (e.g., gold particles) for use with, for example, a biolistic gun through the skin. Therapeutic compositions of the present invention can be sterilized by conventional methods.

Targeting carriers are herein referred to as "delivery vehicles". Delivery vehicles of the present invention are capable of delivering a therapeutic composition of the present invention to a target site in a subject. A "target site" refers to a site in a subject to which one desires to deliver a therapeutic composition. Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in a subject, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a target cell can be introduced to the outer surface of a liposome delivery vehicle so as to target the delivery vehicle to the target cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

In certain particular embodiments, a preferred delivery vehicle of the present invention is a liposome. A liposome is capable of remaining stable in a subject for a sufficient amount of time to deliver a nucleic acid molecule of the present invention to a preferred site in the subject. A liposome of the present invention is preferably stable in the subject into which it has been administered for at least about 30 minutes, more preferably for at least about 1 hour and even more preferably for at least about 24 hours.

A liposome of the present invention comprises a lipid composition that is capable of targeting a nucleic acid molecule of the present invention to a particular, or selected, site in a subject. Preferably, the lipid composition of the liposome is capable of targeting to adipose tissue.

Suitable liposomes for use with the present invention include any liposome. Preferred liposomes of the present invention include those liposomes standardly used in, for example, gene delivery methods known to those of skill in the art. In certain embodiments, more preferred liposomes comprise liposomes having a polycationic lipid composition and/or liposomes having a cholesterol backbone conjugated to polyethylene glycol.

Another preferred delivery vehicle comprises a recombinant virus particle. A recombinant virus particle of the present invention includes a therapeutic composition of the present invention, in which the recombinant molecules contained in the composition are packaged in a viral coat that allows entrance of DNA into a cell so that the DNA is expressed in the cell. A number of recombinant virus particles can be used, including, but not limited to, those based on adenoviruses, adeno-associated viruses (AAV), herpesviruses, lentivirus and retroviruses (e.g. MoMLV).

Therapeutic Use

In another aspect, the invention is directed to the use of a construct of the invention for the preparation of a medicament. The present invention provides methods of treating a disease or condition associated with excess adipose tissue and use of a construct comprising at least one nucleic acid sequence encoding a platelet-type 12-LO expression-inhibiting oligonucleic acid, wherein the nucleic acid sequence is operably linked to an adipose-specific transcription regulating sequence, to prepare a medicament useful in the treatment of those diseases or conditions.

Accordingly, in one embodiment the invention relates to methods of treating, preventing, reducing or ameliorating obesity in a subject, the methods comprising administering to the subject an effective amount of an agent that reduces platelet-type 12-LO expression or activity in adipose cells.

In another embodiment, the invention provides methods for treating, preventing or ameliorating an obesity-associated condition or a symptom associated therewith in a subject in need thereof, comprising administering to the subject an effective amount of a therapeutic agent that reduces platelet-type 12-LO expression or activity selectively in adipose cells.

In various particular embodiments, the condition includes, but is not limited to, cardiovascular diseases, type 2 diabetes, hypertension, cancer (e.g. adrenal, pancreatic, prostrate and gastric cancer), osteoarthritis and stroke.

In another embodiment, the invention provides a method for reducing fat cell mass in a subject in need thereof, comprising administering to the subject an effective amount of a therapeutic agent that reduces platelet-type 12-LO expression or activity selectively in fat cells.

In another embodiment, the invention provides a method for inducing apoptosis specifically in a cell selected from the group consisting of adipocytes and pre-adipocytes comprising contacting the cell with a therapeutic agent which reduces platelet-type 12-LO expression or activity. In another embodiment the therapeutic agent is administering to a subject in need thereof in the form of a pharmaceutical composition such that said agent does not substantially induce apoptosis in non-adipose cells.

In another aspect, the invention provides a method for inhibiting or reducing the expression of platelet-type 12-LO in a cell selected from adipocytes and pre-adipocytes, comprising contacting the cell with a therapeutic agent which reduces platelet-type 12-LO expression or activity. In another embodiment the therapeutic agent is administering to a subject in need thereof in the form of a pharmaceutical composition such that said compound does not substantially inhibit the expression of platelet-type 12-LO in non-adipocyte cells.

Agents which reduce platelet-type 12-LO expression or activity include, in some embodiments, antisense molecules, RNA interference (RNAi) molecules and enzymatic nucleic acid molecules directed to platelet-type 12-LO, as detailed herein, and nucleic acid constructs encoding same. Preferably, the agent is a recombinant nucleic acid construct comprising at least one adipose-specific transcription regulating sequence operably linked to at least one nucleic acid sequence, wherein the at least one nucleic acid sequence encodes an oligonucleic acid comprising at least one sequence substantially complementary to at least a part of the platelet-type lipoxygenase (platelet-type 12-LO) gene or transcript thereof, and wherein the oligonucleic acid inhibits or reduces the expression of platelet-type 12-LO.

In another embodiment, said oligonucleic acid is selected from the group consisting of: an antisense molecule, a RNA interference (RNAi) molecule and an enzymatic nucleic acid molecule. In a particular embodiment, said oligonucleic acid is selected from small interfering RNAs (siRNAs) and hairpin RNAs. In another particular embodiment, the antisense molecule is selected from the group consisting of: a DNA antisense molecule; a RNA antisense molecule; a triplex forming molecule; and analogs of a) or b) or c); wherein the oligonucleic acid comprises a sequence substantially complementary to at least a part of a platelet-type 12-LO transcript. In yet another particular embodiment, the antisense molecule is an RNA antisense molecule.

In another embodiment, the oligonucleic acid comprises at least one sequence fully complementary to a target sequence of about 20 to about 30 nucleotides of a platelet-type 12-LO transcript. In yet another embodiment, said oligonucleic acid comprises at least a first sequence fully complementary to a first target sequence of about 20 to about 30 nucleotides of the platelet-type 12-LO transcript, and at least a second sequence fully complementary to a second target sequence of about 20 to about 30 nucleotides of said platelet-type 12-LO transcript.

In a particular embodiment, said oligonucleic acid has a nucleic acid sequence as set forth in any one of SEQ ID NOS: 1, 2, and 3, and analogs and fragments thereof comprising at least one sequence fully complementary to a target sequence of about 20 to about 30 nucleotides of the platelet-type 12-LO transcript.

Optionally, the adipose-specific transcription regulating sequence may be selected from the group consisting of: adipocyte-specific promoters and enhancers; pre-adipocyte-specific promoters and enhancers; and transcription regulating sequences which induce expression in both adipocytes and pre-adipocytes. In another embodiment, said transcription regulating sequence induces or enhances gene expression in large-cell adipocytes.

In a particular embodiment, the construct contains at least one transcription regulating sequence selected from: human adiponectin promoter, human adiponectin enhancer, human leptin promoter, human leptin enhancer and combinations thereof.

For example, the transcription regulating sequence may have a nucleic acid sequence as set forth in any one of SEQ ID NOS: 4 and 7.

In another embodiment, the construct contains a plurality of adipose-specific transcription regulating sequences, e.g. it may contain at least one sequence selected from a C/EBP binding site and an Sp1 binding site. Optionally and preferably, the construct may contain at least one C/EBP binding site and at least one Sp1 binding site.

In another particular embodiment, the construct may contain one or more recombinant or synthetic transcription regulating sequences, e.g. those indicated by any one of SEQ ID NOS: 8 and 9.

In another embodiment, the construct is administered to the subject in the form of a vector which expresses a platelet-type 12-LO expression-inhibiting oligonucleic acid in an adipose target cell. In another embodiment, said vector expresses said oligonucleic acid in large cell adipocytes.

In another embodiment, the construct is administered to the subject in the form of a pharmaceutical composition further comprising a pharmaceutically acceptable carrier, excipient or diluent.

In order to treat a subject with a disease, a pharmaceutical composition of the present invention is administered to the subject in an effective manner such that the composition is capable of treating that subject from disease. According to the present invention, treatment of a disease refers to alleviating a disease and/or associated symptoms and/or preventing the development of a secondary disease resulting from the occurrence of a primary disease. An effective administration protocol (i.e., administering a pharmaceutical composition in an effective manner) comprises suitable dose parameters and modes of administration that result in treatment of a disease. Effective dose parameters and modes of administration can be determined using methods standard in the art for a particular disease. Such methods include, for example, determination of survival rates, side effects (i.e., toxicity) and progression or regression of disease.

In accordance with the present invention, a suitable single dose size is a dose that is capable of treating a subject with disease when administered one or more times over a suitable time period. For example, a suitable single dose size may induce a reduction in excess fat cell mass in a subject in need thereof. Doses of a pharmaceutical composition of the present invention suitable for use with direct injection techniques can be used by one of skill in the art to determine appropriate single dose sizes for systemic administration based on the size of a subject. For example, in some embodiments a suitable dose range of an AAV-based vector comprising a construct of the invention is about $10^6$-$10^9$, preferably $10^8$-$10^9$ CFU/human patient administered systemically, or about $10^6$-$10^7$ CFU/human patient administered locally, e.g. by injection.

In various particular embodiments, the compositions of the invention are administered locally to specific fat depots (e.g., local delivery to subcutaneous depots; mesenteric intraarterial delivery to visceral fat) or systemically, depending on the chosen fat pool. In various other particular embodiments, the pharmaceutical compositions of this invention may be administered by a manner selected from: 1) systemically, e.g. through intravenous, intra-arterial or subcutaneous injection, oral administration or inhalation or any mucosal or other spray; 2) locally, e.g. through direct intra- or peri-tissue delivery through injections, ointment or any other form of disposal; and 3) to specific fat depots e.g. the visceral fat depot through intra-arterial injection (e.g., injection to the mesenteric artery/arterial tree). In other particular embodiments, administration may be repeated as necessary until desirable results are obtained.

For example, overweight or obese human subjects may receive a construct of the invention systemically through intravenous, intramuscular or subcutaneous injections, inhalations or the oral route. Additionally, for obese or viscerally obese individuals, formerly obese/overweight subjects experiencing rapid re-accumulation of fat tissue or weight gain, and type 2 diabetic patients with significant adiposity, regional administration may also be beneficial. Such administration can be achieved through local inoculation of regional fat depots (subcutaneous at the abdominal girth, subscapular, gluteal etc.) through the skin, during surgery directly to exposed fat depots, via laparoscopic techniques to selected fat depots, or through intra-arterial injection using standard catheterization methodology. Suitable administration regimes may readily be determined by the skilled artisan.

In another embodiment, the invention provides a recombinant nucleic acid construct comprising at least one adipose-specific transcription regulating sequence operably linked to at least one nucleic acid sequence, wherein the at least one nucleic acid sequence encodes an oligonucleic acid comprising at least one sequence substantially complementary to at least a part of the platelet-type lipoxygenase (platelet-type 12-LO) gene or transcript thereof, and wherein the oligonucleic acid inhibits or reduces the expression of platelet-type 12-LO, for reducing obesity in a subject in need thereof, for preventing or ameliorating an obesity-associated condition or a symptom associated therewith, for reducing fat cell mass, for inducing apoptosis specifically in a cell selected from the group consisting of adipocytes and pre-adipocytes and/or for inhibiting or reducing the expression of platelet-type 12-LO in a cell selected from adipocytes and pre-adipocytes, as detailed herein.

The following examples are presented in order to more fully illustrate some embodiments of the invention. They should, in no way be construed, however, as limiting the broad scope of the invention.

EXAMPLES

In the following Examples, the term "12-LO" refers to platelet-type 12-lipoxygenase. The terms "12-HETE" and "12-HETES" are used interchangeably throughout the Examples and Figures.

Materials and Methods

Tissue Culture:

The 3T3-L1 murine preadipocyte cell line was grown in 20% FBS in DMEM with 2 mM Glutamine, penicillin (100 U/ml), streptomycin (0.1 mg/ml) and Amphotericin B (25 µg/ml). These cells are grown at 37° C. and 5.5% $CO_2$ in a water jacketed incubator. Cells were routinely passage upon reaching 80% confluence.

Human preadipocytes were derived from human subcutaneous fat, which was harvested from operations for other purposes, such as gastric bypass. Two grams of fat tissue was harvested for each preparation, which was then disrupted by collagenase (3 mg collagenase/ml Hanks medium {Hanks Buffer, 1.5% BSA, 5 mM Glucose, penicillin (100 U/ml), streptomycin (0.1 mg/ml) and Amphotericin B (25 µg/ml)}) 60 minutes with gentle shaking 70 rpm at 37° C. Following the collagenase treatment, the cells were washed a number of times in PBS and plated in cell medium {DMEM/F12 HEME (1:1), 10% FBS, 2 mM Glutamine, penicillin (100 U/ml), streptomycin (0.1 mg/ml) and Amphotericin B (25 µg/ml)}, which was replaced every 3 days (Prins et al., 1997b).

RNA Preparation:

Total RNA from human subcutaneous fat or preadipocyte cultures were extracted with a mono-phasic solution of phenol and guanidine isothiocyanate (TRIZOL Reagent, Gibco, USA), according to manufacturer's instructions.

Oligonucleotide Primers and Probe for Polymerase Chain Reaction (PCR)

All oligonucleotides were synthesized by Sigma and were purified by HPLC. The sequences of nucleotides, conditions for hybridization and elongation were as published (Limor et al., 2001). The primer sequences are as follows: 5' Primer—GATGATCTACCTCCAAATATG (SEQ ID NO: 10); 3' Primer—CTGGCCCCAGAAGATCTG (SEQ ID NO: 11).

PCR amplified cDNAs were analyzed on 2% E-gels (Invitrogen, Paisley, UK) and photographed using the FUJI BIS202D CCD camera system (Fuji, Japan).

Plasmid DNA Preparation and Transfection into Eukaryotic Cells

Plasmids were introduced into E. coli (DH5a) using standard protocols (Limor et al., 1999, Sambrook et al., 1989). Plasmids were purified using the Roche Plasmid Maxi Kit (Roche; Mannheim, Germany). DNA concentrations were determined using standard optical density measurements at 260 nm.

Transient calcium phosphate transfections were carried as described (Weisinger et al., 1988). Various other protocols were tested on the different preadipocyte cultures including FuGene 6 (Roche; Mannheim, Germany), Lipofectamine 2000 (InVitrogen, Paisley, UK), DOTAP (Biontex, Frankfurt Germany), Metafectene (Biontex, Frankfurt, Germany), Genefect (MoleculA, Sterling, Va., USA) and Magnetofectin (Chemicell GmbH, Berlin, Germany). All reagents were optimized using the manufacturer's instructions, optimized conditions are mentioned for each experiment.

For the production of stable transfectants, the day after transfection 650 µg/ml of G418 (Sigma, St Louis Mo., USA) was added to the cultures for a period of 3 weeks, upon when these levels were gradually reduced over the following week. 600 µg/ml is enough G418 to kill 100% 3T3-L1 cells over 2 weeks. Thus the levels used clearly distinguish between cells that incorporated G418 resistance (within the expression plasmid used) into their genomes and cells lacking this marker. A few passages after G418 release stable populations should recover and fill the plate.

To prepare individual clones of cells, 1 ml aliquots (10-20 or as needed) from a full plate of the stable population in question were put in one short row of 24 well plates. Then each aliquot was serially diluted 1/10 (100 µl cells+900 µl complete medium) 6 times each along the plate. As most cells reach $10^5$ to $10^6$ cells/ml, then 6¹/₁₀ dilutions should result in the most dilute regrown well to be a result of 1-3 individual cells. Performance of this protocol twice on the most dilute regrown well should result in purified clones.

Chloramphenicol Acetyl CoA (CAT) Assay

Forty-eight hours after transfection, cells were washed with PBS, scrapped into 1 ml/100 mm plate of 40 mM Tris-HCl (7.4), 1 mM EDTA and 150 mM NaCl. Cells were then gently microfuged, 1,000×g for 1 minute, the supernated replaced with 500 of 250 mM Tris-HCl (7.8) and resuspended by vortex. This suspension then underwent 3 cycles of freeze (−80° C., 5 minutes)-thawing (37° C., 5 minutes)-vortex, followed by microcentrifugation (5 minutes, 12,000×g). The supernatant after this spin was then transferred to a fresh tube and used for further CAT analysis (Weisinger et al., 1988).

Twenty microliters of CAT extract was mixed with 70 µl of 1 M Tris-HCl (7.8), 39 µl water and 1 µl of [$^{14}$C]-Chloramphenicol (0.1 µCi) and incubated for 5 minutes at 37° C. Then 20 µl of 4 mM acetyl CoA is mixed to each sample and the incubation is allowed to proceed for another hour. The incubation was ended by adding 1 ml of ethyl acetate, vortex mixing the mix for 30 seconds and microcentrifugation for 30 seconds (12,000×g). The supernatant was then transferred to a fresh tube and dried in a vacuum dryer for 60 minutes. The dry powder was then taken up into 20 µl of ethyl acetate and then spotted onto a plastic backed silica gel TLC plate (Merck). The dry plate was then vertically resolved for 90 minutes in 95% chloroform: 5% methanol (v:v) in a preequilibrated chamber. The plate was then removed and air-dried and exposed to Kodak XAR 8×10 cm X-ray film (Weisinger et al., 1988).

Evaluation of Cell Death

Trypan Blue: Initially, in all cell cultures and treatments the amount of trypan blue exclusion was used as an evaluation of cell viability. Cells were counted with and without addition of a 1:1 (v:v) of cell volume to 0.4% trypan blue. Blue cells were counted as dead.

Lactate Dehydrogenase Release (LDH): Necrotic cells release their cytoplasmic contents into the surrounding medium. In recent years the measurement of one such stable enzyme, LDH, has become a standard laboratory marker of necrosis (Goeptar et al., 1994; Moran et al., 1996). Cell cultures and treatments tested for LDH release had their supernatants collected, centrifuged (1,100×g, 5 minutes; to remove particulate debris) and supernatants tested automatically in a centralized facility (in-house) by method of Moran and Schnellmann (Moran et al., 1996), 1996. In each study a positive control for LDH release was a 1/5000 dilution of triton X100 directly into the cell culture, for the period of the bioassay. Negative control was medium without cells.

DNA Fragmentation (ELISA method): Apoptopic cells show hallmark random DNA fragmentation between nucleosomes. The "Cell Death Detection ELISA" format by Roche (Mannheim, Germany) was used in the following examples. Culture treatments and controls were performed for the tested period and after counting the cells and washing them twice with PBS, 250,000 cells/aliquot were prepared and stored dry at −180° C. until assay. Multiple replicates were usually prepared for assay together on the same day in the same kit. Assay was carried out exactly as described by the manufacturer on 250,000 cells/aliquot.

Propidium Iodide (PI) with Anexin V staining: An early marker for apoptosis is the "flip flop" of phosphotidylserine on the plasma membrane of the apoptopic cell. Anexin V binds to phosphotidylserine (PS) in both apoptopic and necrotic cells. PI stains necrotic cells and hence the combination of the two can distinguish apoptopic cells. The Anexin-V-FLUOS staining Kit (Roche; Mannheim Germany) was used for these studies. The staining and the reading of slides and cultures were as described by the manufacturer. Transiently transfected cells were stained 24 or 48 hours after transfection. Percentages of positively stained cells were then used for comparison.

Western Blot Analysis—Caspase 3 Expression: Caspase 3 is a member of the family cysteine proteinases that are important in caspase induced apoptosis (Degterev et al., 2003). In fact the activation of this effector caspase, caspase 3 from the procaspase form, is a clear statement of induced apoptosis (Tong et al., 2002). Caspase 3 can be measured in a number of ways, in the current examples western blot analysis was used.

Following different treatments cell culture protein extracts were prepared as previously described (Limor et al., 2001). Fifty µg of proteins were routinely applied to each lane of 8-12% polyacramide premade Tris-Bis 1 mm gels (NuPage, Invitrogen, Paisley, UK), run in NuPage "SDS-MES" buffer for 45 minutes at 150 V, according to the manufacturer's suggestions. One lane in each gel included "Precision Plus prestained molecular weight markers" (BioRad, Hercules, Calif., USA). Following the completion of the electrophoresis, the 8×10 cm gel underwent western transfer to Protean nitrocellulose (NC) (S&S, Germany) in NuPage transfer buffer with 10% methanol (30V, 90 minutes). Following, western transfer the NC was blocked with 2% BSA in 20 mM Tris-HCl (7.6), 137 mM NaCl, 3.8 ml 1M HCl and 0.1% Tween 20 (TBS-T); rinsed ×2 briefly followed a 15 minute wash with TBS-T with gentle agitation. The blocked blot was then incubated with the polyclonal rabbit antiActive Caspase 3 antibody (BioVision; Mountain View, Calif., USA; #3015-100), used at 1 µg/ml of 1% BSA in TBS-T, for 60 minutes with gentle agitation. The NC was then rinsed ×2, followed by a 15 minute wash and then 2×5 minute washes all with TBS-T. Next the NC was incubated for an hour with 1/5000 dilution of goat antiRabbit IgG-HRP (ECL, Amersham, Buckinghamshirem UK). Again the blot was cleaned from nonspecific antibody interaction by 1 brief rinse, 1×15 minute wash and 4×5 minute washes all with TBS-T. The NC was then developed with the "ECL Plus" substrate (ECL, Amersham, Buckinghamshirem UK) for the appropriate time and exposed to Kodak XAR X-ray film.

Images were digitized with the CCD-camera/computer BIS202D (FUJI; Fuji, Japan) and the numbers extracted using the TINA2 software (FUJI; Fuji, Japan).

Statistics

Data is presented as Mean±SEM. Statistical significance was assumed at $p \leq 0.05$. Student t-test or one-way analysis of variance parametric or nonparametric) followed by the Newman-Keuls or Mann-Whitney post hoc analyses were used, as appropriate.

Example 1

Presence of "Platelet-Type" 12-Lipoxygenase in Fat Cells

Figure 1B:
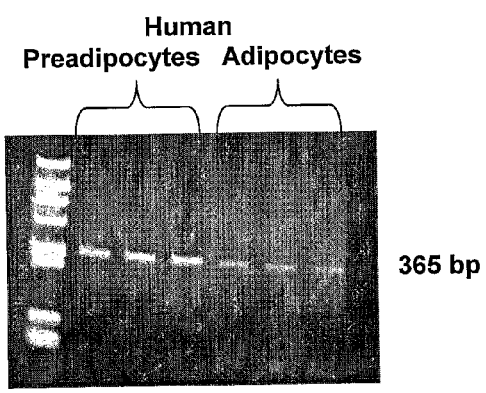

To establish whether 12-lipoxygenase is expressed in both the murine preadipocytes cell line 3T3-L1 cells and in human fat tissue, total RNA from murine 3T3-L1 preadipocyte cell line (left panel) and primary human preadipocytes and adipocytes (right panel) was prepared and subjected to PCR using primers for the appropriate species 12-lipoxygenase (mouse or human). The cDNA products were resolved on 2% E-Gels and a typical example is seen in FIG. 1.

Replicate RNA preparations show that in both human and rodent preadipocytes and human adipocytes, Platelet-type 12-Lo RNA is expressed. Interestingly it seems that there may be slightly less expressed in mature human adipocytes than in preadipocytes, but this should advantageously to be further quantitated with better quantitative methods. The murine RNA samples clearly show the band for murine platelet-type 12-lipoxygenase, and the human RNA samples show the band corresponding to the smooth muscle cell variant of platelet-type 12-Lo (Limor et al., 2001).

Example 2

Plasmids Constructed for the Constitutively Expressed Antisense Knockout of "Platelet-Type" 12-Lipoxygenase and Optimizing the Lipofection Reagent A series of Calcium Phosphate transfections (Weisinger et al., 1988) were performed on these cells in culture to determine which constitutive promoter/enhancer unit would best function (of those tested) in the murine 3T3-L1 preadipocyte and human primary cultured preadipocytes as well as adipocytes. The following promoter/enhancer cassettes were tested in the context of the pCATBasic plasmid (Promega, Madison, Wis., USA): SV40, Raucher Sarcoma virus (RSV), CMV, Human proenkephalin (ppEnk) and the Herpes Thymidine Kinase promoter/enhancer (Weisinger et al., 1988, LaGamma et al., 1993). The CMV promoter/enhancer was the most optimal of these 5 cassettes for fat cell expression.

Figure 2B:
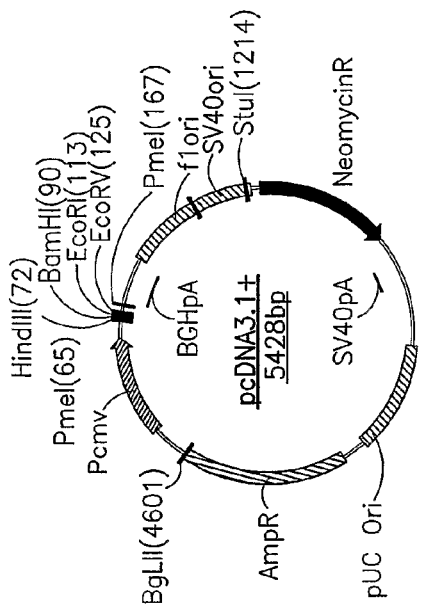
FIG. 2B illustrates pcDNA3.1+.
Figure 2D:
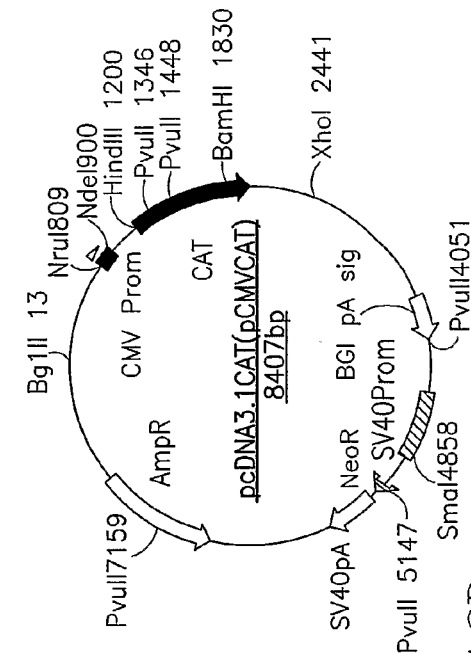
FIG. 2D illustrates pCMVCAT.
Figure 2A:
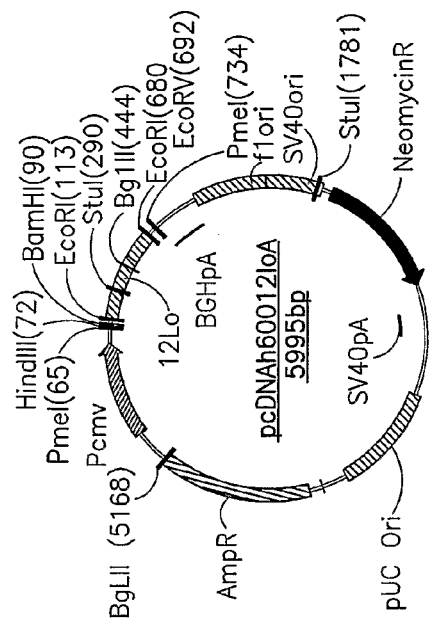
FIG. 2A illustrates pcDNAh600 12LOA.
Figure 2C:
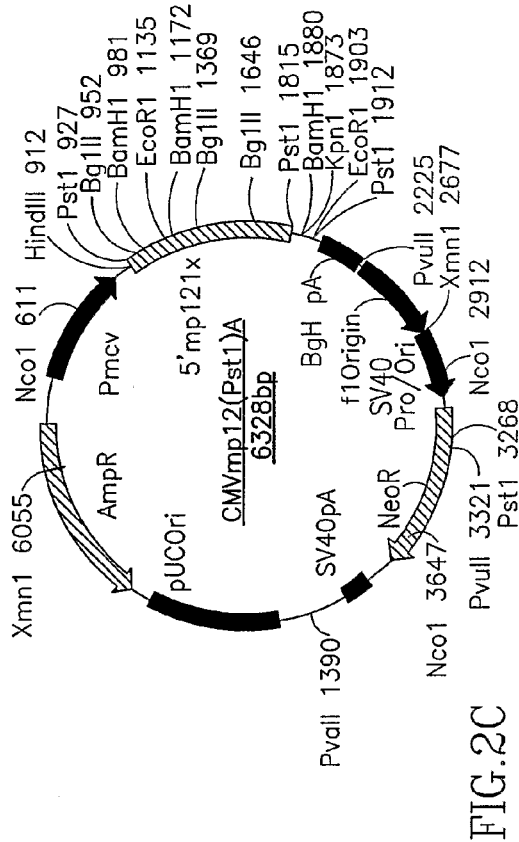
FIG. 2C illustrates pCMV5'mp12LO (Pst1)-A.

Consequently, two CMV driven 12Lo antisense knockout plasmids (illustrated in FIG. 2) were prepared as detailed below. The controls for the future studies were either the parent pcDNA3.1(+) (FIG. 2B) or pcDNACAT (also known as pCMVCAT) (FIG. 2D).

pCMV5'mp12Lo(Pst1)-A (FIG. 2C)

The 5' Pst 1 murine platelet-type cDNA 12LO (mp12LO) 887 bp fragment, SEQ ID NO: 2) was cloned into the Pst 1 site of pUC18 (Gibco BRL Life Technologies; Paisley, UK). Then the 900 bp Hind III-HincII restriction fragment (with mp12Lo antisense with respect to the Hind III site) was cloned into the Hind III, EcoRV precut, bacterial alkaline phosphatase treated pcDNA3.1+ plasmid vector (Invitrogen; Paisley, UK). So the resultant pCMV5'mp12LO(Pst1)-A vector expresses the 5'mp12LO sequence in the antisense orientation with respect to the CMV promoter/enhancer. See FIG. 2B for the pcDNA3.1+ vector map and FIG. 2C for the pCMV5'mp12LO(Pst1)-A vector map (designated therein "CMVmp12(Pst1)A").

pcDNAh60012LoA (FIG. 2A)

The EcoRI 605 bp human platelet form (smooth muscle variant) of 12LO cDNA fragment, previously cloned and described by us (28) was cloned into the EcoRI site of the pcDNA3.1+ expression vector. So the resultant pcDNAh60012LOA vector expresses the 605 bp 12LO sequence in the antisense orientation with respect to the CMV promoter/enhancer. See FIG. 2B for the pcDNA3.1+ vector map and FIG. 2A for the pcDNAh60012LOA plasmid vector map.

Transfection Reagent

To find an appropriate transfection reagent that would allow maximal expression with minimal method related cell death, 6 reagents were studied (using their manufacturers' instructions) to measure CAT expression (Weisinger et al., 1988) as well as the percentage of cells that excluded trypan blue (0.02% v/v). Trypan blue exclusion is a traditional measure of cell viability. The results of this study are summarized in Table 1. As can be seen from these data, murine preadipocyte cultures were most effectively transfected using Fugene 6 (Roche, Mannheim, Germany) with a very high level of CAT expression (86.71%) as well as no method-related cell death. Human preadipocyte cultures were not transfectable using this same reagent. Unfortunately, the best results seen for the human cultures were with Magnetofectin (using a 2:2 lipid:DNA ratio), which only showed moderate to low expression (11.07%) with very significant method-related cell death (95%). While changing the ratio to (10.67:2) vastly reduced method associated cell death to 40% of cells, it also reduced CAT expression to 8.55%. (see Table 1). As the antisense knockout should induce fat cell death, a high background of method related cell death may indicate that more reagents should be tested and/or a viral based expression system, as demonstrated in Example 9, should be advantageous.

TABLE 1

Choosing the optimal lipofection reagent for transfection into murine and human preadipocytes using the constitutively expressing pCMVCAT plasmid vector.

| Cell Type | Method | Cell Death (%) | % CAT Converted |
|---|---|---|---|
| 3T3-L1 | Fugene6 (3:3) | 0 | 86.71 |
| Human Preadipocytes | Fugene6 (3:3) | 0 | 0 |

TABLE 1-continued

Choosing the optimal lipofection reagent for transfection into murine and human preadipocytes using the constitutively expressing pCMVCAT plasmid vector.

| Cell Type | Method | Cell Death (%) | % CAT Converted |
|---|---|---|---|
| 3T3-L1 | Lipofectamine 2000 (2.5:1) | 60 | 63.37 |
| Human Preadipocytes | Lipofectamine 2000 (2.5:1) | 95 | 0 |
| Human Preadipocytes | DOTAP (16:2) | 5 | 5.51 |
| Human Preadipocytes | Metafectene (10.67:2) | 40 | 8.55 |
| Human Preadipocytes | Genefect | 10 | 0 |
| Human Preadipocytes | Magnetofectin (2:2) | 95 | 11.07 |

For each transfection protocol the level of cell death was determined by measuring trypan blue exclusion. Additionally the % of CAT converted was determined as a measure of transfection efficiency.

Example 3

Antisense Knockout of 12-Lipoxygenase in 3T3-L1 cells: Transient Transfection

Cell Viability

Figure 3:
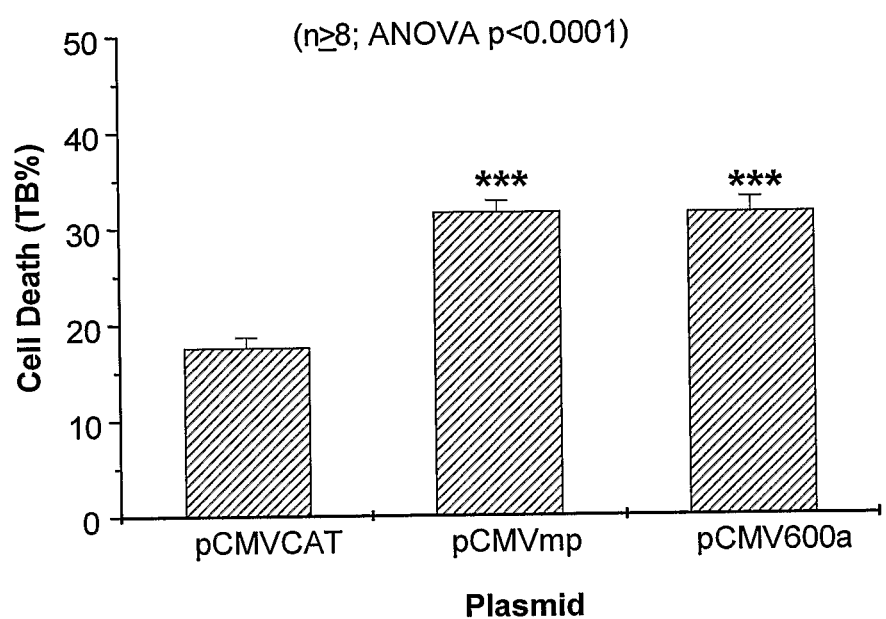
FIG. 3 shows transient 12-Lo antisense knockout of 3T3-L1 cells, wherein trypan blue exclusion was used as a measure of cell death 48 hours after transfection with the Fugene 6 reagent. The vector pCMVCAT was used as the negative control, while the two 12Lo antisense knockout vectors pCMVmp and pCMV600a effectively induced significant cell death in preadipocytes (n≥8 ANOVA, p<0.0001; ***=post hoc difference to control of p<0.001).

3T3-L1 cells were subject to Fugene 6 lipofection under optimal conditions with the two 12-Lo antisense knockout plasmids described in Example 2 and one control (pcDNA3.1+ or pcDNA3.1CAT) plasmid. Two days after lipofection of the plasmids into multiple replicates of the cultures trypan blue exclusion (viability) was measured. A typical experiment is shown in FIG. 3, wherein the pCMV5' mp12Lo(Pst1)-A plasmid is designated "pCMVmp", the pcDNAh60012LoA plasmid is designated "pCMV600a", and the pcDNA3.1 CAT plasmid is designated "pCMV-CAT"). As transient transfection introduces the exogenous DNA into only a portion of the cells' cytoplasm, and as these plasmids are not autonomously replicating, any effect measured most probably represents a much larger effect. The results shown in FIG. 3 indicate that both 12Lo antisense knockout plasmids almost doubled the amount of dead cells 48 hours after transfection. As can be seen in the figure, these results are very significant (N≥8: ANOVA p<0.0001). On student Newman Keuls post hoc analysis of these data both antisense plasmids were significantly different from the control cells (p<0.001). Both antisense knockout plasmids gave similar results, which may be related to the fact that the human and murine "platelet-type" 12-Lo sequences are highly conserved.

Anexin V-PI Apoptosis Study

Figure 4:
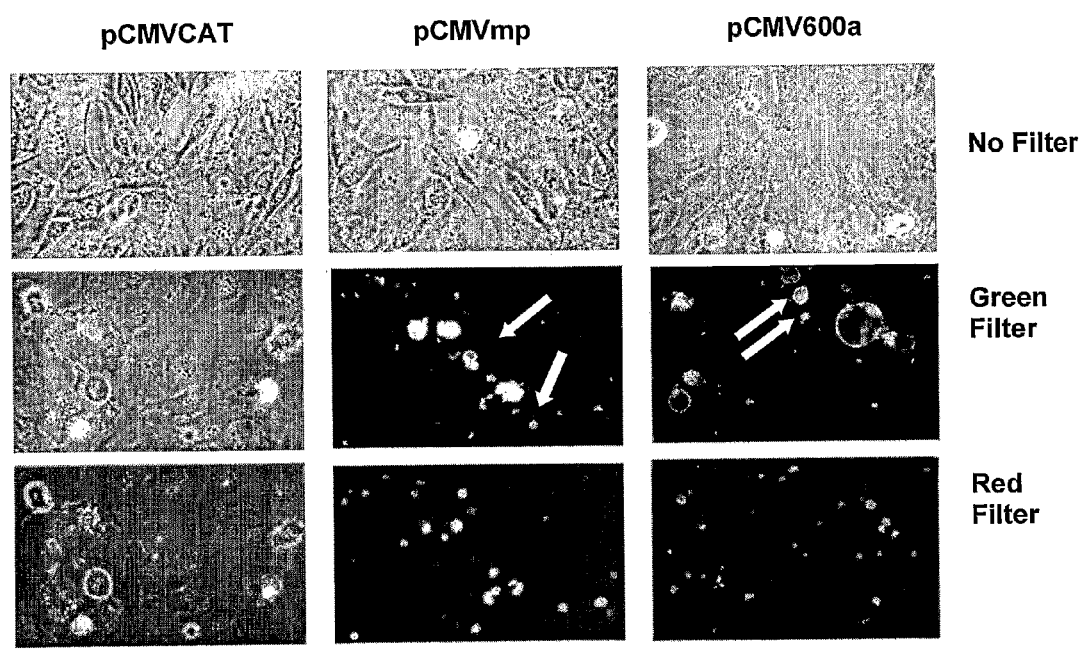
FIG. 4 shows Anexin V and PI stained transiently transfected 3T3-L1 cells; 24 hour post transfection images using Fugene 6. The vector pCMVCAT was used as the negative control, while the two 12Lo antisense knockout vectors were pCMVmp and pCMV600a. "No filter" shows the total field of cells; "green filter" shows both apoptopic and necrotic cells; and "red filter" shows only necrotic cells. White arrows indicate apoptotic cells.
Figure 5:
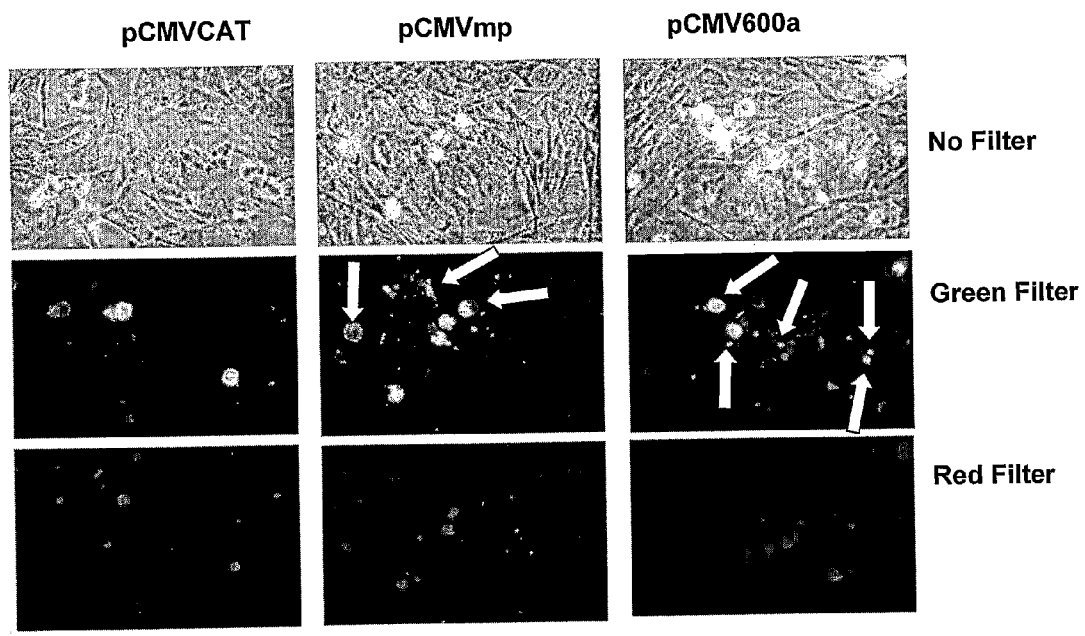
FIG. 5 shows Anexin V and PI stained transiently transfected 3T3-L1 cells; 48 hour post transfection images using Fugene 6. The vector pCMVCAT was used as the negative control, while the two 12Lo antisense knockout vectors were pCMVmp and pCMV600a. "No filter" shows the total field of cells; "green filter" shows both apoptopic and necrotic cells; and "red filter" shows only necrotic cells. White arrows indicate apoptotic cells.
Figure 6:
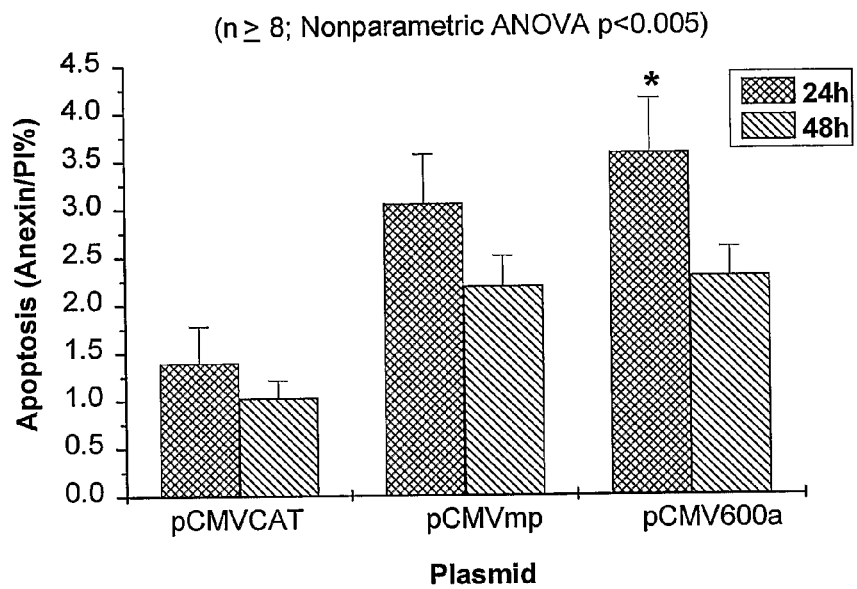
FIG. 6, summarizes data for Anexin V and PI stained transiently transfected 3T3-L1 cells. Antisense knockout of 12Lo significantly increased the amount of apoptosis associated phosphotidylserine "flip flop" at the plasma membrane (n≥8 Nonparametric ANOVA, *=p<0.005).

Having seen significant cell death over and above the controls, the type of cell death was investigated. "Flip flop" of Anexin V on the plasma membrane of the cell is an early marker of apoptosis. A fluorescent kit was used together with propidium iodide (PI) counter staining to differentiate between apoptotic (seen only with green filter) versus necrotic cells (Allen et al., 1997). Necrotic cells also stain with PI (seen with red filter) but not apoptotic cells. FIGS. 4-6 present examples of these data with transiently transfected cells (as above).

FIG. 4 shows anexin V and PI stained transiently transfected 3T3-L1 cells; 24-hour post transfection images using Fugene 6. The vector pCMVCAT was used as the negative control, while the two 12Lo antisense knockout vectors were pCMVmp and pCMV600a. In FIG. 4, images presented are at a ×100 magnification. Each field of vision is shown with 3 filters; no filter, to show the total field of cells; green filter, shows both apoptopic and necrotic cells; red filter, shows only necrotic cells. So cells that stain with the green filter and not with the red filter are cells in apoptosis.

FIG. 5 shows Anexin V and PI stained transiently transfected 3T3-L1 cells; 48-hour post transfection images using Fugene 6. The vector pCMVCAT was used as the negative control, while the two 12Lo antisense knockout vectors were pCMVmp and pCMV600a. In FIG. 5, images presented are at an ×100 magnification. Each field of vision is shown with 3 filters; no filter, to show the total field of cells; green filter, shows both apoptopic and necrotic cells; red filter, shows only necrotic cells. So cells that stain with the green filter and not with the red filter are cells in apoptosis. White arrows indicate apoptotic cells.

Again any significant differences, marginal as they may be, with this transient antisense knockout of 12-lipoxygenase may indicate that by other more extensive methods these differences will be much greater. On tabulating the data for all of these transient Anexin V studies (see FIG. 6), nonparametric ANOVA analysis indicated that with $n \geq 8$, $p<0.005$. On applying Dunn's posthoc analysis it became clear that 24 hours after plasmid transfection pCMV600a was already significantly different to the control plasmid transfected cells ($p<0.05$). Although the other knockout plasmid was not yet significantly different to the control cells, at 24 hours, the trend for this difference is already obvious (see FIG. 6). Transient transfections of these non-replicating plasmids reach their peak effect before the cells restart replicating. Upon replication, plasmid-containing cells are diluted as each plasmid molecule will go with only one of the dividing cells. Consequently, it is not surprising that the Anexin V "flip flop" observed in these cells 24 hours after transient transfection is diminished after 48 hours (FIG. 6). In summary, these data suggest that the cell death noted in 12-Lo antisense knockout 3T3-L1 cells, as detailed above, may be apoptopic in nature.

Example 4

Antisense Knockout of 12-Lipoxygenase in 3T3-L1 Cells: Stable Transfection: Population Studies Optimization Following the successful identification of 12Lo antisense knockout induced preadipocyte cell death using transient transfection, the more time consuming undertaking of preparing stable 12Lo antisense knockout clones became more critical.

The Fugene6 protocol was then used again for preparation of 12Lo antisense knockout and control clones together with the G418 selection marker as G418 resistance was built in to the pcDNA3.1 plasmid (see FIG. 2). It was herein determined that 600 µg/ml G418 killed 100% of 3T3-L1 cells over two weeks. So on transfection of cells and selection with 650 µg/ml G418 over three weeks only those cells expressing strong Tetracycline resistance would survive and grow. Following three weeks of selection G418 release was gradual over the next 1-2 weeks.

Stable Population

Figure 7:
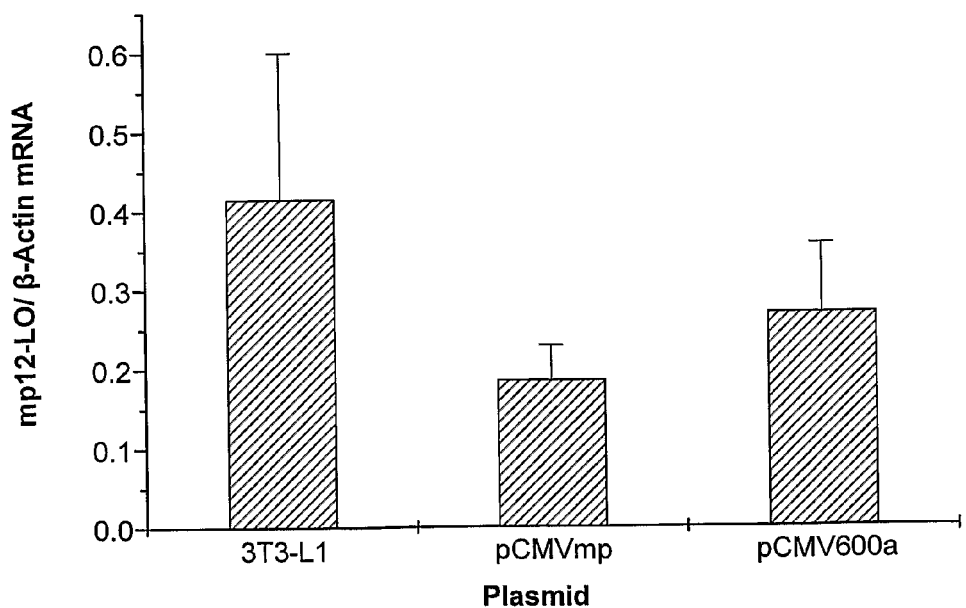
FIG. 7 depicts basal 12Lo RNA expression of 12Lo stable antisense knockout populations versus controls. Data is presented after normalization of 12Lo to β-actin RNA levels.

FIG. 7 depicts basal 12Lo RNA expression of 12Lo stable antisense knockout populations versus controls. Data is presented after normalization of 12Lo to β-actin RNA levels.

Figure 8:
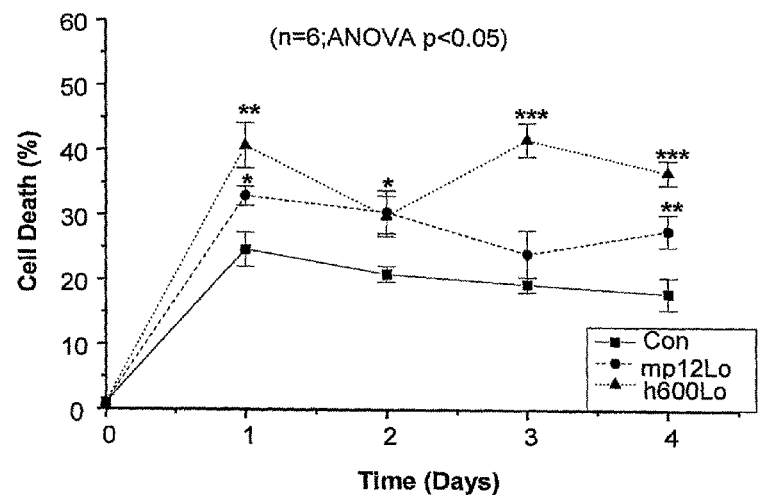
FIG. 8 presents basal cell death of 12Lo stable antisense knockout populations versus controls. Cell death was measured by trypan blue staining of 3T3-L1 cells. Antisense Knockout of 12Lo showed significantly more cell death for both antisense knockout plasmids compared to a pCMVCAT transfected control population (n=6 ANOVA, p<0.05). Post hoc comparisons using the Student Neuman Keuls Protocol showed *=p<0.05; =p<0.01; *=p<0.001, compared to the parallel day control population.

FIG. 8 presents basal cell death of 12Lo stable antisense knockout populations versus controls. Cell death was measured by trypan blue staining of 3T3-L1 cells. Antisense Knockout of 12Lo showed significantly more cell death for both antisense knockout plasmids compared to a pCMVCAT transfected control population.

As can be seen in FIGS. 7 and 8, the 12Lo antisense knockout population for plasmid pCMV600a (triangles) significantly shows halving of the expression of 12Lo RNA and about double the cell death than control cells, respectively, (n=6, ANOVA $p<0.05$; Student Newman Keuls posthoc $p<0.001\equiv***$), while the other 12Lo antisense knockout plasmid population, mp12Lo (circles; pCMV5'mp12Lo(Pst1)-A, also designated "pCMVmp"), exhibits much more cell death than the control cells (squares; "3T3-L1", also designated "Con"), but less then the population derived from pCMC600a.

Figure 9:
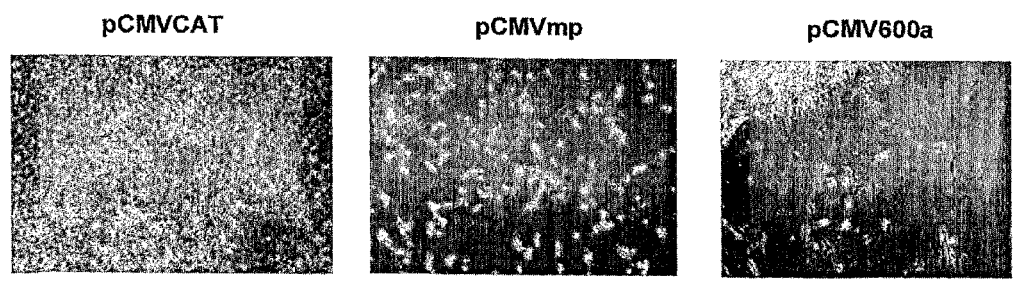
FIG. 9 presents basal cell death of 12Lo stable antisense knockout populations versus controls 5 weeks post transfection. Antisense knockout of 12Lo in 3T3-L1 cells shows much lower cell concentrations than for the control population. Images are at an ×100 magnification.

Looking at the photomicrographs in FIG. 9, one can see that while control cell populations readily grow back to confluence, antisense knockout populations do not.

Figure 10A:
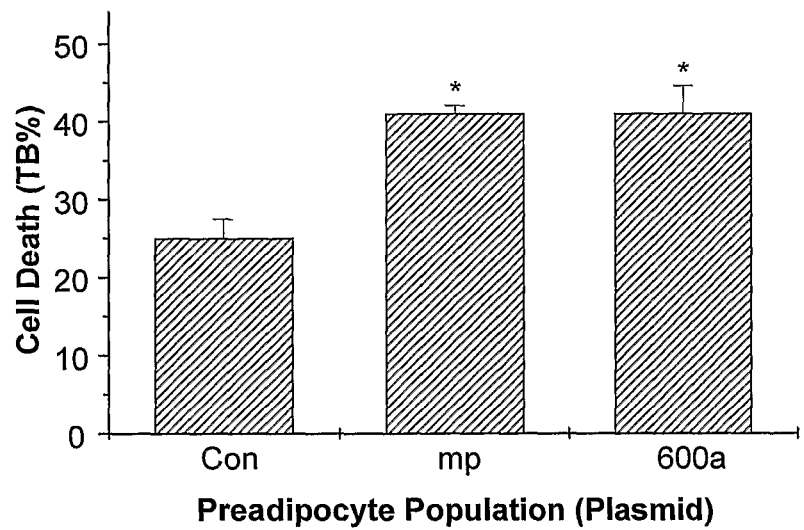
FIG. 10 shows basal cell death (A) and DNA fragmentation (B) of 12Lo stable antisense knockout populations versus controls 5 weeks post transfection in parallel cultures. Basal cell death was measured by trypan blue staining of 3T3-L1 cells. DNA fragmentation was measured using the Roche Cell Death ELISA kit *=p<0.05; ***=p<0.001 as Student Neuman Keuls post hoc values.
Figure 10B:
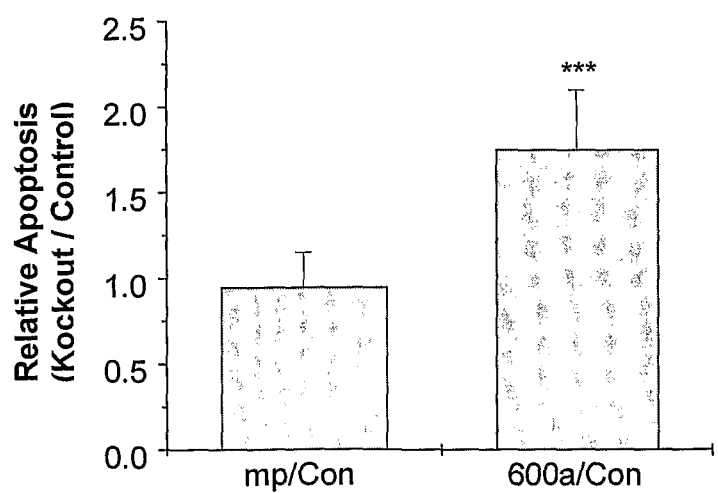

One hallmark of apoptosis is DNA fragmentation. In the current studies the Roche (Mannheim, Germany) version of this assay was used in the format of an ELISA assay, which measures released intact DNA/Histone-nucleosomes. The results are presented as antisense knockout levels normalized to parallel control values. In the experiment shown in FIG. 10, populations of 3T3-L1 cells with either of the two 12Lo antisense knockout plasmids ("mp"—pCMV5'mp12Lo (Pst1)-A; "600a"—pcDNAh60012LoA) versus controls ("Con") were directly compared: cell death versus relative DNA fragmentation. What can be learned is that while trypan blue exclusion measured cell death similar to the previous experiment (compare FIG. 8 to FIG. 10), only the pCMV600a stably transfected population showed a significant ($p<0.001$) near doubling of DNA fragmentation which was similar to the increase in cell death measured in these cells. This suggests that more than one mode of cell death may play a role in the antisense knockout of 12-lipoxygenase induced cell death in adipocytes.

Example 5

Antisense Knockout of 12-Lipoxygenase in 3T3-L1 Cells: Stable Transfection: Clonal Studies Stable populations of 12Lo antisense knockout 3T3-L1 preadipocytes showing a mean of 40-50% cell death probably represents many clonal variants of the exogenous DNA inserted into different positions in the genome. Consequently, within the population exist clones with near 100% cell death as well as other clones very resistant to death, as well as the spectrum in between. Upon isolation of these various clones one can learn more about this variation as well as better characterize the mode of cell death. To this end stable populations were processed through multiple dilution cloning procedures to isolate individual clones.

Upon dilution cloning both pCMVmp and pCMV600a cells went into "total" or near total cell death (FIG. 11). 12-HETE is the "normal" product of the reaction of platelet-type 12-lipoxygenase with arachidonic acid (Brash, 1999). If indeed the 12Lo protein is essential to cell life, could the essential function it provides be the formation of its product 12-HETE? To test this, dilution cloning of the knockout clones in the presence of 12-HETE ($10^{-7}$ M) were also performed.

Figure 11:
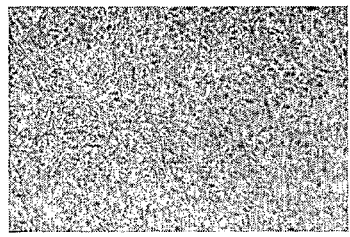
FIG. 11 demonstrates basal cell death of 12Lo stable antisense knockout of individual clones versus control clone with and without added 12-HETE.
Figure 11:
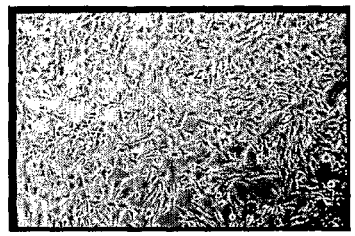
Figure 11:
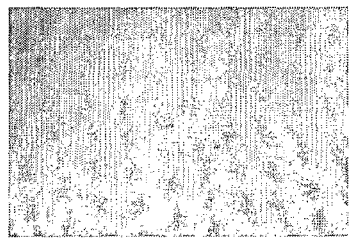
Figure 11:
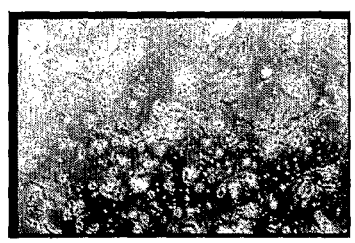
Figure 11:
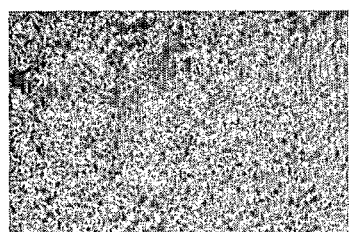
Figure 11:

Typical results are presented in FIG. 11, which demonstrates basal cell death of 12Lo stable antisense knockout of individual clones versus a control clone incubated with ("Clone +12HETE") and without ("Clone −12HETE") added 12-HETE. "Source" indicates the predilution-cloning transfected population. Images are at an ×100 magnification. The results show that for the most part the clones grown with 12-HETE showed much less cell death (see FIG. 11). This suggests that at least one of the necessary factors needed for these antisense knockout clones to survive is the product of 12-lipoxygenase, 12-HETE.

Example 6

Antisense Knockout of 12-Lipoxygenase in 3T3-L1 Cells: Stable Clones: Cell Death and Apoptosis Cell Death Four clones derived from the pCMV600a (Clones 1, 9, 10, 11) population were compared among themselves and to a clone derived from the control plasmid pCMVCAT (clone 1) population when they were grown in the presence or absence of $10^{-7}$M 12-HETE.

Figure 12:
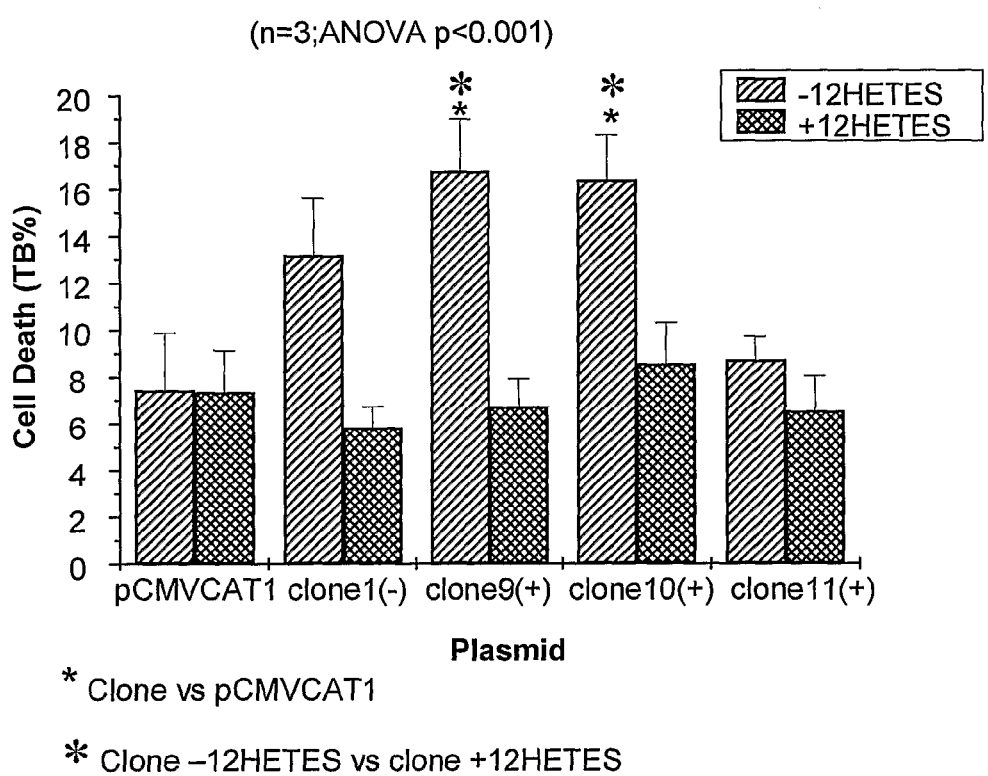
FIG. 12 demonstrates cell death of 12Lo stable antisense knockout clones (pCMV600a) versus control (pCMVCAT) with and without added 12-HETE. Clones were derived using a dilution cloning protocol in the presence of (+) or absence of (−) 12-HETE. Resultant clones cell death were then compared to each other and themselves in the presence of (//) of absence of (XX) 12-HETE (n=3; ANOVA p<0.001; post hoc *=p<0.05).

FIG. 12 demonstrates cell death of 12Lo stable antisense knockout clones (pCMV600a) versus control (pCMVCAT) with and without added 12-HETE. Clones were derived using a dilution cloning protocol in the presence of (+) or absence of (−) 12-HETE. Resultant clones cell death were then compared to each other and themselves in the presence of (//) or absence of (XX) 12-HETE (n=3; ANOVA p<0.001; post hoc *=p<0.05). Results are presented as % trypan blue exclusion (TB %).

When the effect of 12-HETE on cell survival was followed (FIG. 12), 12-HETE showed no effect on the pCMVCAT stably transfected 3T3-L1 cells. In contrast to this, clearly the presence of added 12-HETE encouraged cell survival in the 12Lo antisense knockout clones. As the presence of 12-HETE for both antisense knockout clones and the control clone showed approximately the same level of cell death it is apparent that 12-HETE was enough to correct the reduced expression of the 12-lipoxygenase enzyme. Additionally, when comparing the effect of 12-HETE on each of the 12Lo crippled preadipocyte clones (see FIG. 12), clear clonal variation in their responsiveness to 12-HETE was observed. This indicates that the random insertion of the exogenous DNA may play a role in the strength of the expression of the antisense knockout cDNA.

Apoptosis

Figure 13:
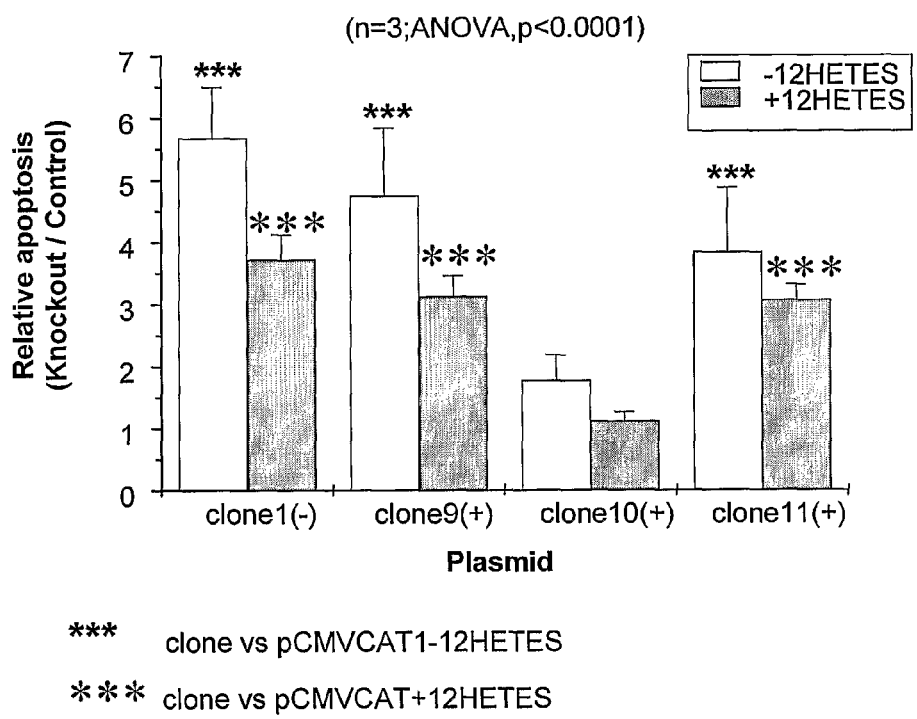
FIG. 13 demonstrates DNA Fragmentation (Roche Cell Death ELISA kit) of 12Lo stable antisense knockout clones (pCMV600a) versus control (pCMVCAT) with and without added 12-HETE. Data is presented showing antisense knockout values normalized to pCMVCAT transfected clone cells. A value of 1 on this graph indicates no DNA fragmentation. Differences here were significant as ANOVA p<0.0001 and Neuman Keuls post hoc showed ***=p<0.001.

To further validate the mechanism of cell death the Roche Cell Death kit was applied as a measure of DNA fragmentation, which is a classic apoptopic hallmark. Again the same control and pCMV600a clones were grown in the presence or absence of $10^{-7}$M 12-HETE, before cell harvest and preparation for assay. The same clones used in the current study were those used in the cell death study, presented in FIG. 12. FIG. 13 shows the changes of relative DNA fragmentation with respect to the control cells for 4 of the pCMV600a stable clones. The data in FIG. 13 clearly show that these 12Lo antisense knockout stable preadipocyte clones express various levels of DNA fragmentation. Levels of DNA fragmentation range from nearly six fold more for clone 1 to almost 2 fold for clone 10 over the control transfected cells. This suggests that an apoptotic mechanism is killing the cells. To confirm this, another independent apoptopic test was investigated (see below).

To see if the replacement of 12-HETE missing for the 12Lo reduced expressing cell lines could "rescue" the cells from apparent apoptopic cell death, cells grown in the presence and absence of 12-HETE were compared at the level of DNA fragmentation. FIG. 13 shows that indeed $10^{-7}$M 12-HETE reduced the DNA fragmentation levels for each of the affected clonal stable lines. Only clone 10 showed nearly "normal" (or control) levels of DNA fragmentation on supplemented 12-HETE. This could indicate the need for greater levels of 12-HETE for some of the cells or that another component could be missing.

Figure 14:
FIG. 14 demonstrates Caspase 3 activation in 12Lo stable antisense knockout clones (pCMV600a) versus controls: Western Analysis. The lettering above the western image represent different clones: L1=untransfected parent line (3T3-L1); CAT=pCMVCAT clone 1; 1, 10 & 11 represent pCMV600a antisense knockout clones.

Caspase-associated apoptosis being a major form of apoptosis may be also playing a role in the cell death described for these cells. For most cells and tissues the central executioner caspase is caspase 3. The induction of this caspase in the stable cell lines generated was measured. Cell extracts were prepared from some of the pCMV600a lines as well as from control cells. Equal quantities of proteins from each of these extracts were separated by SDS polyacrylamide gel electrophoresis following by western analysis using an active anti-Caspase 3 specific antibody. In FIG. 14, results of one such experiment are presented.

FIG. 14 demonstrates Caspase 3 activation in 12Lo stable antisense knockout clones (pCMV600a) versus controls by Western Analysis. The lettering above the western image represent different clones: L1=untransfected parent line (3T3-L1); CAT=pCMVCAT clone; 1, 10 and 11 represent pCMV600a antisense knockout clones. In this study the 17 kDa active caspase is vastly over-expressed in clone 1, marginally over expressed for clone 10 and almost not expressed over baseline for clone 11. Interestingly, clone 11 showed the lowest levels of cell death seen in FIG. 12, while clone 1 showed significant cell death over control cells. These data together with the DNA fragmentation data above (FIG. 13) make the apoptopic mode of cell death a stronger case. It seems therefore that 12 lipoxygenase may be a cell survival factor (through possibly 12-HETE) protecting cells from unnecessary apoptosis.

Example 7

Figure 15:
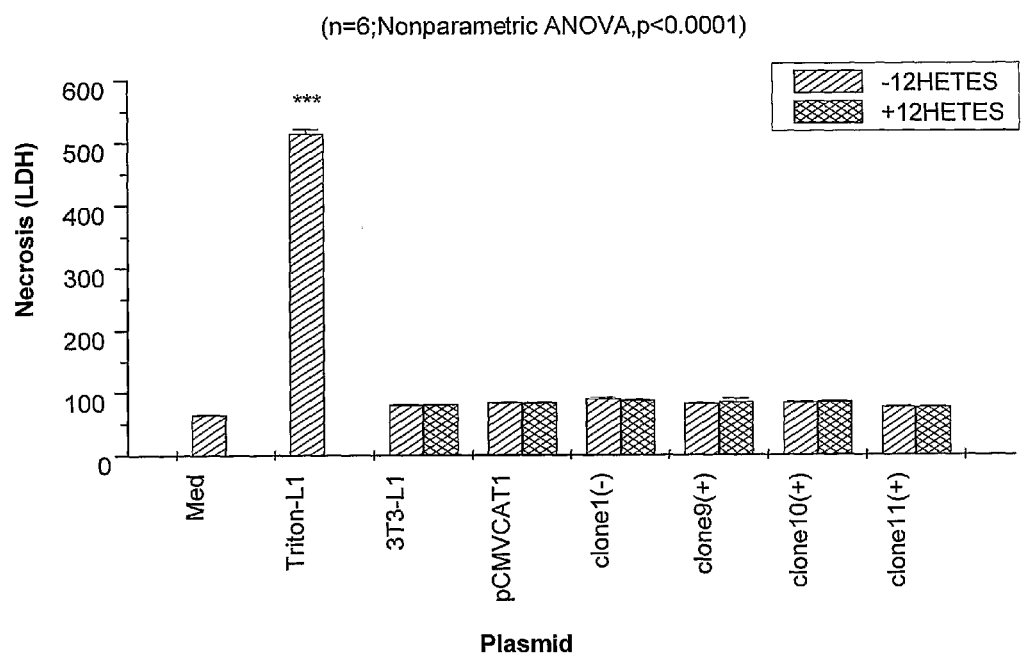
FIG. 15 demonstrates involvement of necrosis in the 12Lo antisense knockout 3T3-L1 stable cell lines. Necrosis here was measured by the release of lactate dehydrogenase (LDH) from cells into cell supernatant by the end of the experiment. The positive control was triton X100 (1/5000) addition to control cells for the duration of the experiment. There was no difference between antisense knockout clones and control cells LDH levels, which indicates that 12Lo antisense knockout in 3T3-L1 cells induced cell death is not necrotic in nature.

Antisense Knockout of 12-Lipoxygenase in 3T3-L1 Cells: Stable Clones: Cell Death and Necrosis Cell death can occur as a result of different processes: apoptosis, which is a very programmed process, as well as other less programmed mechanisms such as necrosis. In the necrosis cell pathway, plasma cell membranes tend to break relatively early in the process, hence spilling out their cytoplasmic contents. In recent years, investigators have been measuring the release of lactate dehydrogenase (LDH) from cells as a measure of cellular necrosis. The contribution of necrosis in the cell death of the 12Lo reduced expressing clones was thus examined by comparing LDH release from control and pCMV600a 12Lo antisense knockout stable preadipocyte cell lines grown in the presence or absence of 12-HETE. In FIG. 15, typical data of such a study is presented. The positive control, triton-X100 treated 3T3-L1 (Triton-L1) clearly shows what levels of LDH can be expected, while the medium alone (Med) shows expected background levels. The data clearly shows no evidence of necrosis in the cell lines and consequently no effect of 12-HETE on cell necrosis.

Example 8

Figure 16:
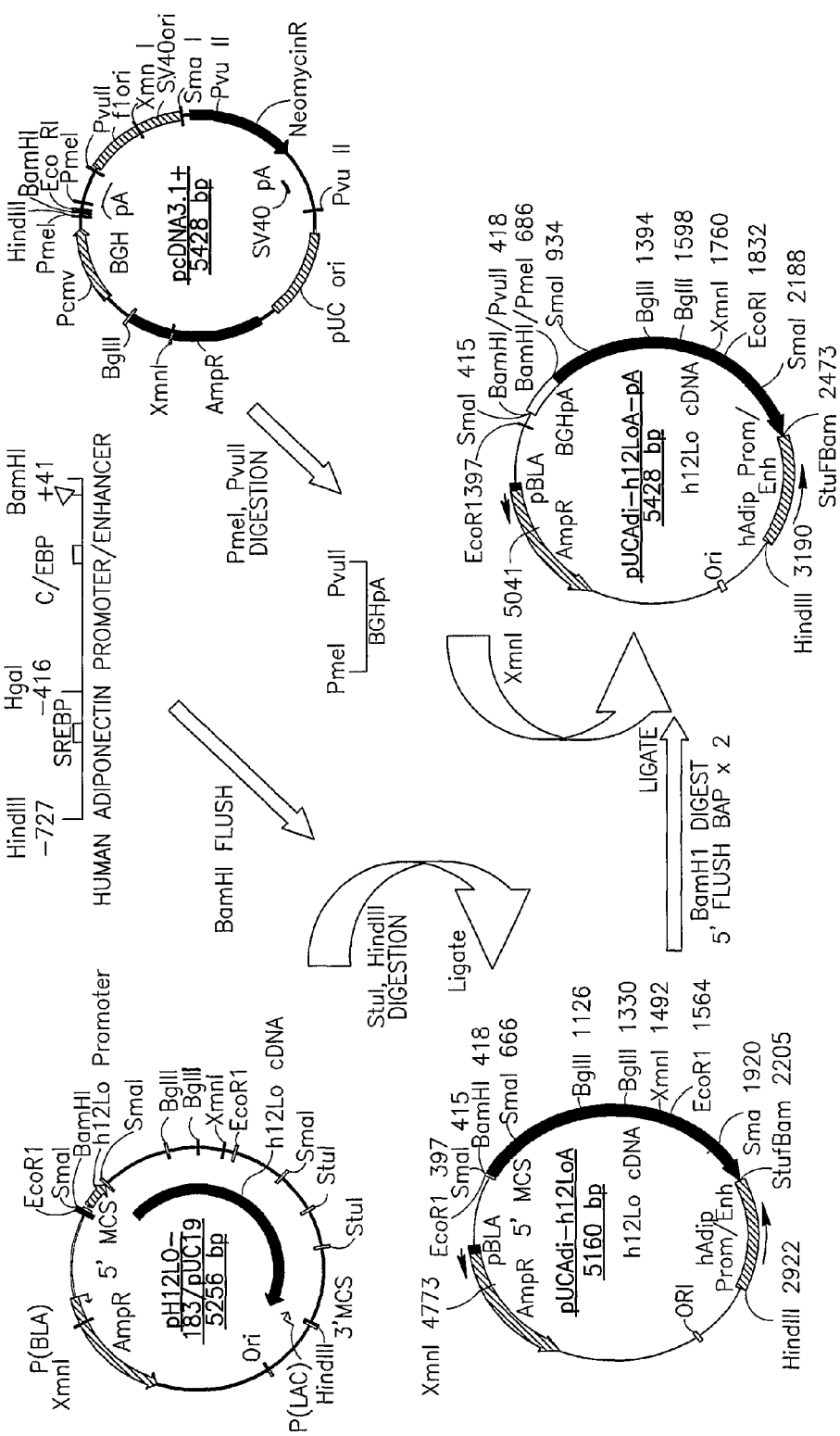
FIG. 16 demonstrates construction of Adiponectin Driven h12Lipoxygenase knockout plasmid Vector.
Figure 17:
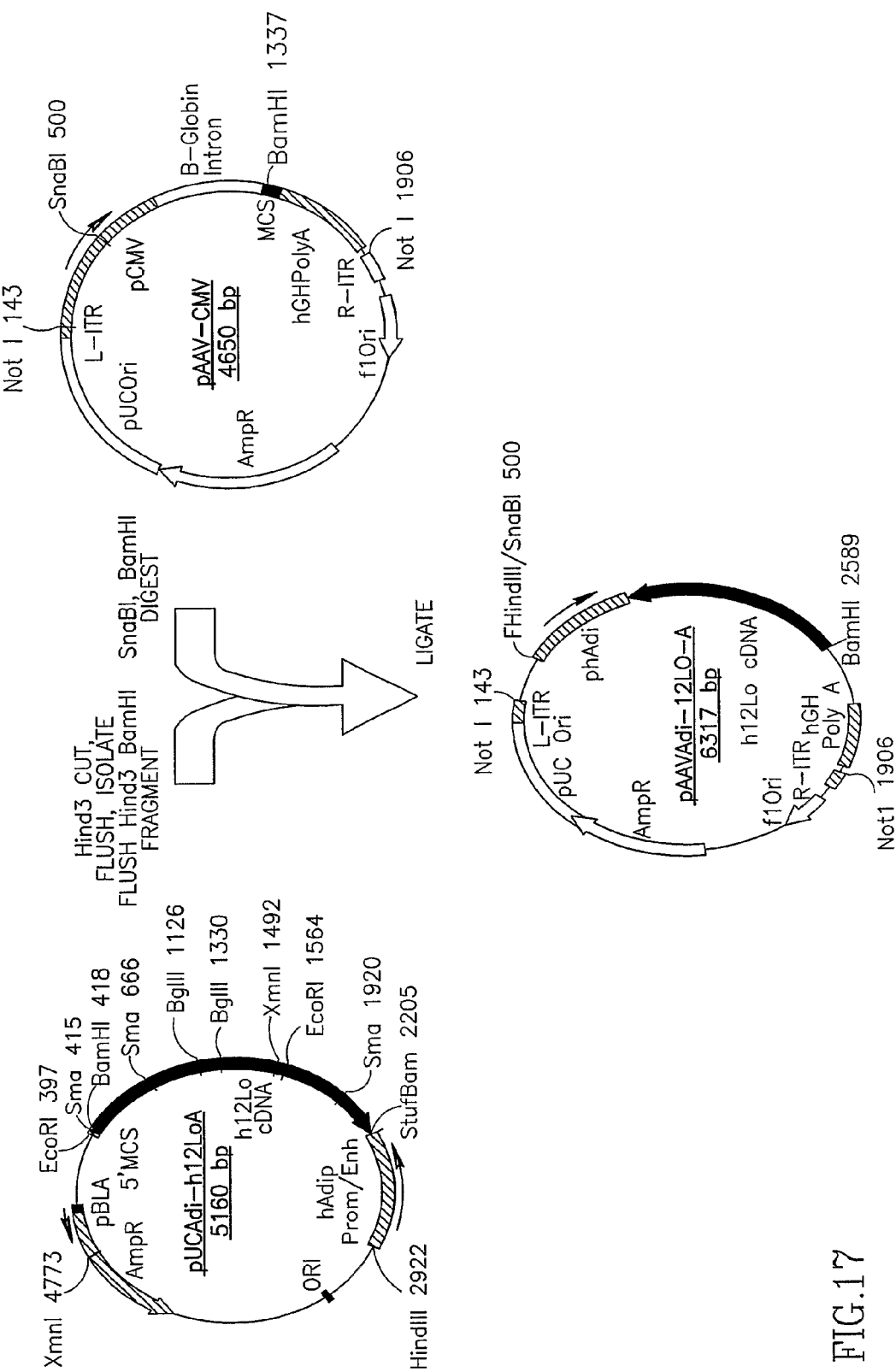
FIG. 17 demonstrates construction of Adiponectin Driven h12Lipoxygenase knockout plasmid GutLess AAV Shuttle Vector.
Figure 18A:
FIG. 18A illustrates human adiponectin promoter/enhancer.
Figure 18B:
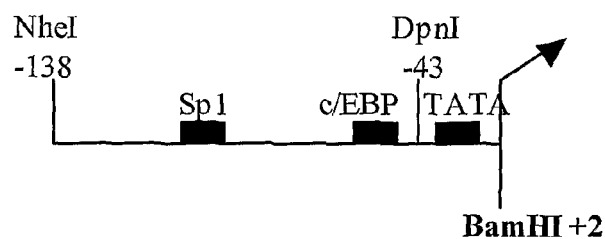
FIG. 18B illustrates human leptin promoter/enhancer.
Figure 18C:
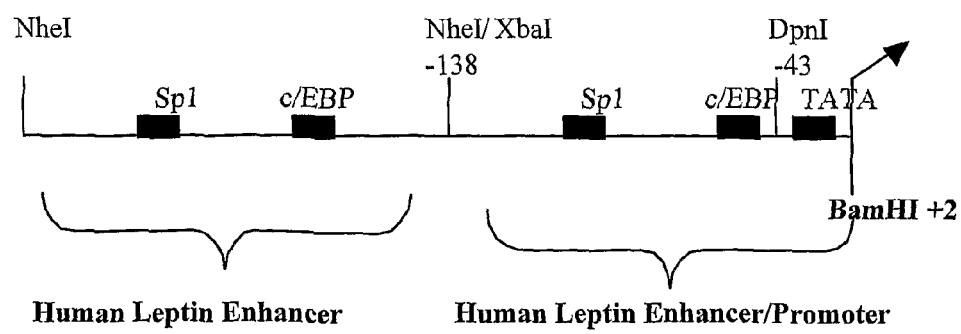
FIG. 18C illustrates the recombinant human leptin promoter/double leptin enhancer. Restriction sites (HindIII, HgaI, BamHI, NheI, DpnI and XbaI) and binding sites of transcription factors (c/EBP, Sp1, SREBP) are indicated. Arrowheads indicate transcription initiation sites.

Construction of an Adiponectin Driven h-12Lipoxygenase Antisense Knockout Plasmid Vector A number of peptides, including hormones, such as adiponectin, are exclusively expressed by adipocytes. Hence, the minimum promoter of adiponectin or any of the other fat-specific proteins, may be useful to direct the antisense knockout of 12 lipoxygenase to human fat cells. To examine this notion in cultured human and mouse preadipocytes as well as adipocytes, a plasmid vector was prepared as illustrated in FIG. 16.

As detailed above, the constitutively expressed CMV 12-Lo (600A and mp12LoA) smaller antisense knockout vectors effectively (to different degrees) induce apoptosis in 3T3-L1 cells. An adipose tissue specific near full length human 12-Lo antisense knockout plasmid was created as the next step.

The minimum 717 bp Hind3 (−676)-BamHI (+41) human adiponectin promoter/enhancer (Kita et al., 2005; SEQ ID NO: 4) was isolated and the BamHI end (which left a 5' overhang) was specifically filled in with the Klenow fragment of E. coli DNA polymerase. In parallel to this the ph12LO-183/pUC19 (FIG. 16) was cut with the two restriction enzymes, StuI and Hind3. This would also produce a linearized DNA molecule with a flush end (Stu1) as well as an open Hind3 end, complementary to the adiponectin promoter/enhancer. These two fragments were then ligated together producing the 5160 bp plasmid pUCAdi-h12LoA (see FIG. 16) with the adiponectin promoter/enhancer (designated "hAdip-Prom/Enh") orientated in the antisense orientation to the 12-Lo cDNA (designated "h12LocDNA").

For stable expression of stable 12Lo antisense RNA, a eukaryotic poly-A addition signal should be inserted at the end of the putative mRNA expression cassette. For this purpose the 268 bp PmeI-PvuII bovine growth factor poly-A addition signal (designated "BGH pA") was isolated from the pcDNA3.1+ vector (Invitrogen, Paisley, UK) and inserted into BamH1 cut and Klenow DNA Polymerase filled in pUCAdi-h12LoA, described above (see FIG. 16). As this poly-A addition signal functions in either orientation the resulting 5428 bp plasmid pUCAdi-h12LoA-pA should efficiently produce 12-Lo antisense poly-A mRNA in adipocyte cells in culture following FuGene 6 (Roche, Mannheim, Germany) lipofection (as we have described in an earlier example). This expression should be limited to only adipocyte cells of human FAT origin.

The nucleic acid sequence of bovine growth hormone Poly A signal (SEQ ID NO: 6) is presented below:

GTTTAAACCCGCTGATCAGCCTCGACTGTGCCTTCTAGTTGCCAGCCA

TCTGTTGTTTGCCCCTCCCCCGTGCCTTCCTTGACCCTGGAAGGTGCC

ACTCCCACTGTCCTTTCCTAATAAAATGAGGAAATTGCATCGCATTGT

CTGAGTAGGTGTCATTCTATTCTGGGGGGTGGGGTGGGGCAGGACAGC

AAGGGGGAGGATTGGGAAGACAATAGCAGGCATGCTGGGGATGCGGTG

GGCTCTATGGCTTCTGAGGCGGAAAGAACCAGCTG

The nucleic acid sequence of the resulting plasmid, pUCAdi-h12LoA-pA (SEQ ID NO: 5), is presented below:

tcgcgcgtttcggtgatgacggtgaaaacctctgacacatgcagctcc cggagacggtcacagcttgtctgtaagcggatgccgggagcagacaag cccgtcagggcgcgtcagcgggtgttggcgggtgtcgggctggctta actatgcggcatcagagcagattgtactgagagtgcaccatatgcggt gcgaaataccgcacagatgcgtaaggagaaaataccgcatcaggcgcc attcgccattcaggctgcgcaactgctgggaagggcgatcggtgcggg cctcttcgctattacgccagctggcgaaaggggggatgtgctgcaaggc gattaagttgggtaacgccagggttttcccagtcacgacgtcgtaaaa cgacggccagtgaattcgagctcggtacccgggcagccggttctttcc gcctcagaagccacagagcccaccgcatccccagcatgcctgccattg tcttcccaatccccccttgctgtcctgccccaccccacccccaga acagaatgacacctactcagacaatgcgatgcaatttcctcattttat taggaaaggacagtgggagtggcaccttccagggtcaaggaaggcacg ggggaggggcaaacaacagatggctggcaactagaaggcacagtcgag gctgaccagcgggtttagcttggagatcctctagagtcgacctgcagg ggggggggggggggggggggcggctcccctcgcctaagctgctggg ggnnnnnnnnnnnnnnnnnnnnnnnnnnnnnnnnnnnnnnnnnnnnnn nnnnnnnnnnnnnnnnnnnnnnnnnnnnnnnnnnnnnnnnnnnnnnnn nnnnnnnnnnnnnnnnnnnnnnnnnnnnnnnnnnnnnnnnnnnnnnnn nnnnnnnnnnnnnnnnnnnnnnnncccgggaatcgcacaggacccggc tcccctcgcccaagctgccggggggcgccatgggccgccaccgcatcc gcgtggccaccggggcccggctctcctccggccgcacaacgcgtgc agccttggccggccgggacgcgcggggaggcggagccggagctgcagc tgcggccggcgcggggcgaggaggaggagtttgatcatgacgttgcag aggacttggggctcctgcagttcgtgaggctgcgcaagcaccactggc tggtggacgacgcgtggttctgcgaccgcatcacggtgcagggcccg gagcctgcgcggaggtggcccccccgtgctaccgtggtgcgcagggcg aggacatcctgagcctgcccgagggcaccgccccgcctgccaggagaca atgctttggacatgttccagaagcatcgagagaaggaactgaaagaca gacagcagatctactgctgggccacctggaaggaaggttaccctga ccatcgctgcagaccgtaaggatgacctacctccaaatatgagattcc atgaggagaagaggctggaccttgaatggacaccgaaggcagggctc tggagacggccctcaaacgtgtctacaccctcctgagctcctggaact gcctagaagactttgatcagatcttctggggccagaagagtgccctgg ctgagaaggttcgccagtgctggcaggatgatgagttgttcagctacc agttcctcaacggtgccaacccacgctgttgagacgctcgacctctc tgccctccaggctagtgctgccctcagggatggaagagcttcgggctc aactggagaaagaacttcagaatggttccctgtttgaagctgacttca tccttctggatggaattccagccaacgtgatccgaggagagaagcaac acctggctgccccctcgttatgctgaagatggagcccaatgggaagc tgcagcccatggtcatccagattcagcctcccaaccccagctctccaa ccccaacactgttcctgccctcagacccccacttgcctggctcctgg caaagtcctgggtccgaaattcagatttccaactgcacgagatccagc atcacctgctgaacacgcacctggtggctgaggtcatcgctgtcgcca ccatgcggtgcctcccaggactgcaccccatcttcaagttcctgatcc cccacatccgctacaccatggaaatcaacacccgggcccggacccaac -continued

```
tcatctcagatggaggaattttttgataaggcagtgagcacaggtggag ggggccatgtacagttgctccgtcgggcggcagctcagctgacctact gctccctctgtcctcctgacgacctggctgaccggggcctgctgggac tcccaggtgctctctatgcccacgacgctttacggctctgggagatca ttgccaggtatgtggaggggatcgtccacctcttctaccaaagggatg acatagcgaaggggacccctgagctgcagatcctctggtatggaatca gaaccacagactgcagtcagaatggaagtgaggaggagatggcccagc ctcaacagcctggtactcacggggcaggcagtccccacctcacaatt gtcatttcccattggccaactcagtgagggccagaggccggtgggcag gcacatgtccctggcagttgcccacagcctgcaccctagggaacctgg tacaacccagcttgggcttcggaagccaagtggagcttcagtcaaagc acttgtgtttccaggccttgaccttattttgcctcctacaacagcaa cagaagatggggcaaaagtcaaaccacagcaggaaaacaagattttt ttcctgcatctgacggagaaacttcctaatgtaaatgaattaattgct cagtggtccaggaggtctcccctcccatagatttgccctaataagtc agggacgccaattatcacaccacagtcttgctcactgtgcatgattgt ctgagactgtgtacgttcagacagtgagtgcttcagaagggaggactg tcagaggggtctgcaatcaggtaagaaatagagcacatcctccactct ctgacctggaccctggatttaggaaagaccttgcacatgaattctgag aactggggtgtggggaagttcctggagtggtgtggggcttggcaagtt aaaaaggccctgaattcttaaagcttggcgtaatcatggtcatagctg tttcctgtgtgaaattgttatccgctcacaattccacacaacatacga gccggaagcataaagtgtaaagcctggggtgcctaatgagtgagctaa ctcacattaattgcgttgcgctcactgcccgctttccagtcgggaaac ctgtcgtgccagctgcattaatgaatcggccaacgcgcgggagaggc ggtttgcgtattgggcgctcttccgcttcctcgctcactgactcgctg cgctcggtcgttcggctgcggcgagcggtatcagctcactcaaaggcg gtaatacggttatccacagaatcaggggataacgcaggaaagaacatg tgagcaaaaggccagcaaaaggccaggaaccgtaaaaaggccgcgttg ctggcgtttttccataggctccgcccccctgacgagcatcacaaaaat cgacgctcaagtcagaggtggcgaaacccgacaggactataaagatac caggcgtttccccctggaagctccctcgtgcgctctcctgttccgacc ctgccgcttaccggatacctgtccgcctttctcccttcgggaagcgtg gcgctttctcatagctcacgctgtaggtatctcagttcggtgtaggtc gttcgctccaagctgggctgtgtgcacgaaccccccgttcagcccgac cgctgcgccttatccggtaactatcgtcttgagtccaacccggtaaga cacgacttatcgccactggcagcagccactggtaacaggattagcaga gcgaggtatgtaggcggtgctacagagttcttgaagtggtggcctaac tacggctacactagaaggacagtatttggtatctgcgctctgctgaag ccagttaccttcggaaaaagagttggtagctcttgatccggcaaacaa
```

-continued

```
accaccgctggtagcggtggttttttgtttgcaagcagcagattacg cgcagaaaaaaaggatctcaagaagatcctttgatcttttctacgggg tctgacgctcagtggaacgaaaactcacgttaagggattttggtcatg agattatcaaaaaggatcttcacctagatccttttaaattaaaaatga agttttaaatcaatctaaagtatatatgagtaaacttggtctgacagt taccaatgcttaatcagtgaggcacctatctcagcgatctgtctattt cgttcatccatagttgcctgactccccgtcgtgtagataactacgata cgggagggcttaccatctggccccagtgctgcaatgataccgcgagac ccacgctcaccggctccagatttatcagcaataaaccagccagccga agggccgagcgcagaagtggtcctgcaactttatccgcctccatccag tctattaattgttgccgggaagctagagtaagtagttcgccagttaat agtttgcgcaacgttgttgccattgctacaggcatcgtggtgtcacgc tcgtcgtttggtatggcttcattcagctccggttcccaacgatcaagg cgagttacatgatccccatgttgtgcaaaaaagcggttagctccttc ggtcctccgatcgttgtcagaagtaagttggccgcagtgttatcactc atggttatggcagcactgcataattctcttactgtcatgccatccgta agatgcttttctgtgactggtgagtactcaaccaagtcattctgagaa tagtgtatgcggcgaccgagttgctcttgcccggcgtcaatacgggat aataccgcgccacatagcagaactttaaaagtgctcatcattggaaaa cgttcttcggggcgaaaactctcaaggatcttaccgctgttgagatcc agttcgatgtaacccactcgtgcacccaactgatcttcagcatctttt actttcaccagcgtttctgggtgagcaaaaacaggaaggcaaaatgcc gcaaaaaagggaataagggcgacacggaaatgttgaatactcatactc ttcctttttcaatattattgaagcatttatcagggttattgtctcatg agcggatacatatttgaatgtatttagaaaaataaacaaatagggtt ccgcgcacatttccccgaaaagtgccacctgacgtctaagaaaccatt attatcatgacattaacctataaaaataggcgtatcacgaggccctttt cgtc.
```

Example 9

Construction of an Adiponectin Driven h 12Lipoxygenase Antisense Knockout Gutless AAV Shuttle Vector as Well as Generated AAV Virus To apply fat tissue specific induced apoptosis by antisense knockout of 12-lipoxygenase to animal models and clinical use, a more effective in vivo methods of vector transduction may be beneficial. Traditionally, viral infection has been recognized as an effective mode of gene transduction. A number of viral gene infection systems have been developed for experimental and more recently human therapeutic use. A "safe gutless", highly efficient, non self-replicatable system allowing infection of human fat tissue, was herein constructed.

A Gutless Adeno Associated Virus (AAV) would allow the high-efficiency gene transfer necessary with increased safety over other viral-based systems. Recombinant AAV2 has a broad host range, infects both dividing and non-dividing cells and integrates into the host cell for long-term stable expression (Kay et al., 2000; Nakai et al., 2003). In the current example, Stratagene's (San Diego, Calif., USA) "AAV Helper-Free System" was modified as detailed below. The shuttle vector in this system, pAAV-MCS (see FIG. 17), contains a CMV promoter/enhancer just 5' to the multiple cloning site (MCS), which is followed by the bovine growth hormone (BGH) poly A addition signal (hGH Poly A").

As any expression cassette placed into the MCS will be constitutively expressed in most cell types, replacement of the CMV promoter/enhancer with an adipocyte specific promoter/enhancer was performed. To this end, the 5160 bp plasmid pUCAdi-h12LoA described in Example 8 (see FIG. 16) was used. The Hind III restriction site at the 5' end of the minimal human adiponectin promoter/enhancer was cut and the 5' overhang filled in using the Klenow fragment of E. coli DNA polymerase. Subsequently following BamHI digestion, a 1,787 bp hAdip-h12Lo antisense cDNA was isolated and inserted into the SnaB1, BamHI double digested pAAV-CMV AAV shuttle vector. The Flush SnaB1 restriction enzyme site is located within the CMV promoter/enhancer of pAAV-CMV and hence the release of the 737 bp SnaB1-BamHI fragment from pAAV-CMV would sufficiently destroy the CMV/enhancer/promoter to allow the phAdip promoter to promote adipocyte specific expression in the resultant AAV vector.

The resultant 6317 bp AAV shuttle vector, "pAAVAdi-12Lo-A" is then calcium phosphate (Weisinger et al., 1988) cotransfected with pAAV-RC and pHelper plasmids into the packaging HEK293 cell line. Both pAAV-RC and pHelper plasmids encode specific AAV gene products necessary for inducing lytic phase and packaging virions. Replication deficient, recombinant AAV virions are then collected from cotransfection lysates, clarified and then used for transduction of target cells in culture and in vivo. Infection conditions that are non-permissive for replication prompt the expression cassette to integrate into the genome and establish stable expression.

Example 10

Construction of Chimeric Leptin/Adiponectin Promoter/Enhancer Vectors Directed to the Large Cell Inflammatory Adipocyte, a Major Culprit in Human Severe Obesity Described herein is the preparation of a chimeric promoter/enhancer vector useful for directing enhanced gene expression preferentially in large-cell adipocytes, and its CAT and 12-Lo knockout expression vectors. The chimeric promoter/enhancer contains an adiponectin promoter/enhancer sequence as well as a leptin enhancer (containing both Sp1 and C/EBP binding sites), as detailed herein. The CAT expression vector serves as an expression control vector in order to verify that the vector per se facilitates appropriate expression in the target cells while not inducing cell death by itself.

Figure 19:
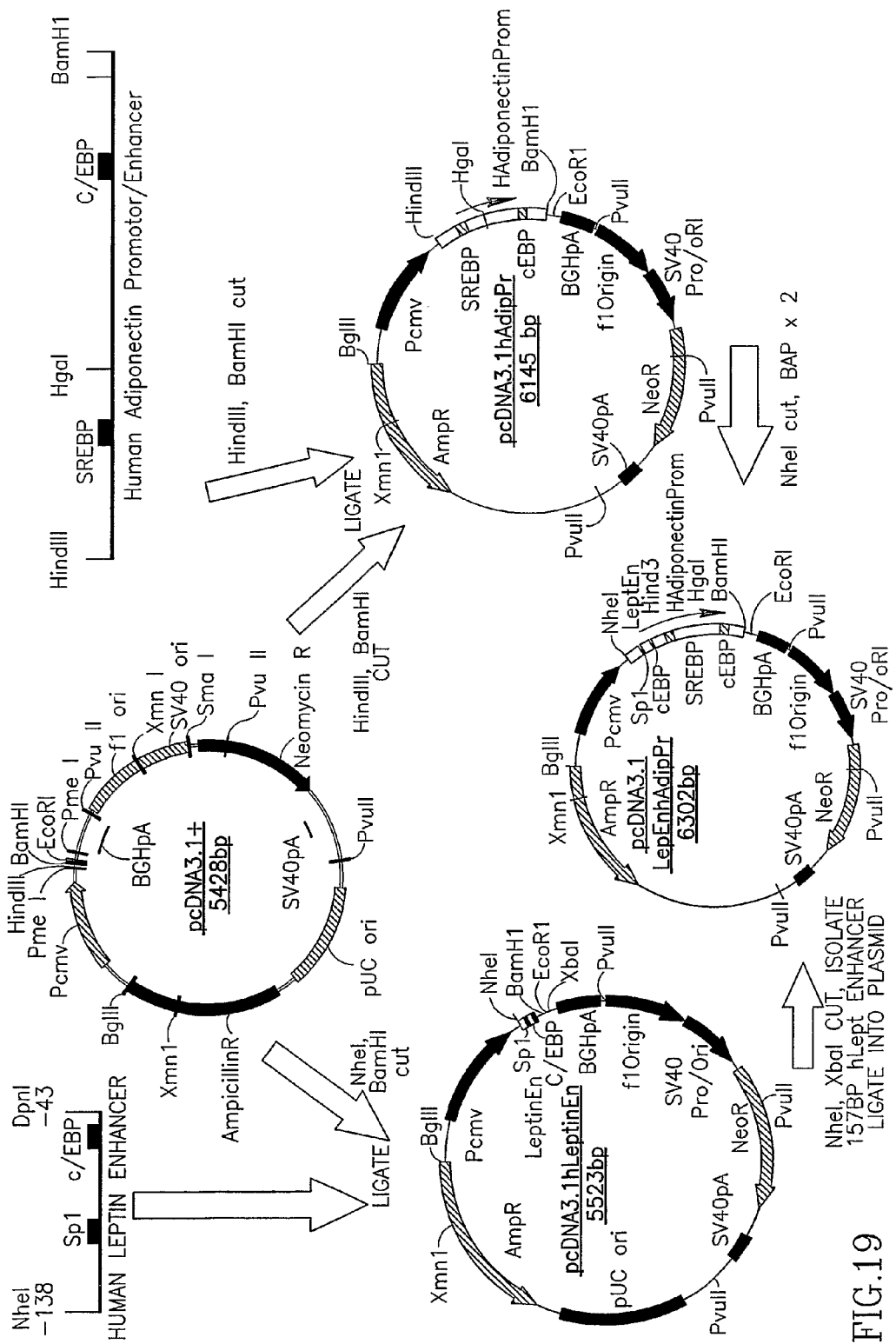
FIG. 19 illustrates construction of Leptin/Adiponectin Promoter/Enhancer driven vector.

The minimum 95 bp human leptin enhancer ("LeptEn", synthesized with an additional 3' BamHI sequence) and the minimum 768 bp human adiponectin promoter/enhancer ("HadiponectinProm") are separately cloned into the polylinker of the pcDNA3.1+ (Invitrogen) as illustrated in FIG. 19, resulting in plasmids pcDNA3.1hleptinEn and pcDNA3.1hAdipPr, respectively. The resultant 157 bp NheI-XbaI leptin enhancer fragment of pcDNA3.1hleptinEn is cloned into the NheI site of the pcDNA3.1hAdipPr plasmid and the vector with the correct orientation is selected and designated pcDNA3.1LepEnhAdipPr (see FIG. 19). The XbaI cut DNA would enter the NheI cut site but would no longer be cutable by either restriction enzyme. The resident CMV enhancer is removed by the deletion of the BglII-NheI region of the resultant pcDNA3.1LepEnhAdipPr plasmid (see FIG. 19). Specifically, following BglII and NheI restrictions, which produce 5' overhangs in the DNA, the 5' overhangs are filled in and the ends re-ligated in sufficient dilution to prevent the reentry of the cutout fragment. The chimeric Leptin/Adiponectin Promoter/Enhancer has the nucleic acid sequence as set forth in SEQ ID NO: 8.

Figure 20:
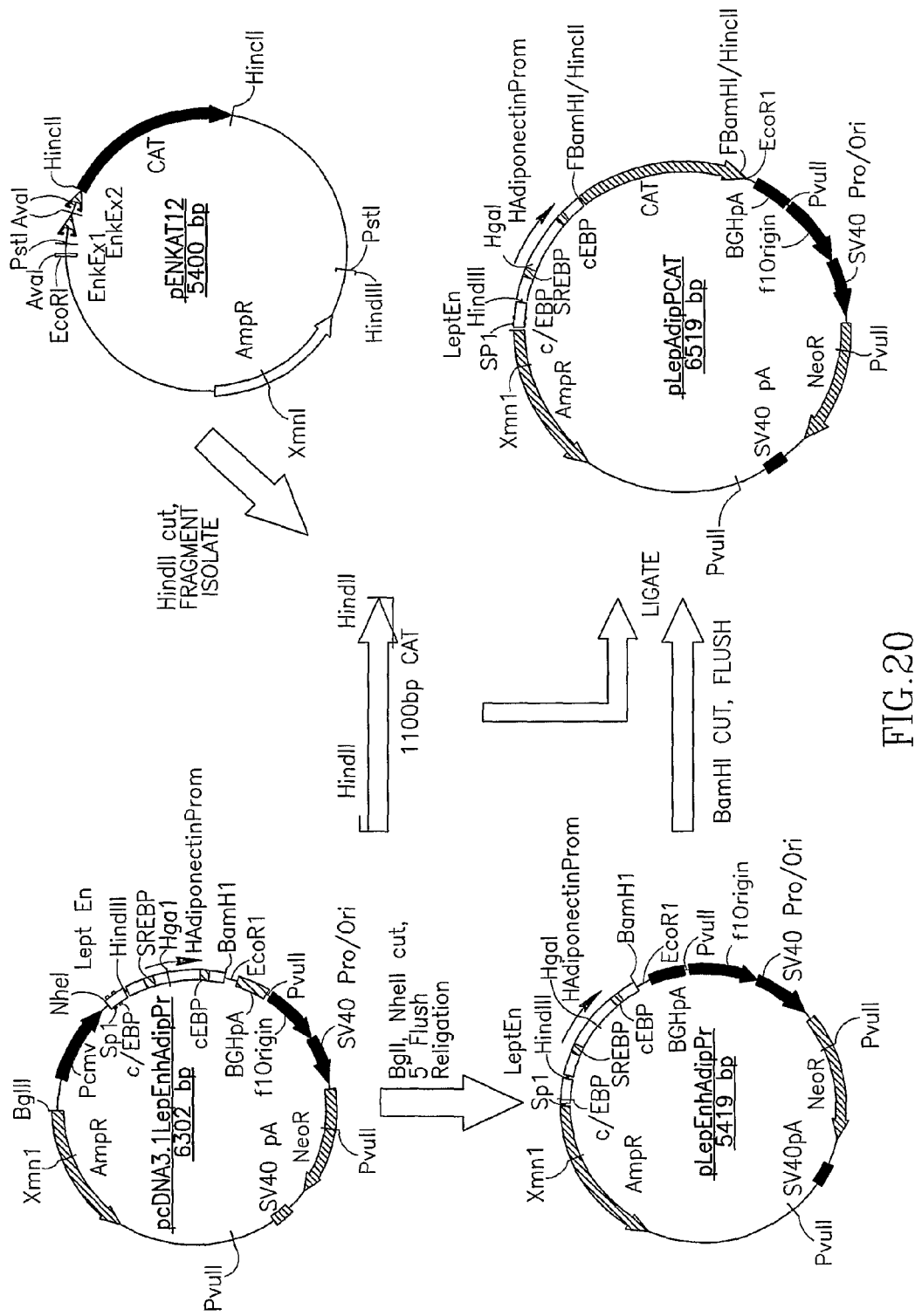
FIG. 20 illustrates construction of Leptin/Adiponectin Promoter/Enhancer driven Human CAT Expression Vector.
Figure 21:
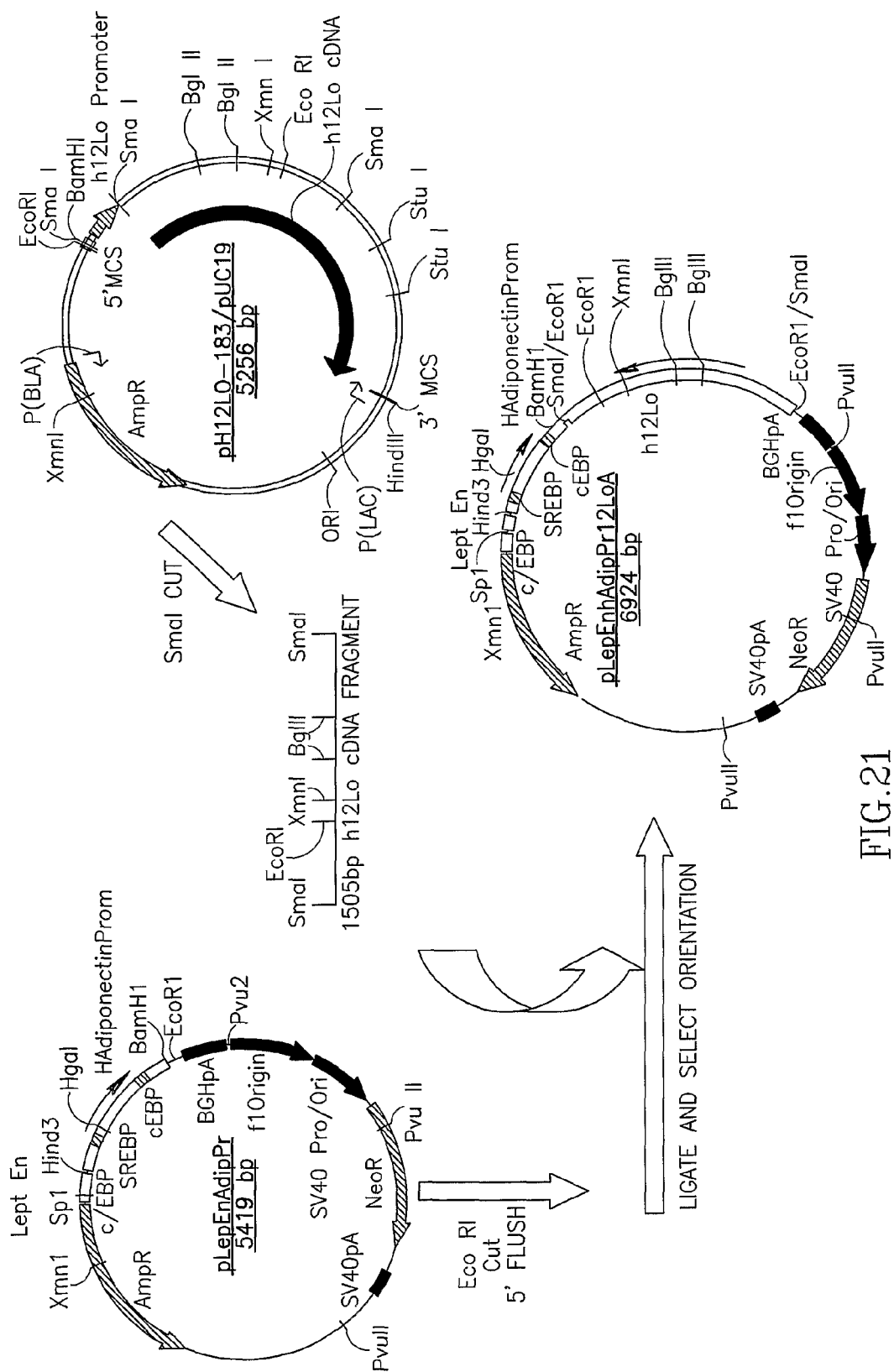
FIG. 21 illustrates construction of Leptin/Adiponectin Promoter/Enhancer driven Human 12-Lipoxygenase knockout vector.

The resulting plasmid, designated "pLepEnhAdipPr" is then used to clone the 1100 bp flush CAT cDNA into its unique flushed BamHI site in the sense orientation ("pLepEnhAdipPrCAT", FIG. 20); or the 1505 bp flush human 12-Lipoxygenase ("h12Lo") cDNA in the antisense orientation with respect to the chimeric promoter/enhancer ("pLepEnhAdipPr12LoA", FIG. 21).

The clones are examined in vitro as described in Examples 3-7. The resulting chimeric leptin/adiponectin promoter/enhancer 12-Lo expression cassette is then cloned into the gutless AAV vector as described in Example 9 herein.

Example 11

Construction of Leptin Promoter/Enhancer Vectors Directed to the Large Cell Inflammatory Adipocyte, a Major Culprit in Human Severe Obesity Described herein is the preparation of a Leptin promoter/enhancer vector and its CAT and 12-Lo knockout expression vectors. The CAT expression vector serves as an expression control vector in order to verify that the vector per se facilitates appropriate expression in the target cells while not inducing cell death by itself.

Figure 22:
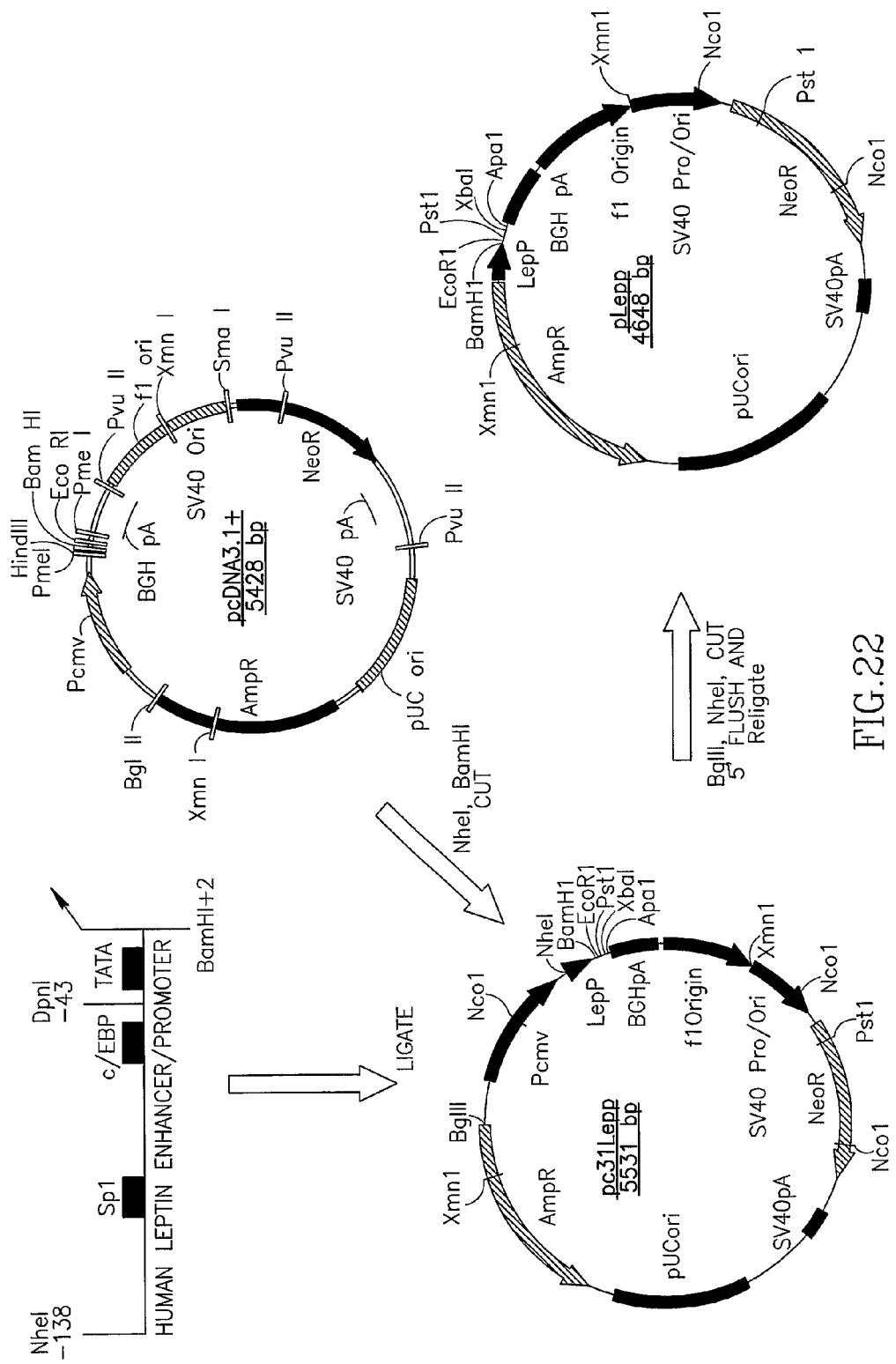
FIG. 22 illustrates construction of Leptin Promoter/Enhancer Vector.
Figure 23:
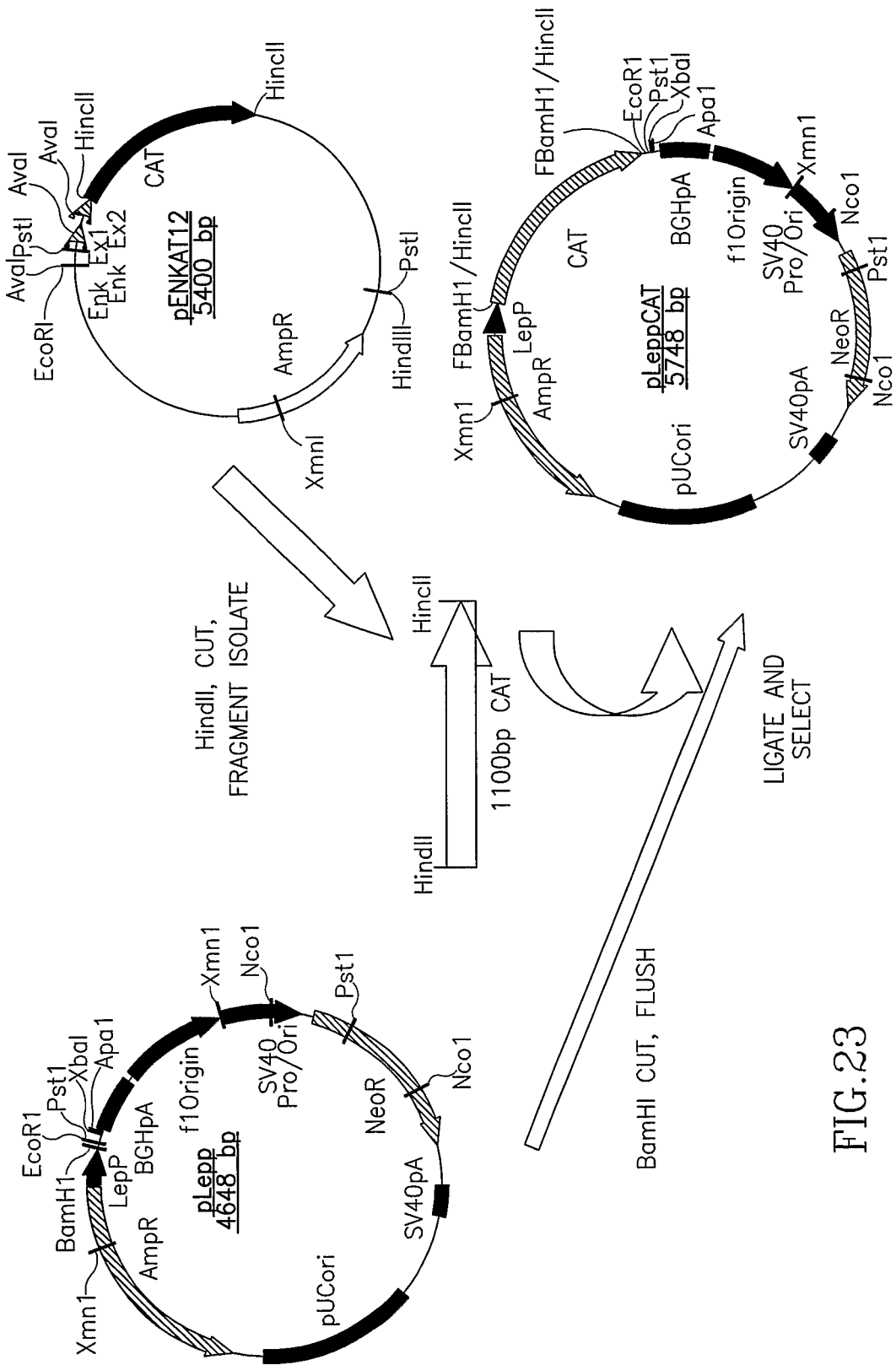
FIG. 23 illustrates construction of the Leptin Promoter/Enhancer driven human CAT Expression Vector.
Figure 24:
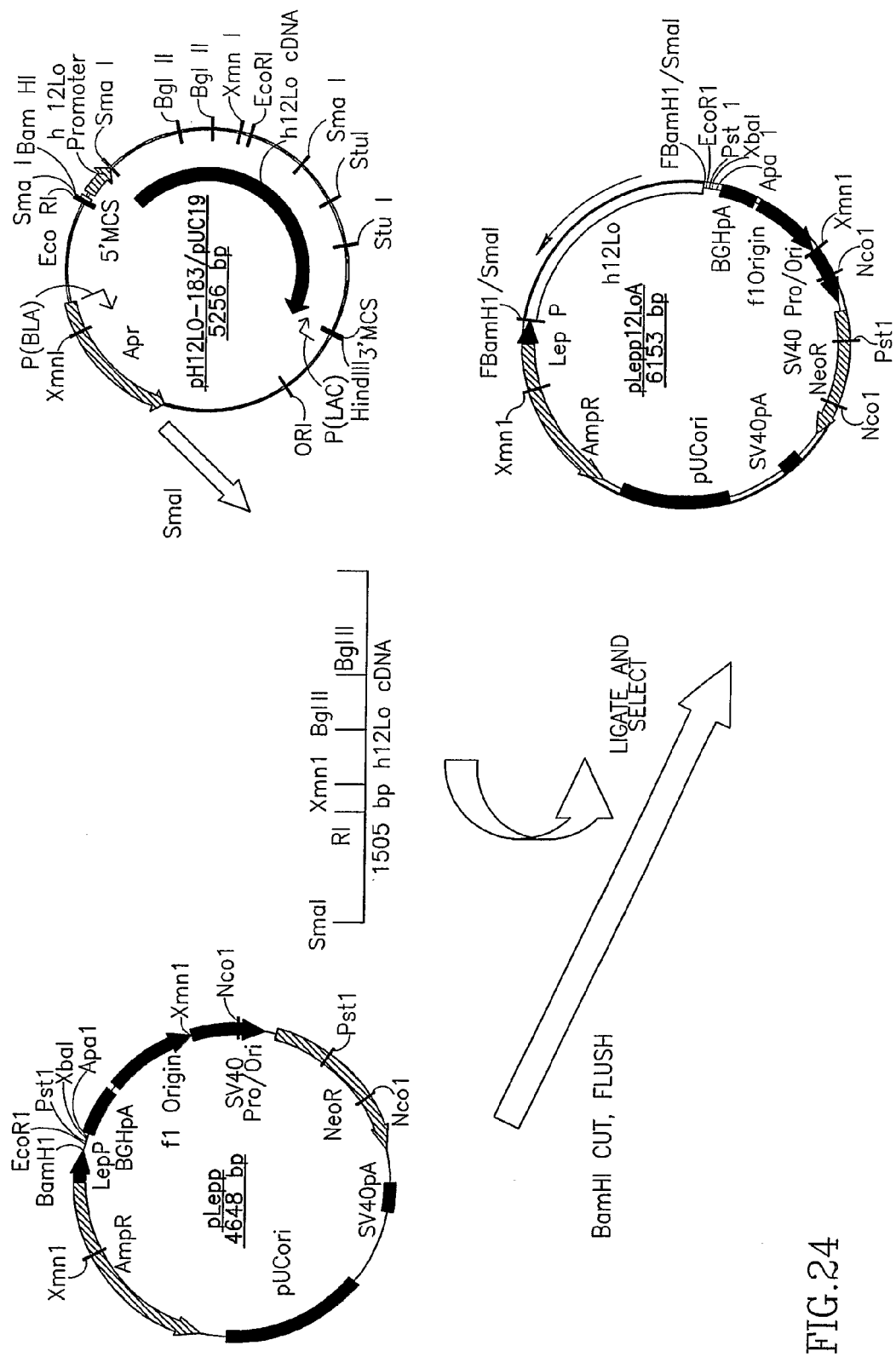
FIG. 24 illustrates construction of the Leptin Promoter/Enhancer driven Human 12-Lipoxygenase knockout vector.

The minimum 138 bp human leptin promoter/enhancer ("LepP"; SEQ ID NO: 7) is synthesized with an additional 3' BamHI sequence (GGATCC added for cloning convenience) and cloned into the polylinker of the pcDNA3.1+ (Invitrogen) as illustrated in FIG. 22. The resident CMV enhancer is removed by the deletion of the BglII-NheI region of the resultant "pc31Lepp" plasmid (see FIG. 22). Specifically, BglII and NheI restrictions are performed, which produce 5' overhangs in the DNA. These 5' overhangs are filled in and the ends re-ligated in sufficient dilution to prevent the reentry of the cutout fragment. The resulting plasmid ("pLepp") is then used to clone the 1100 bp flush CAT cDNA into its unique flushed BamHI site in the sense orientation ("pLeppCAT", FIG. 23); or the 1505 bp flush human 12-Lipoxygenase ("h12Lo") cDNA in the antisense orientation with respect to the promoter/enhancer ("pLepp12LoA", FIG. 24).

The clones are examined in vitro as described in Examples 3-7. The resulting leptin enhancer/promoter 12-Lo expression cassette is then cloned into the gutless AAV vector as described in Example 9 herein.

Example 12

Construction of a Double Leptin Enhancer Single Leptin Promoter Family of Vectors Directed to the Large Cell Inflammatory Adipocyte, a Major Culprit in Human Severe Obesity Described herein is the preparation of a double leptin enhancer, single promoter vector and its CAT and 12-Lo knockout expression plasmid vectors. It has been reported, that Leptin gene expression and promoter activity is greatly increased as mature adipocytes increase in size, as found in isolates for individuals with clinically significantly greater BMIs (obese BMI >30). The vector contains a recombinant leptin promoter comprising a leptin promoter/enhancer and an additional enhancer (containing both Sp1 and C/EBP binding sites) sequence, and promotes enhanced expression in large cell adipocytes. The CAT expression vector serves as an expression control vector in order to verify that the vector per se facilitates appropriate expression in the target cells while not inducing cell death by itself.

Figure 25:
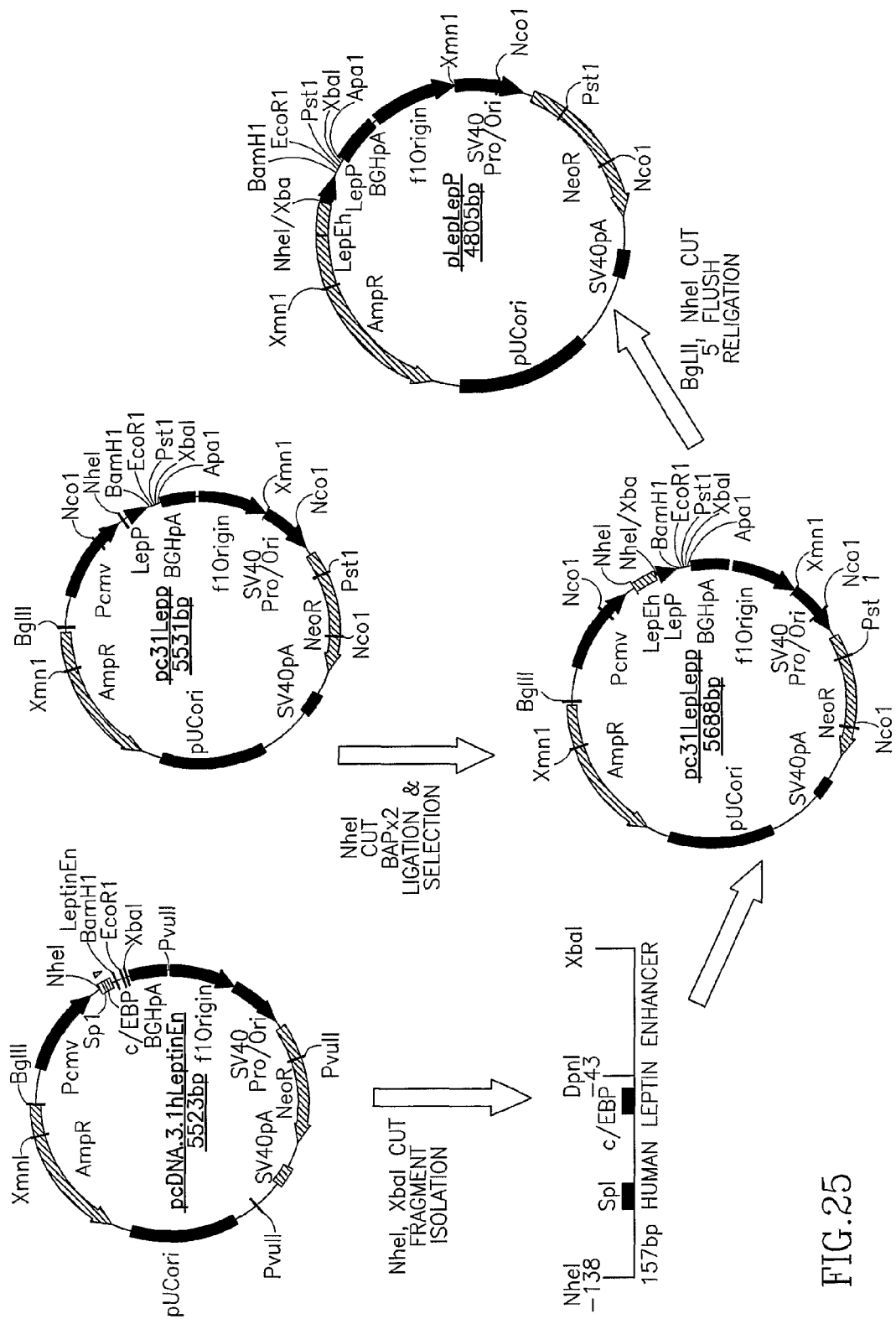
FIG. 25 illustrates construction of the Double Enhancer, Single Leptin Promoter Vector.
Figure 26:
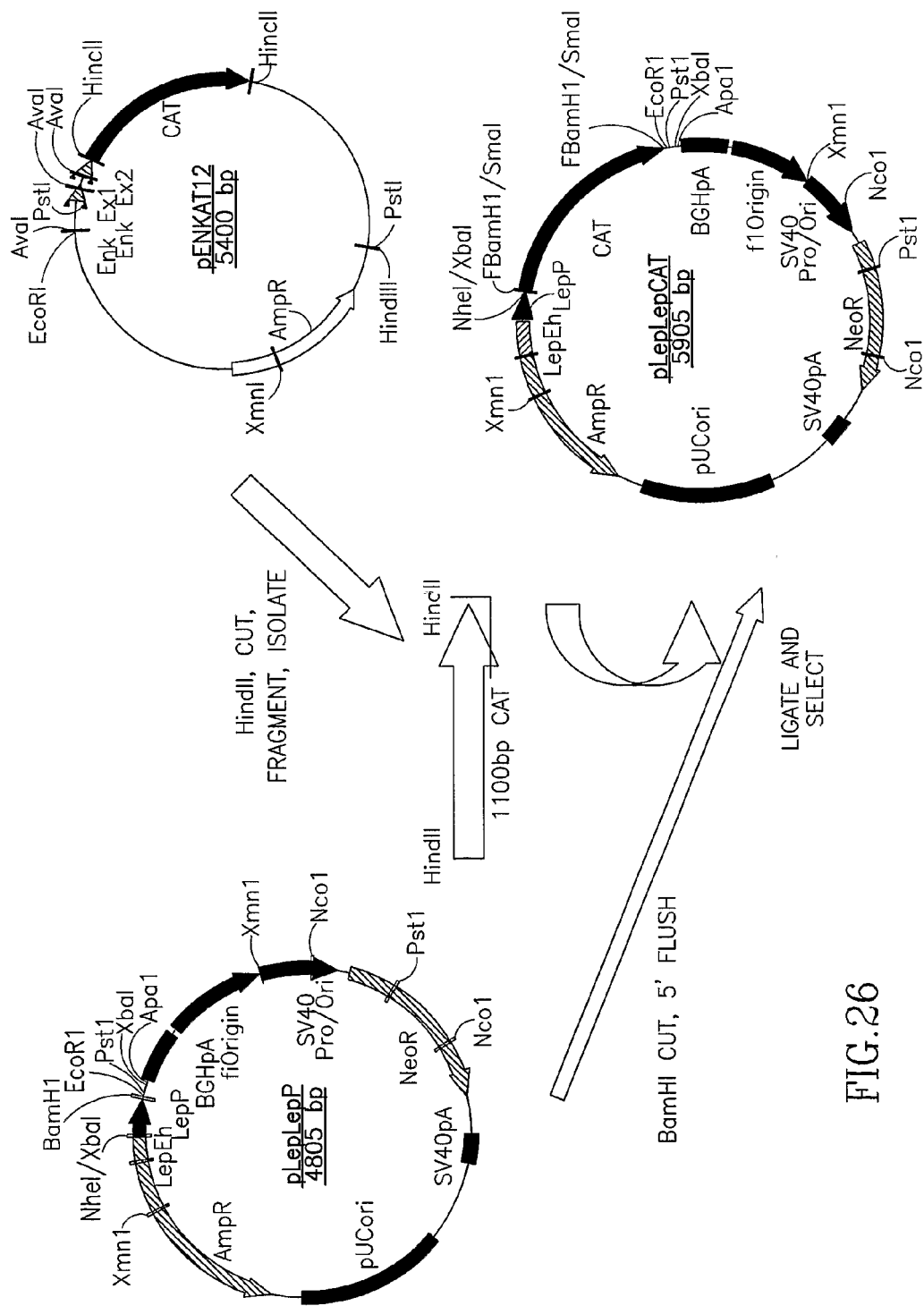
FIG. 26 illustrates construction of the Double Enhancer, Single Leptin Promoter driven CAT Expression Vector.

The 157 bp NheI-XbaI human leptin enhancer DNA fragment derived from plasmid pcDNA3.1hLeptinEn ("LepEh", see Example 10; FIG. 19), is cloned into the NheI site of plasmid "pc31Lepp" (see Example 11; FIG. 22) and selected for sense orientation, to produce the "pc31LepLepp" plasmid (FIG. 25). The resident CMV enhancer is removed by the deletion of the BglII-NheI region of the resultant pc31LepLepP plasmid (see FIG. 24). Specifically, BglII and NheI restrictions are performed, which produce 5' overhangs in the DNA. These 5' overhangs are filled in and the ends re-ligated in sufficient dilution to prevent the reentry of the cutout fragment. The resulting plasmid ("pLepLepP") is then used to clone the 1100 bp flush CAT cDNA into its unique flushed BamHI site in the sense orientation ("pLepLepP-CAT", FIG. 26); or the 1505 bp flush human 12-Lipoxygenase ("h12Lo") cDNA in the antisense orientation with respect to the chimeric promoter/enhancer ("pLepLepP12LoA", FIG. 27).

The clones are examined in vitro as described in Examples 3-7. The resulting double leptin enhancer, single promoter 12-Lo expression cassette is then cloned into the gutless AAV vector as described in Example 9 herein.

Example 13

Animal Treatment Protocol

For evaluating the in vivo efficiency and specificity of the viral vectors an animal model is used, namely the "diet-induced obesity" mouse model.

C57BL/6J mice are used for the experiments. After weaning, mice are fed standard chow diet (SCD; 4.5% w/w fat [12% of kcal from fat], 0.02% w/w cholesterol) until the age of 8 weeks. To induce obesity, mice are then switched to high-fat diet (HFD; 21% w/w fat [41% of kcal from fat], 0.15% w/w cholesterol) as of 8 weeks of age, and maintained on this diet for 24 weeks.

A. Systemic Administration

For the systemic in vivo inoculation procedures, the gutless adenoassociated viral vectors containing the various platelet-type 12-LO-directed antisense constructs (Examples 9-12) $2 \times 10^8$ plaque-forming virus units (cfu's) (AAV-anti12LO) or their respective gutless adenoassociated viral control CAT vectors (AAV-CAT) are injected into the jugular vein of mice. Weight is monitored daily; total percent body fat is measured by dual-energy X-ray absorptiometry (DEXA) using the PIXIMUS mouse densitometry apparatus (Lunar Corporation, Madison, Wis., USA). Mice are euthanized 7, 14 or 21 days following inoculation, and fat tissue samples are collected for further analysis from the subcutaneous, visceral and pericardial depots. Total body fat is assessed; tissue is then divided into three pools: one for histological analysis, one for cell preparation and one for tissue gene and protein expression assays.

Histological Analysis

Histological assays are performed for assessing adipocyte size, apoptotic markers and the amount of inflammatory cells (e.g., macrophages) in the tissue sample. Adipocyte size is assessed using a computerized digital analysis. The presence of inflammatory cells is assessed via immunohistochemistry using specific antibodies to the macrophage markers CD68, MAC-1/CD11b, and F4/80, and the macrophage/adipocyte ratio is calculated. Fat accumulation is quantified by oil red staining. CAT immunostaining is used as a control for inoculation efficiency. Additionally, the expression of platelet-type 12LO is estimated using specific anti-mouse platelet 12-LO antibodies, according to standard immunohistochemistry protocols.

Cell Preparation

In the cell preparation procedure, cells are isolated and fractionated into adipocytes and stromal/vascular (S/V) cells by collagenase digestion, following initial mechanical mincing. The resulting digest is filtered through a 250-µm chiffon mesh, and the floating adipocytes separated from S/V cells pelleted by centrifugation at 500×g for 5 min. The size of fat cells is measured by direct microscopic determination, with the mean adipocyte diameter calculated from measurements of 100 cells per depot site.

Further characterization of the harvested cells is then conducted by fluorescence-activated cell sorting (FACS) analysis. To this end, cells are labeled with fluorescein isothiocyanate- or phycoerythrin-conjugated anti-mouse CD68, MAC-1/CD11b, F4/80 S/V, CD3, or CD11c antibodies (BD Pharmingen, San Diego, Calif.) for inflammatory cells, or anti-leptin antibodies for mature adipocytes. Analysis is performed by FACScan and using the CellQuest software. Finally, flow cytometry is also used to examine cell cycle and the relative adipocyte apoptotic population in mice treated by the AAV-12LO or by the control AAV-CAT vector.

RNA and Protein Extraction

In fat tissue retained for gene and protein expression, tissue is separately extracted for mRNA and protein. The extracts are used for determining the expression of 12-LO mRNA and protein. In addition, mRNA "laddering" and a sandwich anti-histone/anti-DNA immunoassays (ELISA, Roche) are assessed as apoptotic markers.

B. Local Administration

For the assessment of local effects due to the AAV-based anti-12-LO treatment, local subcutaneous infiltration with AAV-anti-LO or AAV-CAT (at either $10^6$ or $10^7$ cfu/fat tissue), for subcutaneous fat, or intra-omental infiltrations under direct visualization during surgical laparotomy, are performed. Tissue and cell analysis at the time intervals indicated above are carried out as specified for the studies in animals receiving the systemic treatment.

REFERENCES

Allen et al., 1997. J. Pharmacol. Toxicol. Methods; 37, 215-228.
Brash, A. R., 1999. J. Biol. Chem.; 274, 23679-23682.
Connacher et al., 1992. Am J Clin Nutr. January; 55(1 Suppl): 258S-261S. Review
Degterev et al., 2003. Oncogene; 22, 8543-8567.
Della-Fera et al., 2001. Diabetes Obes Metab 3:299-310.
Ettinger et al., 2003. JAMA.; 289:1826-32.
Garg A. 2000. Am J Med; 108:143-152.
Geloen et al., 1989. Am J Physiol 257:E547-E553.
Goeptar et al., 1994. Cancer Res. 1994; 54: 2411-2418.
Gullicksen et al., 2003. Int J Obes Relat Metab Disord 27:302-312.
Hauner et al., 1989. J Clin Invest; 84:1663-1670.
He et al., 1995. J. Biol. Chem. 270, 28887-28891.

Hukshorn et al., 2002. Int J Obes Relat Metab Disord.; 26:504-9.
Jernas et al., 2006. FASEB J. 20, 1540-1542.
Kay et al, 2000. Nat. Genetics; 24, 257-261.
Kita et al., 2005. BBRC; 331, 484-490.
LaGamma et al., 1993. Cell Transplantation; 2, 207-214.
Limor et al, 2001. Hypertension; 38, 864-871.
Limor et al., 1999. J. Biochem. Biophys. Methods; 40, 57-64.
Lloreta J et al., 2002. Virchows Arch; 441:599-604.
Magun et al., 1998. Int J Obes Relat Metab Disord; 22:567-571.
Margareto et al., 2000. Life Sci 68:99-107.
Mason et al., 1998. Endocrinology 139, 1013-1022.
Moran et al., 1996. J. Pharmacol. Toxicol. Methods; 36, 41-44.
Nakai et al., 2003. Nat. Genetics; 34, 297-302.
Nelson-Dooley et al., 2005. Curr Med Chem.; 12:2215-25.
Prins et al., 1994. Biochem Biophys Res Commun; 201:500-507.
Prins et al., 1997. Clin Sci; 92:3-11.
Prins et al., 1997b. Diabetes; 46:1939-1944.
Qian et al., 1998. Endocrinology 139:791-794.
Salma et al., 2006. J. of Mol. Endocrinol. 36, 139-151.
Sambrook, J., Fritsch, E. F. and Maniatis, T. (1989) In: Molecular Cloning: a laboratory manual, 2nd ed. (New York: Cold Spring Harbor press) pp 1.21-85.
Scislowski et al., 1999. Diabetes 48(Suppl):A266.
Sjostrom et al., 1981. Int J Obes; 5:597-604.
Sorisky et al., 2000. Int J Obes Relat Metab Disord 24(Suppl 4):S3-S7.
Tong et al., 2002. Biochem. Biophys. Res. Commun.; 296, 942-948.
Weisinger et al., 1988. Oncogene; 3: 635-646.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A recombinant nucleic acid construct suitable for the treatment of humans comprising at least one adipose-specific transcription regulating sequence operably linked to at least one nucleic acid sequence, wherein the at least one nucleic acid sequence encodes an antisense molecule that is at least 95% complementary to the platelet-type lipoxygenase (platelet-type 12-LO) transcript of SEQ ID NO: 1, and specifically inhibits or reduces the expression of platelet-type 12-LO, wherein the adipose-specific transcription regulating sequence is a human adiponectin promoter and enhancer having the nucleic acid sequence as set forth in SEQ ID NO: 4.

2. A vector comprising the construct of claim 1.

3. The vector of claim 2 being a viral-based vector.

4. A host cell comprising the vector of claim 2.

5. A pharmaceutical composition comprising the construct according to claim 1 and a pharmaceutically acceptable carrier, excipient or diluent.

6. The composition of claim 5, wherein the carrier is a liposome or a recombinant virus particle.

7. A pharmaceutical composition comprising the vector according to claim 2 and a pharmaceutically acceptable carrier, excipient or diluent.

8. The vector of claim 3, wherein the viral-based vector is an adeno-associated viral-based vector.

9. The vector of claim 8, wherein the viral-based vector is a Gutless or mutant adeno-associated virus.

10. The construct of claim 1, wherein said at least one nucleic acid sequence encodes an antisense molecule that is fully complementary to the platelet-type 12-LO transcript of SEQ ID NO: 1.

11. A method for reducing obesity or for inhibiting or ameliorating an obesity-associated condition in a subject in need thereof, comprising administering to the subject an effective amount of the recombinant nucleic acid construct of claim 1; wherein the obesity-associated condition is selected from the group consisting of: cardiovascular disease, type 2 diabetes, hypertension, cancer, osteoarthritis and stroke.

12. A method for reducing fat cell mass in a subject in need thereof, comprising administering to the subject an effective amount of the recombinant nucleic acid construct of claim 1.

13. A method for inducing apoptosis specifically in a cell selected from the group consisting of adipocytes and pre-adipocytes, comprising contacting the cell with a therapeutic agent which reduces platelet-type 12-LO expression or activity, the therapeutic agent comprising the recombinant nucleic acid construct of claim 1.

14. A method for inhibiting or reducing the expression of platelet-type 12-LO in a cell selected from adipocytes or pre-adipocytes, comprising contacting the cell with a therapeutic agent which reduces platelet-type 12-LO expression or activity, the therapeutic agent comprising the recombinant nucleic acid construct of claim 1.

15. The method of claim 14, wherein the construct is administered locally to specific fat depots or is administered systemically.

* * * * *

UNITED STATES PATENT AND TRADEMARK OFFICE
CERTIFICATE OF CORRECTION

PATENT NO. : 9,279,127 B2
APPLICATION NO. : 12/513006
DATED : March 8, 2016
INVENTOR(S) : Weisinger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1160 days.

Signed and Sealed this
Twenty-first Day of June, 2016

Michelle K. Lee
*Director of the United States Patent and Trademark Office*

```
SEQUENCE LISTING

<160> NUMBER OF SEQ ID NOS: 11

<210> SEQ ID NO 1
<211> LENGTH: 559
<212> TYPE: DNA
<213> ORGANISM: Homo sapiens

<400> SEQUENCE: 1
catgaggaga agaggctgga ctttgaatgg acactgaagg cagggtgaga aaaaggctag      60
acctcgaagt gaaataaggg ctgggagggc caagaatgat gatagacggt gagggactga     120
gggatcagct gatgagttaa gcctcaatac ctgtcctagg gctctggaga tggccctcaa     180
acgtgtttac accctcctga gctcctggaa ctgcctagaa gactttgatc agatcttctg     240
gggccagaag agtgccctgg ctggtcagtg gtttccccga ggtctccata atcccttaat     300
ggcccctctg gatgactcat cacactccac agtcccccgt aactctttgc aagaaagaga     360
ccttatcata tctggtcaac tcagagaggc cttgagaatg aaaacgcaga agctgggttc     420
agggaagggt tatatacctg aaccctgg gtagattttg ggagaaggga tatgcaggct     480
gtggtacata tatcctcctt tcaccgccca ccaaagagaa gtttcgccag tgctggcagg     540
atgatgagtt gttcagcta                                                  559

<210> SEQ ID NO 2
<211> LENGTH: 888
<212> TYPE: DNA
<213> ORGANISM: Mus musculus

<400> SEQUENCE: 2
ctgcagtttg tgaaactgca caaacagcac acagttgtgg atgacgcctg gttctgcaac      60
ctcatcacag ttcaggggcc ggggacaagt gcagaggcca tgtttccctg ctaccgctgg     120
gtgcagggag agggaatcct gagcctcccg gagggacaag cccgcctggc aggagacaat     180
gccttagatg tcttccagaa gtatcgagaa aaggaactga aggaaagaca acagacctac     240
tgctgggcca cctggaaaga aggcttacct cagacaatag cagcggactg taaggatgac     300
cttcctccaa atatgagatt ccatgaggag aagagactgg actttgaatg gacgttgaag     360
```

```
gcggggttc tggaaatggg cctcaaacgt gtttataccc tcctgagaag ctggaaccat    420
ctggaagact ttgatcagat cttctggggc cagaagagtg ccttggccga gaaggttcac    480
cagtgttggc aggaagatga actctttggc taccagttcc tcaatggcgc caaccccatg    540
cttttgagac gctccacctc tctgccctcc agactggtac tgccctctgg gatggaggag    600
cttcaagctc agttggagaa agaactcaag aatggatccc tgtttgaagc tgactttatc    660
ctgctggatg gaattccagc taatgtgatc gaggagaac cacagtacct ggctgcccct    720
cttgtcatgc tgaggatgga ccccggtggg aagctgctac ccatggctat ccagattcag    780 cccctaacc ccagctcccc agctccaaca ctgttcctgc cctcggatcc tccacttgcc    840
tggctcttgg ctaagatctg ggtccgaaat tcagatttcc aactgcag    888
```

```
<210> SEQ ID NO 3
<211> LENGTH: 2335
<212> TYPE: DNA
<213> ORGANISM: Homo sapiens

<400> SEQUENCE: 3
cggctcccct cgcctaagct gctggggggcg ccatgggccg ctaccgcatc cgcgtggcca    60
ccggggcctg gctcttctcc gggtcgtaca accgcgtgca gctttggctg gtcgggacgc    120
gcggggaggc ggagctggag ctgcagctgc ggcggcgcg gggcgaggag gaggagtttg    180
atcatgacgt tgcagaggac ttggggctcc tgcagttcgt gaggctgcgc aagcaccact    240
ggctggtgga cgacgcgtgg ttctgcgacc gcatcacggt gcagggccct ggagcctgcg    300
cggaggtggc cttcccgtgc taccgctggg tgcagggcga ggacatcctg agcctgcccg    360
agggcaccgc ccgcctgcca ggagacaatg cttttggaca tgttccagaag catcgagaga    420 aggaactgaa agacagacag cagatctact gctgggccac ctggaaggaa gggttacccc    480
tgaccatcgc tgcagaccgt aaggatgatc tacctccaaa tatgagattc catgaggaga    540
agaggctgga ctttgaatgg acactgaagg caggggctct ggagatggcc ctcaaacgtg    600
tttacaccct cctgagctcc tggaactgcc tagaagactt tgatcagatc ttctggggcc    660
agaagagtgc cctggctgag aaggttcgcc agtgctggca ggatgatgag ttgttcagct    720
accagttcct caatggtgcc aaccccatgc tgttgagacg ctcgacctct ctgccctcca    780
ggctagtgct gccctcaggg atggaagagc ttcgggctca actggagaaa gaacttcaga    840
atggttccct gtttgaagct gacttcatcc ttctggatgg aattccagcc aacgtgatcc    900
gaggagagaa gcaatacctg gctgccccc tcgttatgct gaagatggag cccaatggga    960
agctgcagcc catggtcatc cagattcagc ctcccaaccc cagctctcca accccaacac    1020
tgttcctgcc ctcagacccc ccacttgcct ggctcctggc aaagtcctgg gtccgaaatt    1080
cagatttcca actgcacgag atccagtatc acttgctgaa cacgcacctg gtggctgagg    1140
tcatcgctgt cgccaccatg cggtgcctcc caggactgca cccatcttc aagttcctga    1200 tcccccatat ccgctacacc catggaaatc aacacccggg cccggaccca actcatctca    1260
gatggaggaa ttttttgataa ggcagtgagc acaggtggag ggggccatgt acagttgctc    1320
cgtcgggcgg cagctcagct gacctactgc tccctctgtc ctcctgacga cctggctgac    1380
cggggcctgc tgggactccc aggtgctctc tatgcccatg atgctttacg gctctgggag    1440
atcattgcca ggtatgtgga ggggatcgtc cacctcttct accaaaggga tgacatagtg    1500
aagggggacc ctgagctgca ggcctggtgt cgggagatca cggaggtggg gctgtgccag    1560
```

```
gcccaggacc gaggtttccc tgtctccttc cagtcccaga gtcaactctg ccatttcctc    1620
accatgtgcg tcttcacgtg cactgcccag catgccgcca tcaaccaggg ccagctggac    1680
tggtatgcct gggtccctaa tgctccatgc acaatgcgga tgccccacc caccaccaag     1740 gaagatgtga cgatggccac agtgatgggg tcactacctg atgtccggca ggcctgtctt    1800
caaatggcca tctcatggca tctgagtcgc cgccagccag acatggtgcc tctggggcac    1860
cacaaagaaa atatttctc aggccccaag cccaaagctg tgctaaacca attccgaaca     1920
gatttggaaa agctggaaaa ggagattaca gcccggaatg agcaacttga ctggccctat    1980
gaatatctga agcccagctg catagagaac agtgtcacca tctgagccct agagtgactc    2040
tacctgcaag atttcacatc agctttagga ctgacatttc tatcttgaat tcatgctttt    2100
cctaaagtct ctgctgctaa ggctctattt cctcccccag ttaaacccc tacattagta    2160 tcccactagc caggggagc agtaaacttt ctctgcaaag actagatcct ttttacgct     2220 ttgcagaccg catagtcact gtctcaacta ctcagctctc ctgctgcagc atgaaggcag    2280
ccacagacaa catggaaatg agtgtgacta tgttccaata aaactttatg gacac         2335

<210> SEQ ID NO 4
<211> LENGTH: 721
<212> TYPE: DNA
<213> ORGANISM: Artificial
<220> FEATURE:
<223> OTHER INFORMATION: synthetic oligonucleotide - human adiponectin
      promoter and enhancer

<400> SEQUENCE: 4
aagctttaag aattcagggc cttttttaact tgccaagccc cacaccactc caggaacttc    60
cccacacccc agttctcaga attcatgtgc aaggtctttc ctaaatccag ggtccaggtc    120
agagagtgga ggatgtgctc tatttcttac ctgattgcag acccctctga cagtcctccc    180
ttctgaagca ctcactgtct gaacgtacac agtctcagac ttaatcatgc acagtgagca    240
agactgtggt gtgataattg gcgtccctga cttattaggg caaatctatg ggaggggag     300 acctcctgga ccactgagca attaattcat ttacattagg aagtttctcc gtcagatgca    360 ggaaaaaat cttgtttttcc tgctgtggtt ttgacttttg ccccatcttc tgttgctgtt    420
gtaggaggca aaataagggt caaggcctgg aaacacaagt gctttgactg aagctccact    480
tggcttccga agcccaagct gggttgtacc aggttcccta gggtgcaggc tgtgggcaac    540
tgccagggac atgtgcctgc ccaccggcct ctggccctca ctgagttggc caatgggaaa    600
tgacaattgt gaggtgggga ctgcctgccc ccgtgagtac caggctgttg aggctgggcc    660
atctcctcct cacttccatt ctgactgcag tctgtggttc tgattccata ccagaggatc    720
c                                                                    721

<210> SEQ ID NO 5
<211> LENGTH: 5428
<212> TYPE: DNA
<213> ORGANISM: Artificial
<220> FEATURE:
<223> OTHER INFORMATION: synthetic polynucleotide - recombinant plasmid
      pUCAdi-h12LoA-pA
<220> FEATURE:
<221> NAME/KEY: misc_feature
<222> LOCATION: (771)..(936)
<223> OTHER INFORMATION: n is a, c, g, t or u

<400> SEQUENCE: 5
tcgcgcgttt cggtgatgac ggtgaaaacc tctgacacat gcagctcccg gagacggtca    60
```

```
cagcttgtct gtaagcggat gccgggagca gacaagcccg tcaggcgcg tcagcgggtg      120 ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cgagctcggt acccgggcag      420
ctggttcttt ccgcctcaga agccatagag cccaccgcat ccccagcatg cctgctattg      480
tcttcccaat cctccccctt gctgtcctgc ccaccccac cccccagaat agaatgacac      540
ctactcagac aatgcgatgc aatttcctca ttttattagg aaaggacagt gggagtggca      600
ccttccaggg tcaaggaagg cacggggag gggcaaacaa cagatggctg caactagaa      660 ggcacagtcg aggctgatca gcgggtttag cttggagatc ctctagagtc gacctgcagg      720
gggggggggg gggggggggg gcggctccc ctcgcctaag ctgctggggg nnnnnnnnnn      780
nnnnnnnnnn nnnnnnnnnn nnnnnnnnnn nnnnnnnnnn nnnnnnnnnn nnnnnnnnnn      840
nnnnnnnnnn nnnnnnnnnn nnnnnnnnnn nnnnnnnnnn nnnnnnnnnn nnnnnnnnnn      900
nnnnnnnnnn nnnnnnnnnn nnnnnnnnnn nnnnnncccg ggaatcgcac aggacccggc      960
tcccctcgcc taagctgctg gggggcgcca tgggccgcta ccgcatccgc gtggccaccg     1020 ggcctggct cttctccggg tcgtacaacc gcgtgcagct ttggctggtc gggacgcgcg     1080
gggaggcgga gctggagctg cagctgcggc cggcgcgggg cgaggaggag gagtttgatc     1140
atgacgttgc agaggacttg gggctcctgc agttcgtgag gctgcgcaag caccactggc     1200
tggtggacga cgcgtggttc tgcgaccgca tcacggtgca gggccctgga gcctgcgcgg     1260
aggtggcctt cccgtgctac cgctgggtgc agggcgagga catcctgagc ctgcccgagg     1320
gcaccgcccg cctgccagga gacaatgctt tggacatgtt ccagaagcat cgagagaagg     1380
aactgaaaga cagacagcag atctactgct gggccacctg gaaggaaggg ttaccctga      1440 ccatcgctgc agaccgtaag gatgatctac ctccaaatat gagattccat gaggagaaga     1500
ggctggactt tgaatggaca ctgaaggcag gggctctgga gatggccctc aaacgtgttt     1560
acaccctcct gagctcctgg aactgcctag aagactttga tcagatcttc tggggccaga     1620
agagtgccct ggctgagaag gttcgccagt gctggcagga tgatgagttg ttcagctacc     1680
agttcctcaa tggtgccaac cccatgctgt tgagacgctc gacctctctg ccctccaggc     1740
tagtgctgcc ctcagggatg gaagagcttc gggctcaact ggagaaagaa cttcagaatg     1800
gttccctgtt tgaagctgac ttcatccttc tggatggaat tccagccaac gtgatccgag     1860
gagagaagca atacctggct gcccccctcg ttatgctgaa gatggagccc aatgggaagc     1920
tgcagcccat ggtcatccag attcagcctc caacccccag ctctccaacc caacactgt      1980 tcctgccctc agaccccca cttgcctggc tcctggcaaa gtcctgggtc cgaaattcag     2040
atttccaact gcacgagatc cagtatcact tgctgaacac gcacctggtg gctgaggtca     2100
tcgctgtcgc caccatgcgg tgcctcccag gactgcaccc catcttcaag ttcctgatcc     2160
cccatatccg ctacaccatg gaaatcaaca cccgggcccg gacccaactc atctcagatg     2220
gaggaatttt tgataaggca gtgagcacag gtggagggg ccatgtacag ttgctccgtc     2280
gggcggcagc tcagctgacc tactgctccc tctgtcctcc tgacgacctg gctgaccggg     2340
gcctgctggg actcccaggt gctctctatg cccatgatgc tttacggctc tgggagatca     2400
```

```
ttgccaggta tgtggagggg atcgtccacc tcttctacca aagggatgac atagtgaagg   2460
gggaccctga gctgcagatc ctctggtatg aatcagaac cacagactgc agtcagaatg    2520
gaagtgagga ggagatggcc cagcctcaac agcctggtac tcacgggggc aggcagtccc   2580
cacctcacaa ttgtcatttc ccattggcca actcagtgag ggccagaggc cggtgggcag   2640
gcacatgtcc ctggcagttg cccacagcct gcaccctagg gaacctggta caacccagct   2700
tgggcttcgg aagccaagtg gagcttcagt caaagcactt gtgtttccag gccttgaccc   2760
ttattttgcc tcctacaaca gcaacagaag atggggcaaa agtcaaaacc acagcaggaa   2820
aacaagattt ttttcctgca tctgacggag aaacttccta atgtaaatga attaattgct   2880
cagtggtcca ggaggtctcc ccctcccata gatttgccct aataagtcag ggacgccaat   2940
tatcacacca cagtcttgct cactgtgcat gattgtctga gactgtgtac gttcagacag   3000
tgagtgcttc agaagggagg actgtcagag gggtctgcaa tcaggtaaga aatagagcac   3060
atcctccact ctctgacctg gaccctggat ttaggaaaga ccttgcacat gaattctgag   3120
aactggggtg tggggaagtt cctggagtgg tgtggggctt ggcaagttaa aaaggccctg   3180
aattcttaaa gcttggcgta atcatggtca tagctgtttc ctgtgtgaaa ttgttatccg   3240
ctcacaattc cacacaacat acgagccgga agcataaagt gtaaagcctg ggtgcctaa    3300
tgagtgagct aactcacatt aattgcgttg cgctcactgc ccgctttcca gtcgggaaac   3360
ctgtcgtgcc agctgcatta atgaatcggc caacgcgcgg ggagaggcgg tttgcgtatt   3420
gggcgctctt ccgcttcctc gctcactgac tcgctgcgct cggtcgttcg gctgcggcga   3480
gcggtatcag ctcactcaaa ggcggtaata cggttatcca cagaatcagg ggataacgca   3540
ggaaagaaca tgtgagcaaa aggccagcaa aaggccagga accgtaaaaa ggccgcgttg   3600
ctggcgtttt tccataggct ccgccccct gacgagcatc acaaaaatcg acgctcaagt    3660
cagaggtggc gaaacccgac aggactataa agataccagg cgtttccccc tggaagctcc   3720
ctcgtgcgct ctcctgttcc gaccctgccg cttaccggat acctgtccgc ctttctccct   3780
tcgggaagcg tggcgctttc tcatagctca cgctgtaggt atctcagttc ggtgtaggtc   3840
gttcgctcca agctgggctg tgtgcacgaa ccccccgttc agcccgaccg ctgcgcctta   3900
tccggtaact atcgtcttga gtccaacccg gtaagacacg acttatcgcc actggcagca   3960
gccactggta acaggattag cagagcgagg tatgtaggcg gtgctacaga gttcttgaag   4020
tggtggccta actacggcta cactagaagg acagtatttg gtatctgcgc tctgctgaag   4080
ccagttacct tcggaaaaag agttggtagc tcttgatccg gcaaacaaac caccgctggt   4140
agcggtggtt ttttgtttg caagcagcag attacgcgca gaaaaaaagg atctcaagaa     4200
gatcctttga tcttttctac ggggtctgac gctcagtgga acgaaaactc acgttaaggg   4260
attttggtca tgagattatc aaaaaggatc ttcacctaga tccttttaaa ttaaaaatga   4320
agttttaaat caatctaaag tatatatgag taaacttggt ctgacagtta ccaatgctta   4380
atcagtgagg cacctatctc agcgatctgt ctatttcgtt catccatagt tgcctgactc   4440
cccgtcgtgt agataactac gatacgggag ggcttaccat ctggccccag tgctgcaatg   4500
ataccgcgag acccacgctc accggctcca gatttatcag caataaacca gccagccgga   4560
agggccgagc gcagaagtgg tcctgcaact ttatccgcct ccatccagtc tattaattgt   4620
tgccgggaag ctagagtaag tagttcgcca gttaatagtt tgcgcaacgt tgttgccatt   4680
gctacaggca tcgtggtgtc acgctcgtcg tttggtatgg cttcattcag ctccggttcc   4740
caacgatcaa ggcgagttac atgatccccc atgttgtgca aaaaagcggt tagctccttc   4800
```

```
ggtcctccga tcgttgtcag aagtaagttg ccgcagtgt tatcactcat ggttatggca      4860
gcactgcata attctcttac tgtcatgcca tccgtaagat gcttttctgt gactggtgag      4920
tactcaacca agtcattctg agaatagtgt atgcggcgac cgagttgctc ttgcccggcg      4980
tcaatacggg ataataccgc gccacatagc agaactttaa aagtgctcat cattggaaaa      5040
cgttcttcgg ggcgaaaact ctcaaggatc ttaccgctgt tgagatccag ttcgatgtaa      5100
cccactcgtg cacccaactg atcttcagca tcttttactt tcaccagcgt ttctgggtga      5160
gcaaaaacag gaaggcaaaa tgccgcaaaa agggaataa gggcgacacg gaaatgttga      5220
atactcatac tcttcctttt tcaatattat tgaagcattt atcagggtta ttgtctcatg      5280
agcggataca tatttgaatg tatttagaaa aataaacaaa tagggttcc gcgcacattt      5340 ccccgaaaag tgccacctga cgtctaagaa accattatta tcatgacatt aacctataaa      5400
aataggcgta tcacgaggcc ctttcgtc                                         5428

<210> SEQ ID NO 6
<211> LENGTH: 275
<212> TYPE: DNA
<213> ORGANISM: Artificial
<220> FEATURE:
<223> OTHER INFORMATION: synthetic oligonucleotide - polyadenylation
      signal

<400> SEQUENCE: 6
gtttaaaccc gctgatcagc ctcgactgtg ccttctagtt gccagccatc tgttgtttgc       60
ccctcccccg tgccttcctt gaccctggaa ggtgccactc ccactgtcct ttcctaataa      120
aatgaggaaa ttgcatcgca ttgtctgagt aggtgtcatt ctattctggg gggtggggtg      180
gggcaggaca gcaaggggga ggattgggaa gacaatagca ggcatgctgg ggatgcggtg      240
ggctctatgg cttctgaggc ggaaagaacc agctg                                 275

<210> SEQ ID NO 7
<211> LENGTH: 139
<212> TYPE: DNA
<213> ORGANISM: Artificial
<220> FEATURE:
<223> OTHER INFORMATION: synthetic oligonucleotide - human leptin
      promoter and enhancer

<400> SEQUENCE: 7
gctagcagcc gcccggcacg tcgctaccct gagggggcggg gcgggagctg gcgctagaaa       60
tgcgccgggg cctgcggggc agttgcgcaa gttgtgatcg ggccgctata agaggggcgg      120
gcaggcatgg agccccgta                                                   139

<210> SEQ ID NO 8
<211> LENGTH: 884
<212> TYPE: DNA
<213> ORGANISM: Artificial
<220> FEATURE:
<223> OTHER INFORMATION: synthetic oligonucleotide - recombinant
      promoter and enhancer

<400> SEQUENCE: 8
gctagcagcc gcccggcacg tcgctaccct gagggggcggg gcgggagctg gcgctagaaa       60
tgcgccgggg cctgcggggc agttgcgcaa gttgtgatcg ggatccacta gtccagtgtg      120
gtggaattct gcagatatcc agcacagtgg cggccgctcg agtctagaaa gctttaagaa      180
ttcagggcct ttttaacttg ccaagcccca caccactcca ggaacttccc cacaccccag      240
```

```
ttctcagaat tcatgtgcaa ggtctttcct aaatccaggg tccaggtcag agagtggagg    300
atgtgctcta tttcttacct gattgcagac ccctctgaca gtgctccctt ctgaagcact    360
cactgtctga acgtacacag tctcagactt aatcatgcac agtgagcaag actgtggtgt    420
gataattggc gtccctgact tattagggca aatctatggg aggggagac ctcctggacc     480 actgagcaat taattcattt acattaggaa gtttctccgt cagatgcagg aaaaaaatct    540
tgttttcctg ctgtggtttt gattttgccc catcttctgt tgctgttgta ggaggcaaaa    600
taagggtcaa ggcctggaaa cacaagtgct ttgactgaag ctccacttgg cttccgaagc    660
ccaagctggg ttgtaccagg ttccctaggg tgcaggctgt gggcaactgc cagggacatg    720
tgcctgccca ccggcctctg gccctcactg agttggccaa tgggaaatga caattgtgag    780
gtggggactg cctgccccg tgagtaccag gctgttgagg ctgggccacc tcctcctcac     840
ttccattctg actgcagtct gtggttctga ttccatacca gagg                     884
```

<210> SEQ ID NO 9
<211> LENGTH: 313
<212> TYPE: DNA
<213> ORGANISM: Artificial
<220> FEATURE:
<223> OTHER INFORMATION: synthetic oligonucleotide - recombinant
      promoter and enhancer

<400> SEQUENCE: 9

```
gctagcagcc gcccggcacg tcgctaccct gaggggcggg gcgggagctg gcgctagaaa     60
tgcgccgggg cctgcggggc agttgcgcaa gttgtgatcg ggatccacta gtccagtgtg    120
gtggaattct gcagatatcc agcacagtgg cggccgctcg agtctagagc tagcagccgc    180
ccggcacgtc gctaccctga ggggcggggc gggagctggc gctagaaatg cgccggggcc    240
tgcggggcag ttgcgcaagt tgtgatcggg ccgctataag aggggcgggc aggcatggag    300
ccccgtagga tcc                                                        313
```

<210> SEQ ID NO 10
<211> LENGTH: 21
<212> TYPE: DNA
<213> ORGANISM: Artificial
<220> FEATURE:
<223> OTHER INFORMATION: synthetic oligonucleotide - PCR primer

<400> SEQUENCE: 10

```
gatgatctac ctccaaatat g                                               21
```

<210> SEQ ID NO 11
<211> LENGTH: 18
<212> TYPE: DNA
<213> ORGANISM: Artificial
<220> FEATURE:
<223> OTHER INFORMATION: synthetic oligonucleotide - PCR primer

<400> SEQUENCE: 11

```
ctggccccag aagatctg                                                   18
```